US006953781B2

(12) United States Patent
Martin-Lomas et al.

(10) Patent No.: US 6,953,781 B2
(45) Date of Patent: *Oct. 11, 2005

(54) COMPOUNDS AND THEIR USES

(75) Inventors: Manuel Martin-Lomas, Seville (ES); Thomas William Rademacher, Oxford (GB); Hugo Norberto Caro, London (GB); Irene Francois, Woking (GB)

(73) Assignee: Rodaris Pharmaceuticals Limited, Oxfordshire (GB)

( * ) Notice: Subject to any disclaimer, the term of this patent is extended or adjusted under 35 U.S.C. 154(b) by 393 days.

This patent is subject to a terminal disclaimer.

(21) Appl. No.: 09/798,005

(22) Filed: Mar. 2, 2001

(65) Prior Publication Data

US 2001/0051606 A1 Dec. 13, 2001

Related U.S. Application Data

(60) Provisional application No. 60/203,599, filed on May 12, 2000.

(51) Int. Cl.$^7$ .......................... A61K 31/70; C07G 11/00; C07H 15/00

(52) U.S. Cl. .................. 514/25; 536/4.1; 536/17.2; 536/18.4

(58) Field of Search .................. 536/4.1, 17.2, 536/18.4; 514/25

(56) References Cited

U.S. PATENT DOCUMENTS

| 5,268,272 A | | 12/1993 | Mullner et al. | |
|---|---|---|---|---|
| 5,395,828 A | | 3/1995 | Schiebler et al. | |
| 5,550,166 A | | 8/1996 | Ostlund et al. | |
| 5,652,221 A | | 7/1997 | Larner et al. | |
| 6,004,938 A | * | 12/1999 | Frick et al. | 514/25 |
| 6,271,204 B1 | * | 8/2001 | Rademacher et al. | 514/25 |
| 6,716,826 B2 | * | 4/2004 | Martin-Lomas et al. | 514/54 |
| 6,759,390 B2 | * | 7/2004 | Martin-Lomas et al. | 514/25 |

FOREIGN PATENT DOCUMENTS

| EP | 0 520 372 A1 | 12/1992 |
|---|---|---|
| EP | 0 559 064 A2 | 9/1993 |
| EP | 0 845 475 A1 | 6/1998 |
| JP | 63196596 | 8/1988 |
| JP | 03237101 | 10/1991 |
| JP | 04120089 | 4/1992 |
| JP | 06293790 | 10/1994 |
| WO | WO 96/14075 | 5/1996 |
| WO | WO 98/10791 | 3/1998 |
| WO | WO 98/11116 | 3/1998 |
| WO | WO 98/11117 | 3/1998 |
| WO | WO 98/11435 | 3/1998 |
| WO | WO 98/50049 | 11/1998 |
| WO | WO 99/06421 | 2/1999 |
| WO | WO 99/38516 | 8/1999 |
| WO | WO 00/15254 | 3/2000 |
| WO | WO 00/39141 | 7/2000 |

OTHER PUBLICATIONS

Schweizer, T.F. et al, J. Sci.Fd. Agric., 1978, 29, 148–154.*
Fernandez de la Pradilla, R. et al., "Improved preparation of acetals of myo–inositol and its (±)–1–benzyl ether: conformational analysis of di–O–isopropylidene–myo–inositol derivatives"; Carbohydrate Research, 207: 249–257 (1990).
Bernabé, M. et al., "Chiral recognition of 1–O–allyl and 1–O–benzyl–D– and –L– myo–inositol by cyclomaltohexaose and –heptaose (α–and β–cyclodextrin)"; Carbohydrate Research, 208: 255–259 (1990).
Zapata, A. et al., "Novel Highly Regioselective O–Alkylation and O–Acylation of myo–Inositol"; J. Org. Chem., 56: 444–447 (1991).
Jaramillo, C. et al., "Synthesis of 1D–1,2–anhydro–myo-inositol"; Carbohydrate Research, 209: 296–298 (1991).
Jaramillo, C. et al., "Approaches to the Synthesis of Glycosyl Phosphatidyl Inositols. Enantioselective Synthesis of Optically Active chiro– and myo–Inositols."; Tetrahedron Letters, 32(22): 2501–2504 (1991).
Vasella, A. et al., "194. Convenient Synthesis of 2–Azido–2–deoxy–aldoses by Diazo Transfer"; Helvetica Chimica Acta, 74: 2073–2077 (1991).
Aguiló, A. et al., "The Regioselective Synthesis of Enantiomerically Pure myo–Inositol Derivatives. Efficient Synthesis of myo–Inositol 1,4,5–triphosphate."; Tetrahedron Letters, 33(3): 401–404 (1992).
Zapata, A. et al., "Building blocks for the synthesis of glycosyl–myo–inositols involved in the insulin intracellular signalling process"; Carbohydrate Research, 234: 93–106 (1992).
Caro, H. et al., "Syntheses and insulin–like activity of phosphorylated galactose derivatives"; Carbohydrate Research, 240: 119–131 (1993).
Singh, K. et al., "Synthesis of Oligosaccharides Structurally Related to E–Selectin Ligands", J. Chem. Soc., Chem. Commun., 775–776 (1994).
Chiara, J.L. et al., "A Stereoselective Route to Enantiomerically Pure myo–Inositol Derivatives Starting from D–Mannitol", Tetrahedron Letters, 35(18): 2969–2972 (1994).
Zapata, A. et al., "Synthesis and investigation of the possible insulin–like activity of 1D–4–O– and 1D–6–O–(2–amino–2–deoxy–α–D–glucopyranosyl)– myo–inositol 1–phosphate and 1D–6–O–(2–amino–2–deoxy–α–D– glucopyranosyl)– myo–inositol 1,2–(cyclic phosphate)"; Carbohydrate Research, 264: 21–31 (1994).

(Continued)

Primary Examiner—James O. Wilson
Assistant Examiner—Ganapathy Krishnan
(74) Attorney, Agent, or Firm—Dann, Dorfman, Herrell & Skillman, P.C.

(57) ABSTRACT

Compounds having a mimetic or antagonistic property of an inositol phosphoglycan, and the uses of these compounds are disclosed, together with the use, e.g. to treat a condition ameliorated by administration of an IPG second messenger or an IPG antagonist thereof. In particular, the compounds are based on the 1,6 linkage of a sugar residue and a cyclitol.

15 Claims, 15 Drawing Sheets

OTHER PUBLICATIONS

Jaramillo, C. et al., "An Effective Strategy for the Synthesis of 6–O–(2–Amino–2–deoxy–α–D–glycopyranosyl)–D–chiro– and –D–myo–inositol 1–Phosphate Related to Putative Insulin Mimetics"; J. Org. Chem., 59: 3135–3141 (1994).

Varela–Nieto, I. et al., "Cell Signalling by Inositol Phosphoglycans from Different Species"; Comp. Biochem. Physiol., 115B(2): 223–241 (1996).

Martin–Lomas, M. et al., "The solution conformation of glycosyl inositols related to inositolphosphoglycan (IPG) mediators"; Tetrahedron: Asymmetry, 11: 37–51 (2000).

Baeschlin, D.K. et al., "1,2–Diacetals in Synthesis: Total Synthesis of a Glycosylphosphatidylinositol Anchor of *Trypanosoma brucei*"; Chem. Eur. J., 6(1): 172–186 (2000).

Frick, W. et al., "Structure–Activity Relationship of Synthetic Phosphoinositolglycans Mimicking Metabolic Insulin Action"; Biochemistry, 37(38): 13421–13436 (1998).

Jaworek, C.H. et al., "Synthesis of an Inositol–Containing Trisaccharide Related to Insulin Signal Transduction"; Tetrahedron Letters, 40: 667–670 (1999).

Deeg, M.A. et al., "Inositol Glycan Phosphate Derived from Human Erythrocyte Acetylcholinesterase Glycolipid Anchor and Inositol Cyclic 1,2–Phosphate Antagonize Glucagon Activation of Glycogen Phosphorylase"; Diabetes, 42(9): 1318–1323 (1993).

Güther, M.L.S. et al., "Molecular species analysis and quantification of the glycosylphosphatidylinositol intermediate glycolipid C from *Trypanosoma brucei*"; Mol. Biochem. Parasitol., 77(2): 137–145 (1996).

Mayer, T.G. et al., "Glycosyl Phosphatidylinositol (GPI) Anchor Synthesis Based on Versatile Building Blocks—Total Synthesis of a GPI Anchor of Yeast"; Eur. J. Org. Chem. 1153–1165 (1999).

Müller, G. et al., "Phosphoinositolglycan–Peptides from Yeast Potently Induce Metabolic Insulin Actions in Isolated Rat Adipocytes, Cardiomyocytes, and Diaphragms"; Endocrinology, 138: 3459–3475 (1997).

Baeschlin, D.K. et al., "Rapid Assembly of Oligosaccharides: Total Synthesis of a Glycosylphosphatidylinositol Anchor of *Trypanosoma brucei*"; Angew. Chem. Int. Ed., 37(24): 3423–3427 (1998).

Derappe, C. et al., "Characterization of a New Oligosaccharide Containing myo–Inositol Found in Pregnancy Urine"; Carbohydrate Research, 115: 221–229 (1983).

Angyal, S.J. et al., "Cyclitols. Part XXII. Synthesis of Some Mannosyl– and Mannosyl–mannosyl–myoinositols, and of Galactinol"; J. Chem. Soc. (C), 433–438 (1966).

Reddy, K.K. et al., "Insulin Second Messengers: Synthesis of 6–O–(2–Amino–2–deoxy–α–D–glycopyranosyl)–D–chiro–inositol–1–phosphate"; Tetrahedron Lets., 34(49): 7869–7872 (1993).

Plourde, R. et al., "Synthesis of a Potentially Insulin–Mimetic Phosphodisaccharide", Tetrahedron Lets., 31(19): 2693–2696 (1990).

Stralfors, P., "Insulin second messengers"; Bioessays, 19: 327–335 (1997).

Field, M.C., "Is there evidence for phospho–oligosaccharides as insulin mediators?"; Glycobiology, 7: 161–168 (1997).

Jones, D.R. et al., "The role of glycosyl–phosphatidylinositol in signal transduction"; Int. J. Biochem. Cell Biol., 39: 313–326 (1998).

Mato, J.M. et al., "Partial Structure of an Insulin–Sensitive Glycophospholipid"; Biochem. Biophys. Res. Commun., 146: 764–770 (1987).

Larner, J., "Rat Liver Insulin Mediator Which Stimulates Pyruvate Dehydrogenase Phosphatase Contains Galactosamine and D–Chiroinositol"; Biochem. Biophys. Res. Commun., 151: 1416–1426 (1988).

Caro, H.N. et al., "Isolation of Partial Characterisation of Insulin–Mimetic Inositol Phosphoglycans from Human Liver"; Biochem. Mol. Med., 61: 214–228 (1997).

Gigg, R. et al., "Synthesis of Glycosylphosphatidylinositol Anchors"; in "Glycopeptides and Related Compounds"; Large & Warren, Eds., Marcel Dekker, New York, 327–392 (1997).

Corey, E.J. et al., "Protection of Hydroxyl Groups as tert-Butyldimethylsilyl Derivatives"; J. Am. Chem. Soc., 94: 6190–6191 (1972).

Ley, S.V. et al., "Cyclohexane–1,2–diacetals (CDA): A New Protecting Group for Vicinal Diols in Carbohydrates"; Angew. Chem. Int. Ed. Engl., 33: 2290–2292 (1994).

Kinzy, W. et al., "Synthese des Trisaccharids aus der 'Repeating Unit' des Kapselpolysaccharids von *Neisseria meningitidis* (Serogruppe L)"; Liebigs Ann. Chem., 1537–1545 (1985).

Schmidt, R.R. et al., "Anomeric–Oxygen Activation for Glycoside Synthesis: the Trichloroacetimidate Method"; Adv. Carbohydr. Chem. Biochem. 50: 21–123 (1994).

Rademacher, T.W. et al., "Inositolphosphoglycan second messengers"; Brazilian J. Med. Biol. Res., 27: 327–341 (1994).

Murakata, C. et al., "Stereoselective total synthesis of the glycosyl phosphatidylinositol (GPI) anchor of *Trypanosoma brucei*"; Carbohydrate Research, 235: 95–114 (1992).

Martin–Lomas, M. et al., "Inositolphosphoglycan Mediators Structurally Related to Glycosyl Phosphatidylinositol Anchors: Synthesis, Structure and Biological Activity"; Chem. Eur. J., 6(19): 3608–3621 (2000).

Ruda, K. et al., "Synthesis of an Inositol Phosphoglycan Fragment found in Leishmania Parasites"; Tetrahedron, 56(24): 3969–3975 (2000).

Dietrich, H. et al., "Glycosyl Inositol Derivatives Related to Inositolphosphoglycan Mediators: Synthesis, Structure, and Biological Activity"; Chem. Eur. J., 5(1): 320–336 (1999).

Smith, T.K. et al., "Parasite and mammalian GPI biosynthetic pathways can be distinguished using synthetic substrate analogues"; The EMBO Journal, 26(22): 6667–6675 (1997).

Fankhauser, C. et al., "Structures of Glycosylphosphatidylinositol Membrane Anchors from *Saccharomyces cerevisiae*"; J. Biol. Chem., 268(35): 26365–26374 (1993).

Menon, A.K. et al., "Cell–free Synthesis of Glycosyl–phosphatidylinositol Precursors for the Glycolipid Membrane Anchor of *Trypanosoma brucei* Variant Surface Glycoproteins"; J. Biol. Chem., 265(16): 9033–9042 (1990).

Sakata, K. et al., "2–O–(β–L–Arabinopyranosyl)–myo–inositol as a Main Consultant of Tea (*Camellia Sinensis*)"; Agric. Biol. Chem., 53(11): 2975–2969 (1989).

Gorin, P.A.J. et al., "Formation of O–β–D–Glucopyranosyl– and O–β–D–Galactopyranosyl–Myo–Inositols by Glycosyl Transfer"; Can. J. Chem., 43(8): 2259–2264 (1965).

Quemener, B. et al., "Ciceritol, A Pinitol Digalactoside from Seeds of Chickpea, Lentil and White Lupin", Phytochemistry, 22(8): 1745–1751 (1983).

Carter, H.E. et al., "Biochemistry of the Sphingolipids. XVIII. Complete Structure of Tetrasaccharide Phytoglycolipid"; Biochemistry, 8(1): 383–388 (1969).

Wait, R. et al., "Strategies for the structure determination of parasite glycoconjugates using fast atom bombardment mass spectrometry"; Cienc. Cult. (Sao Paulo), 46(4): 255–261 (1994).

Previato, J.O. et al., "Structural Characterization of a Novel Class of Glycophosphosphingolipids from the Protozoan *Leptomonas samueli*"; J. Biol. Chem., 267(34): 24279–24286 (1992).

Hsieh, T.C.Y. et al., "Glycophosphoceramides from Plants—Purification and Characterization of a Novel Tetrasaccharide Derived from Tobacco Leaf Glycolipids"; J. Biol. Chem., 256(15): 7747–55 (1981).

Wait, R. et al., "Structure Determination of Phosphoinositol Oligosaccharides from Parasitic Protozoa Using Fast Atom Bombardment Mass Spectrometry"; Org. Mass Spectrom., 29(12): 767–781 (1994).

Smith, C.K. et al., "α–D–Mannopyranosyl–(1→4)–α–glucuronopyranosyl–(1→2)–myo–inositol, a new and unusual oligosaccharide from cultured rose cells"; Phytochemistry, 52: 387–396 (1999).

Ley, S.V. et al., "Microbial Oxidation in Synthesis: Preparation of a Potential Insulin Mimic from Benzene"; Synlett, 12: 997–998 (1992).

Crossman, Jr., A. et al., "Synthesis of some second generation substrate analogues of early intermediates in the biosynthetic pathway of glycosylphosphatidylinositol membrane anchors"; Carbohydrate Research, 321(1–2): 42–51 (1999).

Crossman, Jr. A. et al., "Parasite glycoconjugates. Part 7. Synthesis of further substrate analogues of early intermediates in the biosynthetic pathway of glycosylphosphatidylinositol membrane anchors"; J. Chem. Soc., Perkin Trans. 1: 2769–2774 (1997).

Smith, T.K. et al., "Substrate Specificity of the Dolichol Phosphate Mannose: Glucosaminyl Phosphatidylinositol α1–4–Mannosyltransferase of the Glycosylphosphatidylinositol Biosynthetic Pathway of African Trypanosomes"; J. Biol. Chem., 271(11): 6476–6482 (1996).

Cottaz, S. et al., "Parasite glycoconjugates. Part 3. Synthesis of substrate analogues of early intermediates in the biosynthetic pathway of glycosylphosphatidylinositol membrane anchors"; J. Chem. Soc. Perkin Trans. 1: 1673–1678 (1995).

Smith, T.K. et al., "Parasite–Specific Inhibition of the Glycosylphosphatidylinositol Biosynthetic Pathway by Stereoisometric Substrate Analogues"; Biochemisty, 39: 11801–11807 (2000).

Morris, J.C. et al., "Glycan Requirements of Glycosylphosphatidylinositol Phospholipase C from *Trypansoma brucei*"; J. Biol. Chem., 270(6): 2517–2524 (1995).

Kunjara, S. et al., "Tissue Specific Release of Inositol Phosphoglycans"; Biopolymers and Bioproducts: Structure, Function and Applications, 301–306 (1995).

Khiar, N. et al., "Strategies for the Synthesis of Inositol Phosphoglycan Second Messengers"; Carbohydrate Mimics, Concepts and Methods, Chapleur Ed. Wiley VCH, 443–462 (1998).

* cited by examiner

RGL 1115

*Reagents and conditions:* i) dibenzyl diisopropylphosphoramidite, tetrazole, anhydrous DCM, R.T., 72 hrs, then mCPBA, anhydrous DCM, -40 °C, 3 hrs. ii) TBAF [1.0 M solution in THF], THF, 0 °C, 1 hr. iii) TFA, DCM, water, R.T., 4 hrs. iv) $H_2$, Pd/C (10 % wt.), HPLC grade MeOH:distilled water (4:1).

COMPOUNDS AND THEIR USES

CROSS REFERENCE TO RELATED APPLICATIONS

This application claims the benefit of U.S. Provisional Application No. 60/203,599, filed May 12, 2000, the entire disclosure of which is incorporated by reference in this application.

FIELD OF THE INVENTION

The present invention relates to compounds and their uses, and in particular to compounds which have a mimetic or antagonistic property of an inositol phosphoglycan, and the uses of these compounds, e.g. to treat a condition ameliorated by administration of an IPG second messenger or an IPG antagonist thereof.

BACKGROUND OF THE INVENTION

Many of the actions of growth factors on cells are thought to be mediated by a family of inositol phosphoglycan (IPG) second messengers[13]. It is thought that the source of IPGs is a "free" form of glycosyl phosphatidylinositol (GPI) situated in cell membranes. IPGs are thought to be released by the action of phosphatidylinositol-specific phospholipases following binding of growth factors to receptors on the cell surface. There is evidence that IPGs mediate the action of a large number of growth factors including insulin, nerve growth factor, hepatocyte growth factor, insulin-like growth factor I (IGF-I), fibroblast growth factor, transforming growth factor β, the action of IL-2 on B-cells and T-cells, ACTH signalling of adrenocortical cells, IgE, FSH and hCG stimulation of granulosa cells, thyrotropin stimulation of thyroid cells, cell proliferation in the early developing ear and rat mammary gland.

Partially characterised inositolphosphoglycans (IPGs) have been postulated to mediate the action of a number of growth factors including insulin and insulin-like growth factor I (IGF-I)[1]. Despite their isolation from several tissues type, the precise chemical structures of these IPGs are, however, still unknown and two main structural groups have been proposed on the basis of the chemical composition[2,3] which display different biological activity and tissue distribution [4]; the family of glucosamine-myo-inositol containing IPGs (IPG-A) and the family of chiro-inositol-galactosamine containing IPG-s (IPG-P).

In an attempt to establish the minimal structural requirements for biological activity, a number of compounds containing some of the basic structural motifs that have been postulated for IPG mediators have been synthesised in the art[5]. These synthetic compounds include O-(2-amino-2-deoxy-D-glucopyranosyl)-α(1-6)-chiro-inositol 1-phosphate and O-(2-amino-2-deoxy-D-glucopyranosyl)-α(1-6)-myo-inositol 1-phosphate[6].

U.S. Pat. No. 6,004,938 (Hoechst) discloses a group of synthetic inositol glycans having insulin-like action. The compounds are based on 2–6 monsaccharide units linked to an inositol moiety. The examples in the patent all employ myo-inositol and are composed of 5 or 6 units apart from two pseudo-trisaccharide compounds G and H. Compounds G and H are HO—PO(H)O-6Man-α(1-4)-GluN-α(1-6)-(L)inositol-1,2(cyclic) phosphate and HO—PO(H)O-6Man-α(1-4)-GluN-α(1-6)-(L)inositol, otherwise known as O-(6-hydrogenphosphonate-α-D-mannopyranosyl)-(1-4)-(2-ammonio-2-deoxy-α-D-glucopyranosyl)-(1-6)-L-myo-inositol-1,2-cyclic phosphate and O-(6-hydrogenphosphonate-α-D-mannopyranosyl)-(1-4)-(2-amino-2-deoxy-α-D-glucopyranosyl)-L-myo-inositol. The properties of exemplified compounds are investigated in lipogenesis and glucose transport assays employing rat fat cells.

WO96/14075 (University of Virginia) discloses a generic family of compounds D-hexosamines linked to an inositol via a β1,4-linkage. The inositols can be myo or chiro-inositol or pinitol, while the hexosamines are glucosamine or galactosamine. However, this application describes the synthesis of just two compounds 4-O-(2-deoxy-2-amino-β-D-galactopyranosyl)-D-pinitol and 4-O-(2-deoxy-2-amino-β-D-galactopyranosyl)-D-chiro-inositol, or in IUPAC notation O-(2-amino-2-deoxy-(β-D-galactopyranosyl)-(1-4)-D-pinitol and O-(2-amino-2-deoxy-β-D-galactopyranosyl)-(1-4)-D-chiro-inositol.

WO99/06421 (University of Virginia) describes synthetic insulin mimetic substances and includes a general formula I showing β1,4-linked disaccharides. However, despite this the compounds synthesised in this application are exactly the same as those disclosed in the applicant's earlier application, WO96/14075.

A multi-step synthesis of a IPG-P mimetic from glucose has been previously reported in Jaramillo et al[6], which discloses a compound called C4, 1-D-6-O-(2-amino-2-deoxy-α-D-glucopyranosyl)-chiro-inositol 1-phosphate. A further synthesis of C4 is described in our co-pending International Patent Application PCT/GB99/03715 (Rademacher Group Limited). Zapata et al[16] discloses three other compounds C1–3 which are:

C1 1-D-4-O-(2-amino-2-deoxy-α-D-glucopyranosyl)-myo-inositol 1-phosphate.
C2 1-D-6-O-(2-amino-2-deoxy-α-D-glucopyranosyl)-myo-inositol 1-phosphate.
C3 1-D-6-O-(2-amino-2-deoxy-α-D-glucopyranosyl)-myo-inositol 1,2 cyclic-phosphate.
C4 1-D-6-O-(2-amino-2-deoxy-α-D-glucopyranosyl)-chiro-inositol 1-phosphate.

It remains a significant problem in the art to produce synthetic compounds which can mimic one or more of the activities of inositol phosphoglycans or which act as antagonists of IPGs.

SUMMARY OF THE INVENTION

Broadly, the present invention relates to IPG mimetic and antagonist compounds and to methods of producing the compounds and to their medical uses. The compounds disclosed herein are useful as synthetic mimetics of IPG-P or IPG-A second messengers and/or growth factors whose action is mediated by IPGs, or a competitive antagonists of IPGs. In particular, the compounds are based on the 1,6 linkage of a sugar residue and a cyclitol.

Accordingly, in a first aspect, the present invention provides a compound represented by the general formula:

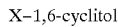

wherein:
X represents a sugar residue;
the sugar residue is unsubstituted or substituted with between one and four groups, and the cyclitol is unsubstituted or is further substituted with between one and four groups, the group or groups being as defined herein;
with the proviso that the compound is not 1-D-4-O-(2-amino-2-deoxy-α-D-glucopyranosyl)-myo-inositol 1-phosphate, 1-D-6-O-(2-amino-2-deoxy-α-D-glucopyranosyl)-myo-inositol 1-phosphate, 1-D-6-O-(2-amino-2-deoxy-α-D-glucopyranosyl)-myo-inositol 1,2 cyclic-phosphate, 1-D-6-O-(2-amino-2-deoxy-α-D-glucopyranosyl)-chiro-inositol 1-phosphate, O-(6-hydrogenphosphonate-α-D-mannopyranosyl)-(1-4)-(2-ammonio-2-deoxy-α-D-glucopyranosyl)-(1-6)-L-myo-inositol-1,2-cyclic phosphate or O-(6-hydrogenphosphonate-α-D-mannopyranosyl)-(1-4)-(2-amino-2-deoxy-α-D-glucopyranosyl)-L-myo-inositol.

In a further aspect, the present invention provides the present invention provides a compound represented by the general formula:

$$X\text{-}\alpha 1,6\text{-cyclitol}$$

wherein:
X represents a sugar residue;
the sugar residue is unsubstituted or substituted with between one and four groups, and the cyclitol is unsubstituted or is further substituted with between one and four groups, the group or groups being as defined herein;
with the proviso at the compound is not 1-D-4-O-(2-amino-2-deoxy-α-D-glucopyranosyl)-myo-inositol 1-phosphate, 1-D-6-O-(2-amino-2-deoxy-α-D-glucopyranosyl)-myo-inositol 1-phosphate, 1-D-6-O-(2-amino-2-deoxy-α-D-glucopyranosyl)-myo-inositol 1,2 cyclic-phosphate, 1-D-6-O-(2-amino-2-deoxy-α-D-glucopyranosyl)-chiro-inositol 1-phosphate, O-(6-hydrogenphosphonate-α-D-mannopyranosyl)-(1-4)-(2-ammonio-2-deoxy-α-D-glucopyranosyl)-(1-6)-L-myo-inositol-1,2-cyclic phosphate or O-(6-hydrogenphosphonate-α-D-mannopyranosyl)-(1-4)-(2-amino-2-deoxy-α-D-glucopyranosyl)-L-myo-inositol.

In a further aspect, the present invention provides the present invention provides a compound represented by the general formula:

$$X\text{-}\beta 1,6\text{-cyclitol}$$

wherein:
X represents a sugar residue;
the sugar residue is unsubstituted or substituted with between one and four groups, and the cyclitol is unsubstituted or is further substituted with between one and four groups, the group or groups being as defined herein.

Preferably, the sugar residue is a hexose or a pentose, and may be an aldose or a ketose. The sugar residue can a member of the D or L series and can include amino sugars, deoxy sugars and their uronic acid derivatives. Preferably, where the sugar residue is a hexose, it is selected from the group consisting of glucose, galactose or mannose, or substituted hexose sugar residues such as an amino sugar residue such as hexosamine, galactosamine or glucosamine, and more preferably D-glucosamine (2-amino-2-deoxy-D-glucose) or D-galactosamine (2-amino-2-deoxy-D-galactose) Preferred pentose sugar residues include arabinose, fucose and ribose. The sugar residue is optionally substituted at one, two, three or four positions, other than the position of linkage to the cyclitol moiety.

The cyclitol moiety is preferably selected from myo-inositol, chiro-inositol or pinitol (3-O-methyl-chiro-inositol), in either their D or L forms, and is optionally substituted at one or more of the positions other than the position of linkage to the sugar radical, or in the case of pinitol additionally the 3-position. The sugar radical is optionally substituted at one, two, three or four positions other than at the position of linkage to the inositol moiety or the anomeric position. Where the cyclitol moiety is substituted at the 3-position (e.g. is a pinitol or a related compound), preferably the substituent is $C_{1-10}$ alkyl, and may be a substituted or unsubstituted primary, secondary or tertiary alkyl group. Examples of substituted groups include $CF_3$, $X(CH_2)_n$—O— (where X is hydrogen, or substituted or unsubstituted alkyl), $CHF_2O$—. A preferred alkyl group is methyl when the cyclitol is D or L-pinitol (3-O-methyl-chiro-inositol), and is optionally substituted at one or more of the positions other than the 3-position or the position of linkage to the sugar residue. In further embodiments, the cyclitol may have one or more of the hydroxyl groups through which the substituents described above are removed so that any substituent(s) are linked to the ring carbon atom. The sugar residue is optionally substituted at one, two, three, four or five positions other than at the position of linkage to the inositol moiety.

In these and other aspects of the invention, preferably the substituent group or groups of the cyclitol moiety and the sugar residue are independently selected from:
(a) phosphoryl groups such as phosphate —O—P(O)(OH)$_2$; thiophosphate —O—P(S)(OH)$_2$; phosphate esters —O—P(O)(OR)$_2$; thiophosphate esters —O—P(S)(OR)$_2$; phosphonate —O—P(O)OHR; thiophosphonate —O—P(S)OHR; substituted phosphonate —O—P(O)OR$_1$R$_2$; substituted thiophosphonate —O—P(S)OR$_1$R$_2$; —O—P(S)(OH)(SH); cyclic phosphate;
(b) other phosphorus containing compounds such as phosphoramidite —O—P(OR)—NR$_1$R$_2$ and phosphoramidate —O—P(O)(OR,)—NR$_1$R$_2$;
(c) sulphur groups such as —O—S(O)(OH), —SH, —SR, —S(—O)—R, —S(O)$_2$R, RO—S(O)$_2$, —O—SO$_2$NH$_2$, —O—SO$_2$R$_1$R$_2$ or sulphamide —NHSO$_2$NH$_2$;
(d) amino groups such as —NHR, —NR$_1$R$_2$, —NHAc, —NHCOR, —NH—O—COR, —NHSO$_3^-$, —NHSO$_2$R, —N(SO$_2$R)$_2$, and/or amidino groups such as —NH—C(=NH)NH$_2$ and/or ureido groups such as —NH—CO—NR,R$_2$ or thiouriedo groups such as —NH—C(S)—NH$_2$;
(e) hydroxy groups and substituted hydroxy groups such as —OR$_3$, where R$_3$ is $C_{1-10}$ unsubstituted or substituted alkyl, e.g. $CHF_2$ or $CF_3$, alkoxyalkyl, aryloxyalkyl, cycloalkyl, alkenyl (unsubstituted alkyl), alkylene ($C_{3-7}$ cycloalkyl), —OCOR, aryl, heteroaryl, acetal, or where two hydroxyl groups are joined as a ketal;
(f) halogen substituents such as fluorine or chlorine;
(g) hydrogen, e.g. to provide a deoxy sugar;
wherein R, R$_1$ and R$_2$ are independently hydrogen or $C_{1-10}$ unsubstituted or substituted alkyl or aryl.

The compounds may be provided as racemic or diastereomeric mixtures, resolved or partially resolved optical isomers, and as pharmaceutically acceptable salts, esters and derivatives as discussed in more detail below.

In a further aspect, the present invention provides a compound represented by the general formula:

$$X\text{-}\alpha 1,6\text{-myo-inositol}$$

wherein:
X represents a sugar residue;
the sugar residue is unsubstituted or substituted with between one and four groups, and the inositol is unsubstituted or is further substituted with between one and four groups, the group or groups being as defined herein;

with the proviso that the compound is not 1-D-4-O-(2-amino-2-deoxy-α-D-glucopyranosyl)-myo-inositol 1-phosphate, 1-D-6-O-(2-amino-2-deoxy-α-D-glucopyranosyl)-myo-inositol 1-phosphate, 1-D-6-O-(2-amino-2-deoxy-α-D-glucopyranosyl)-myo-inositol 1,2 cyclic-phosphate.

Examples of compounds within this aspect of the invention are RGL1023, RGL1027 and RGL1029.

In a further aspect, the present invention provides a compound represented by the general formula:

X-α1,6-chiro-inositol wherein:

X represents a sugar residue;

the sugar residue is unsubstituted or substituted with between one and four groups, and the inositol is unsubstituted or is further substituted with between one and four groups, the group or groups being as defined herein, with the proviso that the compound is not 1D-6-O-(2-amino-2-deoxy-α-D-glucopyranosyl)-D-chiro-inositol 1-phosphate.

Examples of compounds within this aspect of the invention are RGL1017 and derivatives thereof.

In a further aspect, the present invention provides a compound represented by the general formula:

X-α1,6-pinitol wherein:

X represents a sugar residue;

the sugar residue is unsubstituted or substituted with between one and four groups, and the pinitol is unsubstituted or is further substituted with between one and four groups, the group or groups being as defined herein.

Examples of compounds within this aspect of the invention are RGL1024 and RGL1025.

In a further aspect, the present invention provides a compound represented by the general formula:

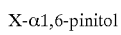

X-β1,6-myo-inositol wherein:

X represents a sugar residue;

the sugar residue is unsubstituted or substituted with between one and four groups, and the inositol is unsubstituted or is further substituted with between one and four groups, the group or groups being as defined herein.

Examples of compounds within this aspect of the invention are RGL1002.

In a further aspect, the present invention provides a compound represented by the general formula:

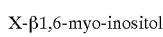

X-β1,6-chiro-inositol wherein:

X represents a sugar residue;

the sugar residue is unsubstituted or substituted with between one and four groups, and the inositol is unsubstituted or is further substituted with between one and four groups, the group or groups being as defined herein.

Examples of compounds within this aspect of the invention are RGL1018 and RGL1019.

In a further aspect, the present invention provides a compound represented by the general formula:

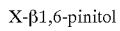

X-β1,6-pinitol wherein:

X represents a sugar residue;

the sugar residue is unsubstituted or substituted with between one and four groups, and the inositol is unsubstituted or is further substituted with between one and four groups, the group or groups being as defined herein.

Examples of compounds within this aspect of the invention are RGL1015 and derivatives thereof.

In preferred embodiments, the present invention provides a compound, or a substituted form thereof as defined above, selected from the group consisting of:

RGL1023 O-(2'-amino-2'-deoxy-6'-phosphate-D-glucopyranosyl)-α(1,6)-D-myo-inositol.

RGL1027 O-(2'-amino-2'-deoxy-4'-phosphate-D-glucopyranosyl)-α(1,6)-D-myo-inositol.

RGL1029 O-(2'-amino-2'-deoxy-3'-phosphate-D-glucopyranosyl)-α(1,6)-D-myo-inositol.

RGL1017 O-(2'-amino-2'-deoxy-D-glucopyranosyl)-α(1,6)-D-chiro-inositol.

RGL1024 O-(2-amino-2-deoxy-D-glucopyranosyl)-α(1,6)-D-3-O-methyl-chiro-inositol.

RGL1025 O-(2-amino-2deoxy-D-galactopyranosyl)-α(1,6)-D-3-O-methyl-chiro-inositol.

RGL1018 O-(2'-amino-2'-deoxy-D-lucopyranosyl)-β(1,6)-D-chiro-inositol.

RGL1019 O-(2'-amino-2'-deoxy-D-lucopyranosyl)-α(1,6)-D-chiro-inositol-1-phosphate.

RGL1015 O-(2-amino-2-deoxy-D-lucopyranosyl)-β(1,6)-3-O-methyl-chiro-inositol.

RGL1105 1"-D-4'O-(6"-phosphate-α-D-mannopyranosyl)-[1'-D-6-O-(2'-amino-2'-deoxy-α-D-glucanopyranosyl)-myo-inositol].

RGL1115 1'-D-6-O-(2'-amino-2'-deoxy-α-D-glucopyranosyl)-5-O-phosphate myo-inositol.

RGL1121 1'-D-1-O-(2'-amino-2'-deoxy-α-D-galactopyranosyl)-D-chiro-inositol.

RGL1120 1'-D-6-O-(2'-amino-2'-deoxy-β-D-glucopyranosyl)-D-chiro-inositol.

RGL1129 1'-D-2-O-(2'-amino-2'-deoxy-α-D-galactopyranosyl)-D-chiro-inositol.

RGL1122 1'-D-5-O-(2'-amino-2'-deoxy-α-D-glucopyranosyl)-D-chiro-inositol.

RGL1115 1'-D-6-O-(2'-amino-2'-deoxy-α-D-glucanopyranosyl)-5-O-phosphate-myo-inositol.

RGL1116 1'-D-6-O-(2'-amino-2'-deoxy-α-D-glucopyranosyl)-D-5-O-acetyl-myo-inositol.

RGL1117 1'-D-5-O-(2'-amino-2'-deoxy-α-D-glucopyranosyl)-D-6-O-acetyl-myo-inositol.

In a further aspect, the present invention provides methods for making the compounds of the invention or their intermediates as set out in the following experimental description and the schemes. In a further related aspect, the present invention further relates to compounds which are the novel intermediates described herein.

In a further aspect, the present invention provides one or more of the above compounds for use in a method of medical treatment. The compounds may be useful as IPG mimetics or IPG antagonists, e.g. competitive antagonists.

In a further aspect, the present invention provides the use of one or more of the above compounds for the preparation of a medicament for the treatment of a condition ameliorated by the administration of an inositol phosphoglycan (IPG) second messenger or an IPG antagonist. Examples of such conditions are set out in the pharmaceutical uses section below.

In a further aspect, the present invention provides a method of treating a condition in a mammal ameliorated by an inositol phosphoglycan (IPG) second messenger or an IPG antagonist, the method comprising administering to the mammal a therapeutically effective amount of one or more of the above compounds.

Embodiments of the invention will now be described by way of example and not limitation with reference to the accompanying drawings.

DETAILED DESCRIPTION

Figure 1:
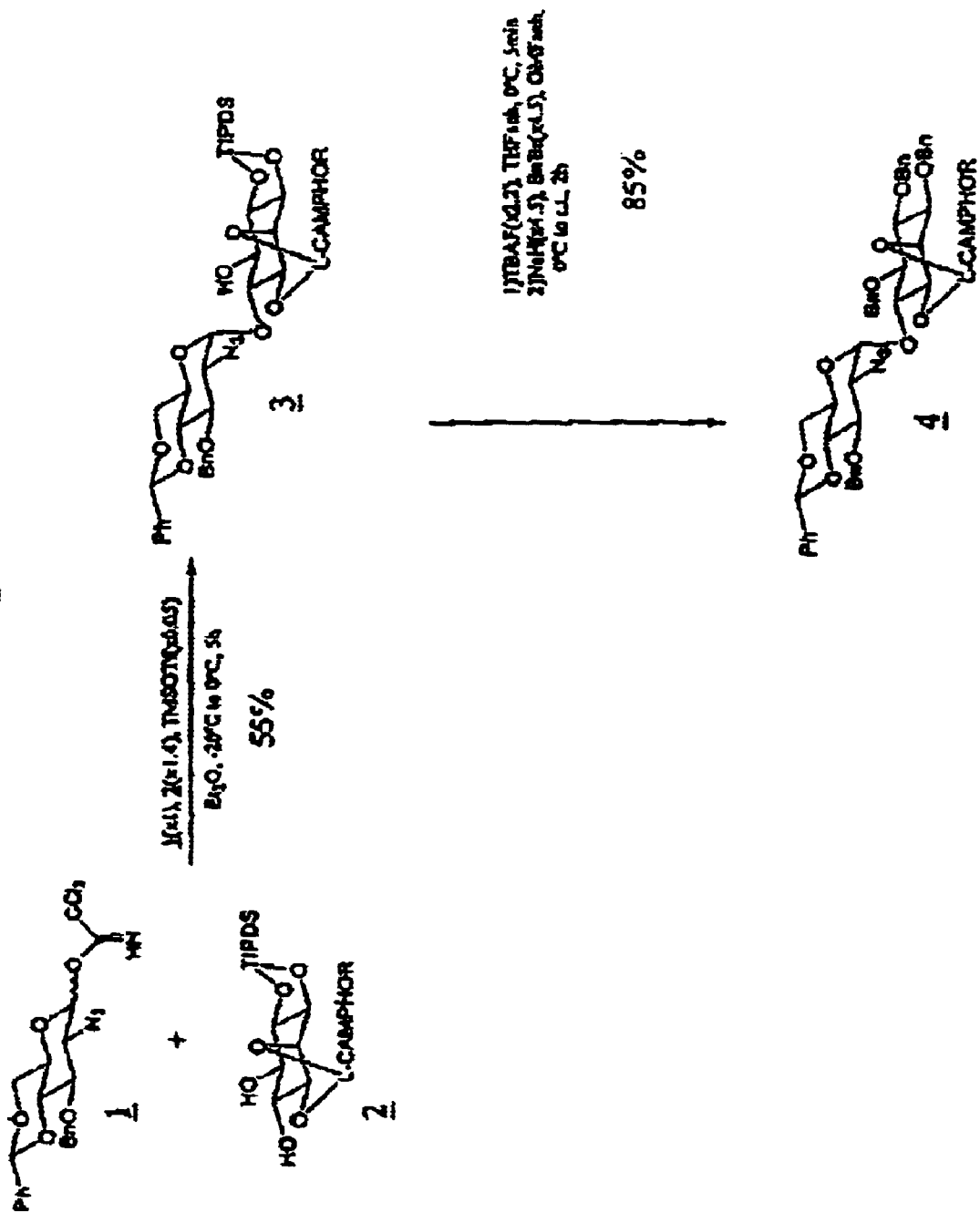
FIG. 1 shows a reaction scheme for the coupling of diol 2 with trichloroacetimidate 1 resulting in 6-O-glycosylation. Subsequent manipulation of protective groups afforded compound 4.

Inositol phosphoglycans (IPGs,

IPG-A mediators modulate the activity of a number of insulin-dependent enzymes such as cAMP dependent protein kinase (inhibits), adenylate cyclase (inhibits) and cAMP phospho-diesterases (stimulates). In contrast, IPG-P mediators modulate the activity of insulin-dependent enzymes such as pyruvate dehydrogenase phosphatase (stimulates) and glycogen synthase phosphatase (stimulates). The A-type mediators mimic the lipogenic activity of insulin on adipocytes, whereas the P-type mediators mimic the glycogenic activity of insulin on muscle. Both A-and P-type mediators are mitogenic when added to fibroblasts in serum free media. The ability of the mediators to stimulate fibroblast proliferation is enhanced if the cells are transfected with the EGF-receptor. A-type mediators can stimulate cell proliferation in the chick cochleovestibular ganglia.

Soluble IPG fractions having A-type and P-type activity have been obtained from a variety of animal tissues including rat tissues (liver, kidney, muscle, brain, adipose, heart) and bovine liver. IPG-A and IPG-P biological activity has also been detected in human liver and placenta, malaria parasitized RBC and mycobacteria. The ability of an anti-inositolglycan antibody to inhibit insulin action on human placental cytotrophoblasts and BC3H1 myocytes or bovine-derived IPG action on rat diaphragm and chick cochleovestibular ganglia suggests cross-species conservation of many structural features. However, it is important to note that although the prior art includes these reports of IPG-A and IPG-P activity in some biological fractions, the purification or characterisation of the agents responsible for the activity is not disclosed.

IPG-A substances are cyclitol-containing carbohydrates, also containing $Zn^{2+}$ ions and phosphate and having the properties of regulating lipogenic activity and inhibiting cAMP dependent protein kinase. They may also inhibit adenylate cyclase, be mitogenic when added to EGF-transfected fibroblasts in serum free medium, and stimulate lipogenesis in adipocytes.

IPG-P substances are cyclitol-containing carbohydrates, also containing $Mn^{2+}$ and/or $Zn^{2+}$ ions and phosphate and having the properties of regulating glycogen metabolism and activating pyruvate dehydrogenase phosphatase. They may also stimulate the activity of glycogen synthase phosphatase, be mitogenic when added to fibroblasts in serum free medium, and stimulate pyruvate dehydrogenase phosphatase.

Methods for obtaining A-type and P-type mediators are set out in Caro et al, 1997, and in WO98/11116 and WO98/11117, Protocols for determining characteristic IPG biological activities such as PDH activation, PKA inhibition, acetylCoA activation, fructose-1,6-bis-phosphatase activity and lipogenesis are well known in the art or provided in the experimental section below.

Drug Formulation

The compounds of the invention may be derivatised in various ways. As used herein "derivatives" of the compounds includes salts, coordination complexes with metal ions such as $Mn^{2+}$ and $Zn^{2+}$, esters such as in vivo hydrolysable esters, free acids or bases, hydrates, prodrugs or lipids, coupling partners.

Salts of the compounds of the invention are preferably physiologically well tolerated and non toxic. Many examples of salts are known to those skilled in the art. Compounds having acidic groups, such as phosphates or sulfates, can form salts with alkaline or alkaline earth metals such as Na, K, Mg and Ca, and with organic amines such as triethylamine and Tris (2-hydroxyethyl)amine. Salts can be formed between compounds with basic groups, e.g. amines, with inorganic acids such as hydrochloric acid, phosphoric acid or sulfuric acid, or organic acids such as acetic acid, citric acid, benzoic acid, fumaric acid, or tartaric acid. Compounds having both acidic and basic groups can form internal salts.

Esters can be formed between hydroxyl or carboxylic acid groups present in the compound and an appropriate carboxylic acid or alcohol reaction partner, using techniques well known in the art.

Derivatives which as prodrugs of the compounds are convertible in vivo or in vitro into one of the parent compounds. Typically, at least one of the biological activities of compound will be reduced in the prodrug form of the compound, and can be activated by conversion of the prodrug to release the compound or a metabolite of it. An example of prodrugs are glycolipid derivatives in which one or more lipid moieties are provided as substituents on the sugar residue or the cyclitol moieties, leading to the release of the free form of the compound by cleavage with a phospholipase enzyme. Examples of prodrugs include the use of protecting groups which may be removed in situ releasing active compound or serve to inhibit clearance of the drug in vivo Protecting groups are well known in the art and are discussed further below. An example of a suitable protecting group that might be used as a prodrug is the azido group used in the synthesis below, e.g. on the 2-position of the sugar moiety.

Other derivatives include coupling partners of the compounds in which the compounds is linked to a coupling partner, e.g. by being chemically coupled to the compound or physically associated with it. Examples of coupling partners include a label or reporter molecule, a supporting substrate, a carrier or transport molecule, an effector, a drug, an antibody or an inhibitor Coupling partners can be covalently linked to compounds of the invention via an appropriate functional group on the compound such as a hydroxyl group, a carboxyl group or an amino group. Other derivatives include formulating the compounds with liposomes.

Pharmaceutical Compositions

The compounds described herein or their derivatives can be formulated in pharmaceutical compositions, and administered to patients in a variety of forms, in particular to treat conditions which are ameliorated by the administration of inositol phosphoglycan second messengers or IPG antagonists such as competitive antagonist.

Pharmaceutical compositions for oral administration may be in tablet, capsule, powder or liquid form. A tablet may include a solid carrier such as gelatin or an adjuvant or an inert diluent. Liquid pharmaceutical compositions generally include a liquid carrier such as water, petroleum, animal or vegetable oils, mineral oil or synthetic oil. Physiological saline solution, or glycols such as ethylene glycol, propylene glycol or polyethylene glycol may be included. Such compositions and preparations generally contain at least 0.1 wt % of the compound.

Parental administration includes administration by the following routes; intravenous, cutaneous or subcutaneous, nasal, intramuscular, intraocular, transepithelial, intraperitoneal and topical (including dermal, ocular, rectal, nasal, inhalation and aerosol), and rectal systemic routes. For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, solutions of the compounds or a derivative thereof, e.g. in physiological saline, a dispersion prepared with glycerol, liquid polyethylene glycol or oils.

In addition to one or more of the compounds, optionally in combination with other active ingredient, the compositions can comprise one or more of a pharmaceutically acceptable excipient, carrier, buffer, stabiliser, isotonicizing agent, preservative or anti-oxidant or other materials well known to those skilled in the art. Such materials should be non-toxic and should not interfere with the efficacy of the active ingredient. The precise nature of the carrier or other material may depend on the route of administration, e.g. orally or parentally.

Liquid pharmaceutical compositions are typically formulated to have a pH between about 3.0 and 9.0, more preferably between about 4.5 and 8.5 and still more preferably between about 5.0 and 8.0. The pH of a composition can be maintained by the use of a buffer such as acetate, citrate, phosphate, succinate, Tris or histidine, typically employed in the range from about 1 mM to 50 mM. The pH of compositions can otherwise be adjusted by using physiologically acceptable acids or bases.

Preservatives are generally included in pharmaceutical compositions to retard microbial growth, extending the shelf life of the compositions and allowing multiple use packaging. Examples of preservatives include phenol, meta-cresol, benzyl alcohol, para-hydroxybenzoic acid and its esters, methyl paraben, propyl paraben, benzalconium chloride and benzethonium chloride. Preservatives are typically employed in the range of about 0.1 to 1.0% (w/v).

Preferably, the pharmaceutically compositions are given to an individual in a "prophylactically effective amount" or a "therapeutically effective amount" (as the case may be, although prophylaxis may be considered therapy), this being sufficient to show benefit to the individual. Typically, this will be to cause a therapeutically useful activity providing benefit to the individual. The actual amount of the compounds administered, and rate and time-course of administration, will depend on the nature and severity of the condition being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980. By way of example, and the compositions are preferably administered to patients in dosages of between about 0.01 and 100 mg of active compound per kg of body weight, and more preferably between about 0.5 and 10 mg/kg of body weight.

The composition may further comprise one or more other pharmaceutically active agents, either further compounds of the invention, inositol phosphoglycans, growth factors such as insulin, Nor or other growth factors listed below, or other drugs, e.g. those in use for the treatment of diabetes or other conditions set out below.

Medical Uses

As set out above, IPGs are second messengers for a range of different growth factors, including insulin, nerve growth factor, hepatocyte growth factor, insulin-like growth factor I (IGF-I), fibroblast growth factor, transforming growth factor β, the action of IL-2 on B-cells and T-cells, ACTH signalling of adrenocortical cells, IgE, FSH and hCG stimulation of granulosa cells, thyrotropin stimulation of thyroid cells, cell proliferation in the early developing ear and rat mammary gland. Consequently, IPGs or their antagonists can be used in the treatment or amelioration of disorders mediated by the growth factors or to mimic specific growth factor biological activities.

Examples of conditions which can be treated using IPGs or IPG antagonists include, diabetes, obesity, pre-eclampsia, neurotrophic disorders, hepatic damage and adrenal atrophy.

WO98/10791 discloses that pre-eclampsia is characterised by elevated levels of IPG-P and that it can be treated using an IPG-P antagonist. Compounds of the invention which are IPG-P antagonists, e.g. antagonists which compete with wild-type IPG-P but lack one or more of its activities, could be used in the treatment of pre-eclampsia.

The use of both IPG-P and IPG-A and IPG-A antagonists in the diagnosis and treatment of diabetes is disclosed in WO98/11435. This application discloses that in some forms of diabetes the ratio of P:A-type IPGs is imbalanced and can be corrected by administering a medicament containing an appropriate ratio of IPG-P, IPG-A or antagonist(s) thereof. In particular, it describes the treatment of obese type II diabetes (NIDDM) patients with a P-type IPG and/or an A-type IPG antagonist and the treatment of IDDM or lean type II diabetes (body mass index<27) with a mixture of P- and A-type IPGCS, typically in a P:A ratio of about 6:1 for males and 4:1 for females. The compounds and compositions of the present invention can be employed in such types of treatment. More particularly, the compounds are likely to be of use in the treatment of various form of diabetes and diabetic complications including diabetes due to insulin resistance, insulin resistance in type I diabetes and brittle diabetes, obese or lean type II diabetes, and of conditions associated with insulin resistance or insulin underproduction, such as neurotrophic disorders or polycystic ovary syndrome, lipodystrophy, age-related memory loss, and post-ischaemic damage secondary to stroke or post-transplant complications.

The compounds of this invention are also likely to be of use in controlling neuron proliferation or neurite outgrowth, either in vitro or in vivo, e.g. acting as a nerve or neurite growth factor mimetic second messenger. They may thus have applications in the treatment and/or diagnosis of any condition related to neuron proliferation or neurite differentiation. WO99/38516 discloses that IPG-A and synthetic mimetics thereof cause neuron proliferation, mimicking the action of the growth factor IGF-I. In contrast, IPG-P and synthetic mimetics thereof such as compound C4 cause neurite outgrowth. The neurons may be central (brain and spinal cord) neurons, peripheral (sympathetic, parasympathetic, sensory and enteric) neurons, or motor neurons. Treatments may involve the treatment of damage to nerve, spinal cord or central nervous system damage secondary to trauma, or autoimmune or metabolic damage, or post-ischaemic damage secondary to stroke or post-transplant complications, motor neuron disease, neurodegenerative disorders or neuropathy. Damage to the nervous system includes the results of trauma, stroke, surgery, infection (e.g. by viral agents), ischemia, metabolic disease, toxic agents, or a combination of these or similar causes. Motor neuron disease includes conditions involving spinal muscular atrophy, paralysis or amyotrophic lateral sclerosis. Neurodegenerative disorders include Parkinson's disease, Alzheimer's disease, epilepsy, multiple sclerosis, Huntingdon's chorea and Meniere's disease.

The compounds of the invention may also be useful as hepatocyte growth factor mimetic second messengers, e.g. in the preparation of medicaments for the treatment of hepatic damage caused by infection, alcohol abuse, drug sensitivity, or autoimmunity. The compounds may also be useful as fibroblast growth factor mimetic second messengers or epidermal growth factor mimetic second messengers, e.g. in the preparation of medicaments for the promotion of wound healing following surgery or trauma or tissue damage induced by ischaemia or autoimmunity.

In other embodiments, the compounds of the invention may be useful as adrenal cell growth factor mimetic second messengers or ACTH mimetic second messengers in the preparation of a medicament for the treatment of disease states involving adrenal atrophy.

Methods of Making the Compounds

Based on the disclosure herein, the knowledge in the art and in references[5-11], the skilled person could couple sugar residues and cyclitols together, optionally with one or more substituents. Examples of further compounds of the invention made by analogous syntheses include RGL1115, RGL1121, RGL1120, RGL1129, RGL1122, RGL1116 and RGL1117.

Useful guidance on the synthesis of the exemplified compounds and for introducing the substituents set out herein is provided by the papers by Gigg & Gigg, Khiar & Martin-Lomas[5] and Baeschlin et al[18] and the references cited therein.

Phosphoryl groups such as phosphate, cyclic phosphate or substituted phosphate or cyclic phosphate can be substituted into the compounds of the invention by the phosphate or phosphoramidite method, Bannwath et al, *Helvetica Chemica Acta*, 70:175–186, 1987 and Yu & Fraser-Reid, *Tetrahedron Lett.*, 29:979–982, 1988.

Phosphate protecting groups can also be synthesized according to the methods disclosed in Hoeben-Weyl, Methods of Organic Chemistry, volume 12/1 or 12/2, Teilheimer, Synthetic Methods of Organic Chemistry, Vol 45. Protecting groups for the OH of sugars include menthoxycarbonyl (MntCO), acetal (in particular, two R groups may together represent a bridging acetal such as O-cyclohexylidene, O-isopropylidene or O-benzylidene), tert-butyldimethylsilyl (TBDMS), benzyl (Bn), tert-butyldiphenylsilyl (TBDPS). Many protecting groups suitable for use in the syntheses and reactions of saccharides are known and are well documented in standard reference works. The choice depends in part on the route by which the compound is synthesised and/or on the uses to which it is to be put, including the reactions which it is subsequently intended to undergo.

Bioactivity Assays

The compounds of the invention can be tested for one or more the characteristic IPG-P and/or IPG-A activities mentioned above to determine whether they will be suitable for use a IPG mimetics or antagonists. Preferred assays measure the effect of the compounds on PDH phosphatase, PKA or lipogenesis. Protocols for these assays are provided in Caro et al[14].

EXAMPLES

General Methods

All reactions were run under an atmosphere of dry argon using oven-dried glassware and freshly distilled and dried solvents. THF and diethyl ether were distilled from sodium benzophenone ketyl. Dichloromethane and acetonitrile were distilled from calcium hydride. TLC was performed on Silica gel $GF_{254}$ (Merck) with detection by charring with phosphomolibdic acid/EtOH. For flash chromatography, Silica Gel (Merck 230–400 mesh) was used. Columns were eluted with positive air pressure. Chromatographic eluents are given as volume to volume ratios (v/v). Routine NMR spectra were recorded with Bruker Avance DPX300 ($^1$H, 300 MHz), Bruker Avance DRX400 ($^1$H, 400 MHz), and Bruker Avance DRX500 ($^1$H, 500 MHz) spectrometers. Chemical shifts are reported in ppm, and coupling constants are reported in Hz. Spectra were referenced to the residual proton or carbon signals of the solvent. High-resolution mass spectra were recorded on a Kratos MS-80RFA 241-MC apparatus. Optical rotations were determined with a Perkin-Elmer 341 polarimeter. Elemental analyses were performed using a Leco CHNS-932 apparatus. The organic extracts were dried over anhydrous sodium sulfate and concentrated in vacuo.

Myo-Inositol Containing Compounds

The synthesis of compounds RGL 1023, 1027 and 1029 involved the preparation of a glycosyl acceptor with position 6 free for reaction with the corresponding glycosyl donor.

Figure 2:
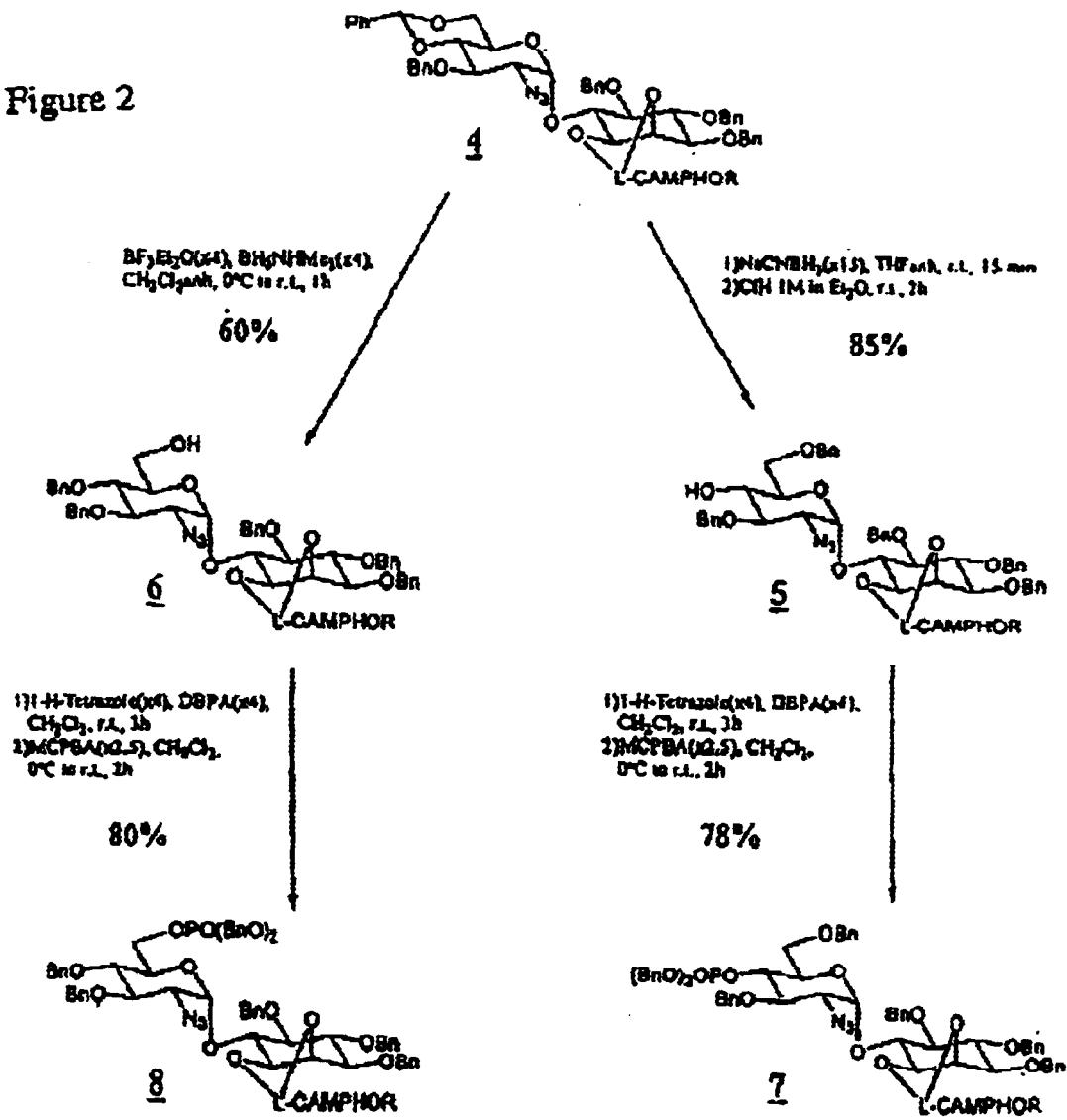
FIGS. 2A and 2B shows a reaction scheme for the production of compounds RGL1023 and RGL1027 from intermediate 4.
Figure 2A:
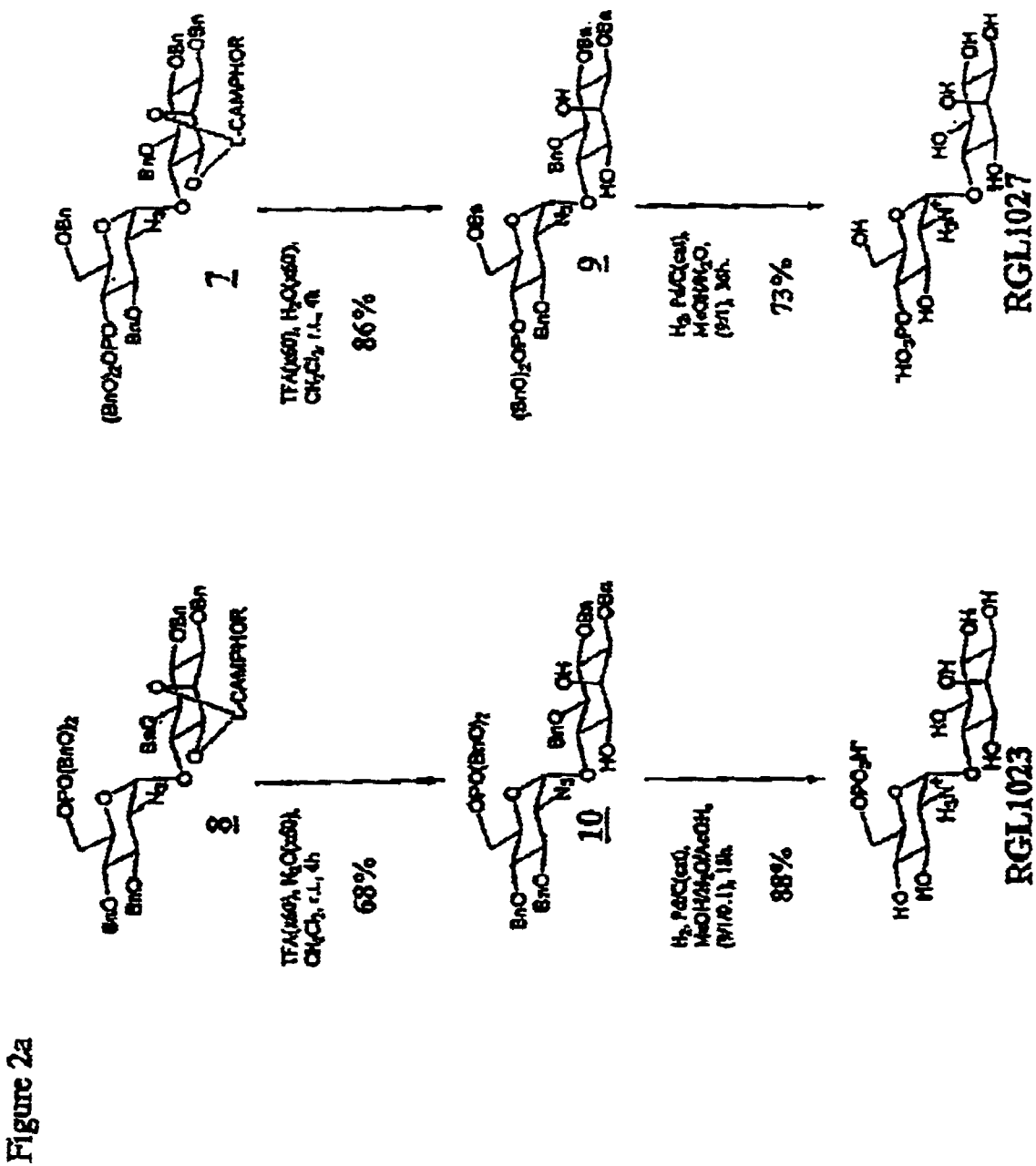

Diol 2 was chosen as the myo-inositol acceptor[17] as it can be regioselectively glycosylated at position 6. Regio- and stereoselective glycosylation of diol 2 is most conveniently performed using the trichloroacetimidate procedure with 2-azido-2deoxy glycosyl donors bearing protective group patterns compatible with the ftu-ther transforamtions required and designed as to provide an acceptable reactivity-selectivity balance in the forthcoming glycosylation reaction. Thus, use of trichloroacetimidate 1 was the glycosyl donor of choice. coupling of 1 with 2 in diethyl ether at $-20°$ C. using TMS triflate as promoter resulted in 6-O-glycosylation with good yield. Manipulation of protective groups afforded compound 4, a key intermediate for compounds RGL 1023 and RGL 1027 (FIG. 1). Selective opening of the benzylidene protecting group on positions 4' and 6' of the hexosamine residue afforded 5 and 6 in good yields. These compounds, precursors of phosphorylated species RGL 1023 and RGL 1027, were subjected to treatment with phosphorylating reagent dibenzyloxi(diisopropylamino) phosphine, which afforded the corresponding phosphite derivatives. Oxidation to the phosphate form was achieved in situ by reaction with MPBCA in dichloromethane at room temperature for two hours with good yield. Trifluoracetic acid treatment of compounds 7 and 8 in dichloromethane at room temperature for 4 hours a forded diols 9 and 10 with moderate to good yields. Compounds GL 1023 and RGL 1027 were obtained after hydrogenolytic debenzylation and concomitant azide reduction of 9 and 10 in buffered medium (FIGS. 2A and 2B).

Synthesis of compound RGL 1029 required that the glycosyl donor to be used contained a protecting group in position 3 different from a benzyl group, to be introduced later on in the glycosyl acceptor residue. Thus, trichloroacetimidate 11, bearing a p-methoxy-benzyl group in position 3 was used. Coupling with acceptor 2 in the conditions described above afforded compound 12 in good yield. Trifluoracetic acid hydrolysis and subsequent treatment with benzyl chloride in the presence of NaH in DMF afforded the benzylated derivative 13, which afforded precursor 14 in good yield after oxidative cleavage of the p-methoxy-benzyl group with 2,3-dichloro-5,6-dicyano-1,4-benzoquinone in dichloromethane.

Treatment of compound 14 with dibenzyl(diisopropyl) phosphoramidite followed by oxidation of the phosphite group afforded compound 15 (75%). Deprotection of the ketal group on the inositol moiety was achieved by acid hydrolysis to yield compound 16 (65%), which was then subjected to catalytic hydrogenolysis to produce RGL1029 quantitatively.

1'-D-6-O-(2'-azido-3'-O-benzyl-4',6'-O-benzylidene-2'-deoxy-α-D-glucopyranosyl)-1,2-O-(L-1,7,7-trimethyl[2.2.1]-bicyclohept-2-ylidene)-3,4-O-(1,1,3,3-tetraisopropyldisiloxanyl)-myo-inositol (3)

To a solution of trichloroacetimidate 2-azido-3-O-benzyl-4,6-O-benzylidene-2-deoxy-D-glucopyranoside 1 (1.698 g, 3 217 mmol) and 1-D-1,2-O-(L-1,7,7-trimethyl[2.2.1]-bicyclohept-2-ylidene)-3,4-O-(1,1,3,3-tetraisopropyldisiloxanyl)-myo-inositol 2 (2.51 g, 4.507 mmol) in $Et_2O$ (50 mL) at $-20°$ C., trimethylsilyl trifluromethanesulfonate (29 ml, 0.160 mmol) was added. The mixture was warmed to room temperature over 5 h, quenched by addition of $Et_3N$ (0.5 mL), filtered through celite and concentrated. The residue was purified by flash chromatography (Hexane/EtOAc 95/5 to 75/25) to give three disaccharides: α(1–6) 3 as a white solid (55% yield). 1'-D-6-O-(2'-azido-3'-O-benzyl-4',6'-O-benzylidene-2'-deoxy-α-D-glucopyranosyl)-1,2-O-(L-1,7,7-trimethyl [2.2.1]-bicyclohept-2-ylidene)-3,4,5-tri-O-benzyl-myo-inositol (4)

To a solution of disaccharide α(1–6) 3 (1.60 g, 1.735 mmol) in THF (20 mL) at 0° C., tetrabutyl ammonium fluoride was added (1 M solution in THF, 3.81 mL). After 15 min the solution was concentrated and the residue re-dissolved in DMF (15 mL). The solution was cooled to 0° C. and 60% sodium hydride in mineral oil (312 mg, 7.801 mmol) and benzyl bromide (0.93 mL, 7.801 mmol) was added. After 2 h methanol was added. The mixture was diluted with $CH_2Cl_2$ (100 mL), washed with sat. NaCl (2×100 mL), dried over $MgSO_4$ and concentrated. Flash chromatography of the crude (hexane/AcOEt 95/5) gave product 4 (1.410 g, 1.484 mmol, 85% over two steps).

1'-D-6-O-(2'-azido-3',6'-di-O-benzyl-2'-deoxy-α-D-glucopyranosyl)-1,2-O-(L-1,7,7-trimethyl[2.2.1]-bicyclohept-2-ylidene)-3,4,5-tri-O-benzyl-myo-inositol (5)

To a solution of disaccharide 4 (1.363 g, 1.431 mmol) in THF (40 mL) sodium cyanoborohydride (1 M solution in THF, 21.5 mL) was added. After 15 min at r.t. hydrochloric acid (1 M solution in ether) was added until evolution of hydrogen ceased. The mixture was stirred at r.t. for 2 h, diluted with $CH_2Cl_2$ (60 mL) and washed with sat. $NaHCO_3$ (2×100 ml). The aqueous layer was extracted with $CH_2Cl_2$ (2×50 mL) and the combined organic layer was dried over $MgSO_4$ and concentrated. Flash chromatography of the crude (hexane/AcOEt 9/1) gave the compound 5 (1.0 g, 1.050 mmol, 73%).

1'-D-6-O-(2'-azido-3',4'-di-O-benzyl-2'-deoxy-α-D-glucopyranosyl)-1,2-O-(L-1,7,7-trimethyl[2.2.1]-bicyclohept-2-ylidene)-3,4,5-tri-O-benzyl-myo-inositol (6)

To a solution of disaccharide 4 (460 mg, 0.484 mmol) and borane-dimethylamine complex (115 mg, 1.952 mmol) in $CH_2Cl_2$ (40 mL) at 0° C., boron trifluoride diethyl etherate (254 mL, 1.963 mmol) was added dropwise. After 30 min, the stirring was continued at r.t. for 1 hour, and then the reaction quenched with sat. $NaHCO_3$ (15 mL). The crude material was diluted with $CH_2Cl_2$ (60 mL), washed with sat. NaCl (3×100 mL), dried over $MgSO_4$ and concentrated. Flash chromatography of the crude (hexane/AcOEt 6/1) gave compound 6 (276 mg, 0.290 mmol, 60%).

1'-D-6-O-(2'-azido-3',6'-di-O-benzyl-2'-deoxy-4'-dibenzyl-phosphate-α-D-glucopyranosyl)-1,2-O-(L-1,7,7-trimethyl) [2.2.1]-bicyclohept-2-ylidene)-3,4,5-tri-O-benzyl-myo-inositol (7)

To a solution of disaccharide 5 (100 mg, 0.105 mmol) and 1-H-tetrazole (30 mg, 0.428 mmol) in anh. $CH_2Cl_2$(10 mL) at 0° C., dibenzyl diisipropylphosphoramidite (141 mL, 0.420 mmol) was added dropwise. After the addition was completed, the icebath was removed and the solution stirred for 2 h 30 min. The mixture was cooled to $-40°$ C. and a solution of 70% 3-chloroperbenzoic acid (65 mg, 0.264 mmol) in $CH_2Cl_2$ (4 mL) was added. The mixture was stirred for 2 h 30 min, diluted with $CH_2Cl_2$ (30 mL), washed with sat. $NaSO_3$ (2×50 mL), sat. $NaHCO_3$ (2×50 mL) and sat. NaCl (2×50 mL), dried over $MgSO_4$ and concentrated. Flash chromatography of the crude mixture (hexane/AcOEt 4/1) gave compound 7 (100 mg, 0.082 mmol, 78%).

1'-D-6-O-(2'-azido-3',4'-di-O-benzyl-2'-deoxy-6'-dibenzyl-phosphate-α-D-glucopyranosyl)-1,2-O-(L-1,7,7-trimethyl [2.2.1]-bicyclohept-2-ylidene)-3,4,5-tri-O-benzyl-myo-inositol (8)

To a solution of disaccharide 6 (150 mg, 0.157 mmol) and 1-H-tetrazole (44 mg, 0.628 mmol) in $CH_2Cl_2$(15 mL) at 0° C., dibenzyl diisipropylphosphoramidite (212 mL, 0.630 mmol) was added dropwise. After the addition was completed, the solution was stirred at r.t. for 3 h. The mixture was cooled to $-40°$ C. and a solution of 70% 3-chloroperbenzoic acid (97 mg, 0.393 mmol) in anh.

CH₂Cl₂ (5 mL) was added. The mixture was stirred for 45 min, diluted with CH₂Cl₂ (30 mL), washed with sat. NaHCO₃ (2×50 mL), sat. NaHCO₃ (2×50 mL) and sat. NaCl (2×50 mL), dried over MgSO₄ and concentrated. Flash chromatography of the crude mixture (hexane/AcOEt 4/1) gave compound 8 (152 mg, 0.125 mmol, 80%).

1'-D-6-O-(2'-azido-3',6'-di-O-benzyl-2'-deoxy-4'-dibenzylphosphate-α-D-glucopyranosyl)-3,4,5-tri-O-benzyl-myo-inositol (9)

To a solution of disaccharide 7 (100 mg, 0.082 mmol) in CH₂Cl₂ (10 mL) H₂O (0.09 mL, 5 mmol), and trifluoroacetic acid (0.38 mL, 4.949 mmol) were added and the reaction stirred for 4 h at r.t. The mixture was then diluted with CH₂Cl₂ (40 mL), washed with sat. NaHCO₃ (2×50 mL), sat. NaCl (3×50 mL), dried over MgSO₄ and concentrated. Flash chromatography of the crude mixture(hexane/AcOEt 1/1 to 1/2 and finally AcOEt 100%) gave compound 9 (60 mg, 0.056 mmol, 68%).

1'-D-6-O-(2'-azido-3',4'-di-O-benzyl-2'-deoxy-6'-dibenzylphosphate-α-D-glucopyranosyl)-3,4,5-tri-O-benzyl-myo-inositol (10)

To a solution of disaccharide 8 (110 mg, 0.091 mmol) in CH₂Cl₂ (10 mL) H₂O (0.1 mL, 5.551 mmol), and trifluoroacetic acid (0.42 mL, 5.470 mmol) were added and the reaction stirred for 4 h at r.t. The mixture was then diluted with CH₂Cl₂ (40 mL), washed with sat. NaHCO₃ (2×50 mL), sat. NaCl (3×50 mL), dried over MgSO₄ and concentrated. Flash chromatography of the crude mixture (hexane/AcOEt 1/1 to 1/2 and finally AcOEt 100%) gave compound 10 (84 mg, 0.078 mmol, 86%) as a white solid.

1'-D-6-O-(2'-amino-2'-deoxy-4'-phosphate-α-D-glucopyranosyl)-myo-inositol (RGL1027)

To a suspension of disaccharide 9 (16 mg, 14.840 mmol) in EtOH (0.6 mL) 10% Pd/C (3.2 mg, 0.003 mmol) was added and the reaction stirred under hydrogen atmosphere at r.t. for 36 h. The solvent was evaporated, the crude suspended in H₂O dest., filtered through celite and the filtrate lyophilized to give RGL1027 (4.6 mg, 10.919 mmol, 74%).
¹H NMR (D₂O, 500 MHz) δ 5.25 (broad s, 1H, H₁'), 3.96 (m, 1H, H₄'), 3.91 (m, 2H, H₃'+H₂), 3.84 (m, 1H, H₅'), 3.82 (m, 1H, H₆'ᵦ), 3.61 (m, 3H, H₆'ₐ+H₁+H₆), 3.52 (t, J=8.85 Hz, 1H, H₄), 3.41 (broad d, J=8.85 Hz, 1H, H₃), 3.27 (d, J=8.85 Hz, 1H, H₅), 3.18 (m, 1H, H₂'). ¹³C-NMR (D₂O, 500 MHz): d 97.40 (C₁'), 80.94 (C₆), 73.03 (C₅), 72.91 (C₄), 72.68 (C₂), 72.25 (C₅'), 72.08 (C₁), 71.99 (C₄'), 71.32 (C₃), 70.79 (C₃'), 60.36 (C₆'ₐ+C₆'ᵦ), 55.07 (C₂').

1'-D-6-O-(2'-amino-2'deoxy-6'-phosphate-α-D-glucopyranosyl)-myo-inositol (RGL1023)

To a suspension of disaccharide 10 (16 mg, 14.840 mmol) in a mixture MeOH/H₂O/AcOH 9/1/0.1 (0.5 mL) 10% Pd/C (3.2 mg, 0.003 mmol) was added, and the reaction stirred under hydrogen atmosphere at r.t. for 18 h. The crude was filtered through celite with an aqueous wash and the filtrate lyophilized to give RGL1023 (5.5 mg, 13.055 mmol, 88%).
¹H-NMR (D₂O, 500 MHz): δ 5.23 (broad s, 1H, H₁'), 4.00 (m, 1H, H₅'), 3.99 (m, 1H, H₆'), 3.90 (broad s, 1H, H₂), 3.78 (m, 1H, H₆'ᵦ), 3.73 (broad t, J=9.1 Hz, 1H, H₃'), 3.61 (m, 2H, H₁+H₆), 3.60 (m, 1H, H₄'), 3.53 (t, J=9.1 Hz, 1H, H₄), 3.40 (dd, J₁=2.3 Hz, J₂=9.1 Hz, 1H, H₃), 3.26 (broad t, J=8.9 Hz, 1H, H₅), 3.14 (m, 1H, H₂'). ¹³C-NMR (D₂O, 500 MHz): d 97.49 (C₁'), 81.14 (C₆), 73.69 (C₅), 72.90 (C₄), 72.72 (C₂), 72.69 (C₅'), 72.0 (C₁), 71.27 (C₃), 69.19 (C₄'-), 62.5 (C₆'ₐ+C₆'ᵦ), 56.65 (C₃'), 55.0 (C₂').

1'-D-6-O-(2'-azido-3'-O-(para)methoxybenzyl-4',6'-O-benzylidene-2'-deoxy-α-D-glucopyranosyl)-1,2-O-(L-1,7,7-trimethyl[2.2.1]-bicyclohept-2-ylidene)-3,4-O-(1,3,3-tetraisopropyldisiloxanyl)-myo-inositol (12)

To a solution of trichloroacetimidate 2-azido-3-O-(para)methoxybenzyl-4,6-O-benzylidene-2-deoxy-D-glucopyranoside 11 (166 mg, 0.298 mmol) and 1-D-1,2-O-(L-1,7,7-trimethyl[2.2.1]-bicyclohept-2-ylidene)-3,4-O-(1,3,3-tetraisopropyldisiloxanyl)-myo-inositol 2 (166 mg, 0.298 mmol) in Et₂O (3 mL) at r.t., trimethylsilyl trifluoromethanesulfonate (1 mL, 5.534 mmol) was added. After 20 minutes, the reaction was quenched by addition of Et₃N (0.1 mL), filtered through celite, concentrated and purified by flash chromatography (hexane/AcOEt 95/5) to give disaccharide 12 (171 mg, 0.180 mmol, 60%).

1'-D-6-O-(2'-azido-3'-O-paramethoxybenzyl-4',6'-O-benzylidene-2'-deoxy-α-D-glucopyranosyl)-1,2-O-(L-1,7,7-trimethyl[2.2.1]-bicyclohept-2-ylidene)-3,4,5-tri-O-benzyl-myo-inositol (13)

To a solution of disaccharide 12 (120 mg, 0.126 mmol) in THF (1.5 mL) at 0° C., tetrabutylammonium fluoride (1 M solution in THF, 284 mL) was added. The solution was warmed up to r.t. over 1 hour and then concentrated. The residue was re-dissolved in DMF (2 mL), cooled to 0° C. and 60% sodium hydride in mineral oil (23 mg, 0.575 mmol) and benzyl bromide (67 mL, 0.563 mmol) were added. After stirring at r.t. overnight under argon atmosphere, the excess of base was destroyed by addition of methanol, the mixture concentrated to dryness, diluted with CH₁Cl₂ (25 mL), washed with sat. NaCl (3×25 mL), dried over MgSO₄ and the solvent evaporated to dryness. Flash chromatography of the crude mixture (hexane/AcOEt 9:1) compound 13 (98 mg, 0.100 mmol, 79%).

1'-D-6-O-(2'-azido-4',6'-O-benzylidene-2'-deoxy-α-D-glucopyranosyl)-1,2-O-(L-1,7,7-trimethyl[2.2.1]-bicyclohept-2-ylidene)-3,4,5-tri-O-benzyl-myo-inositol (14)

To a solution of disaccharide 13 (120 mg, 0.122 mmol) in a CH₂Cl₂/H₂O 9/1 mixture (1.5 mL), 2,3-dichloro-5,6-dicyano-1,4-benzoquinone (35 mg, 0.154 mmol) was added, and stirred for 30 min at r.t. The reaction was diluted with CH₂Cl₂ (25 mL), filtered over celite, washed with sat. NaHCO₃ (2×25 mL), sat. NaCl (25 mL), dried over Na₂SO₄ and concentrated. Flash chromatography of the crude mixture (hexane/AcOEt 6/1) gave dissaccharide 14 (87 mg, 0.101 mmol, 83%).

1'-D-6-O-(2'-azido-4',6'-O-benzylidene3'-dibenzylphosphate-2'deoxy-α-D-glucopyranosyl)-1,2-O-(L-1,7,7-trimethyl[2.2.1]-bicyclohept-2-ylidene)-3,4,5-tri-O-benzyl-myo-inositol (15)

To a solution of disaccharide 14 (70 mg, 0.081 mmol) and 1-H-tetrazole (23 mg, 0.328 mmol) in CH₂Cl₂ (7 mL) at 0° C., dibenzyl diisipropylphosphoramidite (110 mL, 0.327 mmol) was added dropwise. After the addition, the solution stirred for 3 h at r.t. The mixture was then cooled to −40° C. and a solution of 70% 3-chloroperbenzoic acid (50 mg, 0.203 mmol) in CH₂Cl₂ (3 mL) was added. The mixture was stirred for 2 h 30 min, diluted with CH₂Cl₂ (40 mL), washed with sat. NaHSO₃ (2×50 mL), sat. NaHCO₃ (2×50 mL) and sat. NaCl (2×50 mL), dried over MgSO₄ and concentrated. Flash chromatography (hexane/AcOEt 4:1) gave compound 15 (68 mg, 0.061 mmol, 75%).

1'-D-6-O-(2'-azido-3'-dibenzyl-phosphate-2'-deoxy-α-D-glucopyranosyl)-3,4,5-tri-O-benzyl-myo-inositol (16)

To a solution of disaccharide 15 (30 mg, 0.027 mmol) in CH₂Cl₂(3 mL), H₂O (0.06 mL, 3.330 mmol) and trifluoroacetic acid (249 mL, 3.243 mmol) were added, and the reaction stirred for 18 h at r.t. The mixture was then diluted with CH₂Cl₂ (25 mL), washed with sat. NaHCO₃ (2×25 mL), sat. NaCl (3×25 mL), dried over MgSO₄ and concentrated. Flash chromatography (hexane/AcOEt ⅓ to AcOEt 100% and finally AcOEt/MeOH 9/1) gave compound 16 (16 mg, 0.018 mmol, 67%).

1'-D-6-O-(2'-amino-2'-deoxy-3'-phosphate-α-D-glucopyranosyl)-myo-inositol (RGL1029)

To a suspension of disaccharide 16 (8 mg, 8.910 mmol) in a mixture MeOH/H$_2$O 4/1 (0.3 mL), 10% Pd/C (2.1 mg, 0.002 mmol) was added and stirred under hydrogen atmosphere at r.t. for 18 h. The MeOH was evaporated, the crude suspended in dest. H$_2$O, filtered through celite and the filtrate lyophilized to give RGL1029 (3.6 mg, 8.545 mmol, 96%) as a white solid. $^1$H-NMR (D$_2$O, 500 MHz): δ 5.30 (broad s, 1H, H$_{1'}$), 4.22 (broad s, 1H, H$_3$), 3.97 (m, 1H, H$_{5'}$), 3.90 (broad s, 1H, H$_2$), 3.70 (m, 2H, H$_{6'}$+H$_{6'b}$), 3.66 (broad d, 1H, H$_1$), 3.60 (broad t, J=9.1 Hz, 1H, H$_6$), 3.54 (m, 1H, H$_{4'}$), 3.51 (t, J=9.1 Hz, H$_1$ H$_4$), 3.41 (dd, J$_1$=9.1 Hz, J$_2$=4.1 Hz, 1H, H$_3$), 3.31 (t, J=9.1 Hz, 1H, H$_5$), 3.25 (m, 1H, H$_{2'}$). $^{13}$C-NMR (D$_2$O, 500 MHz): d 97.20 (C$_{1'}$), 80.88 (C$_6$), 73.42 (C$_3$),72.88 (C$_5$), 72.82 (C$_4$), 72.76 (C$_2$), 72.0 (C$_{5'}$), 71.91 (C$_1$), 71.25 (C$_3$), 69.52 (C$_{4'}$), 60.25 (C$_{6'a}$+C$_{6'b}$), 54.59 (C$_{2'}$).

Chiro-Inositol Containing Compounds

Compound 3 was obtained when the glycosylation of 1 was carried out using a glycosyl donor such as 2 (FIG. 1). Deallylation of 3 using hydrogen activated [Ir(COD)(Ph$_2$MeP)$_2$] PF$_6$ catalytic isomerisation and subsequent NBS—H$_2$O promoted cleavage yielded 5 that was phosphorylated using the phosphoramidite procedure to give compound 6 in 87% yield. Hydrogenation of 6 in the presence of 10% palladium on charcoal gave 7 (RGL 1019) in quantitative yield.

Figure 3:
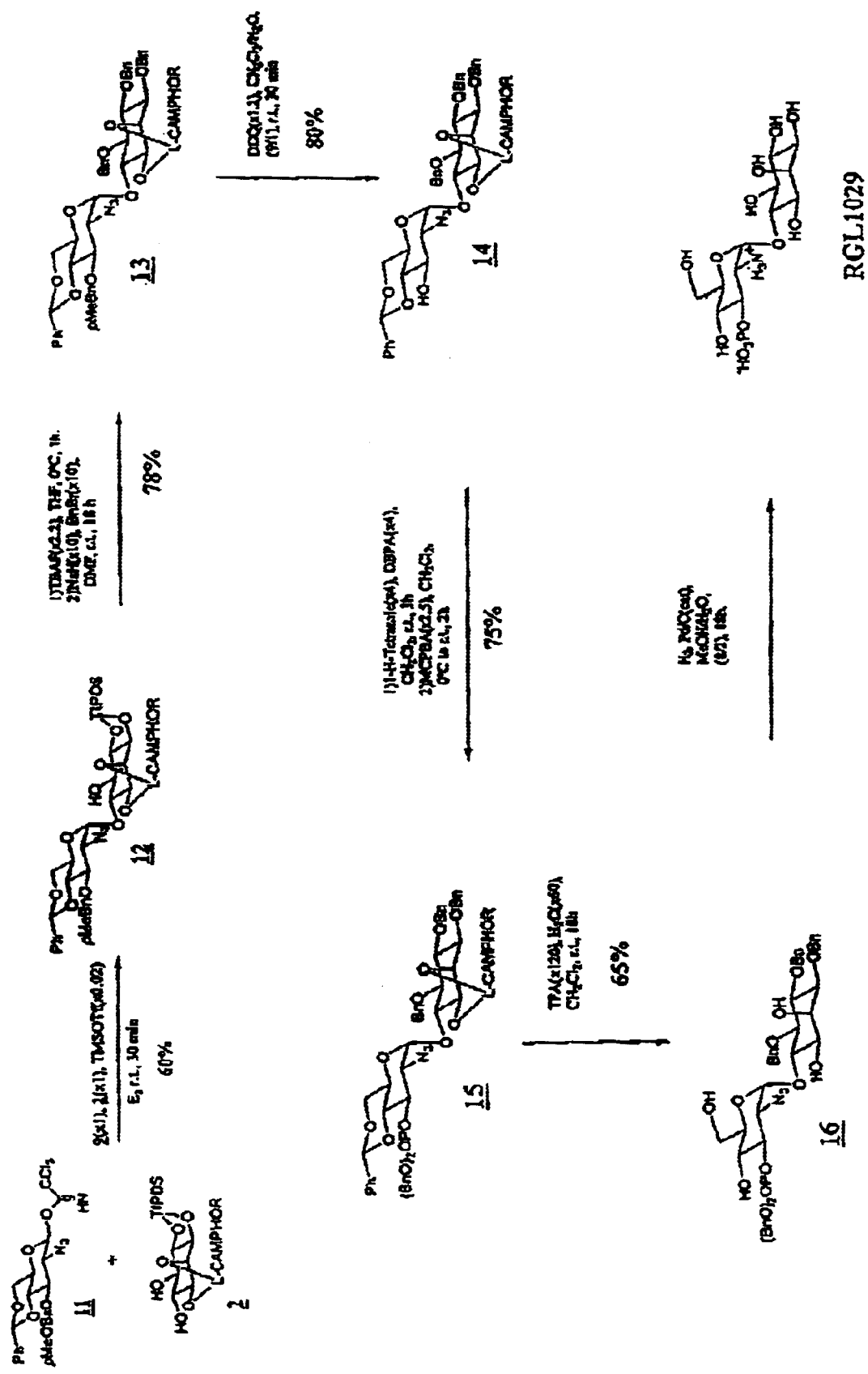
FIG. 3 shows a reaction scheme for the production of compound RGL1029 by coupling acceptor 2 with trichloroacetimidate 11.
Figure 4:
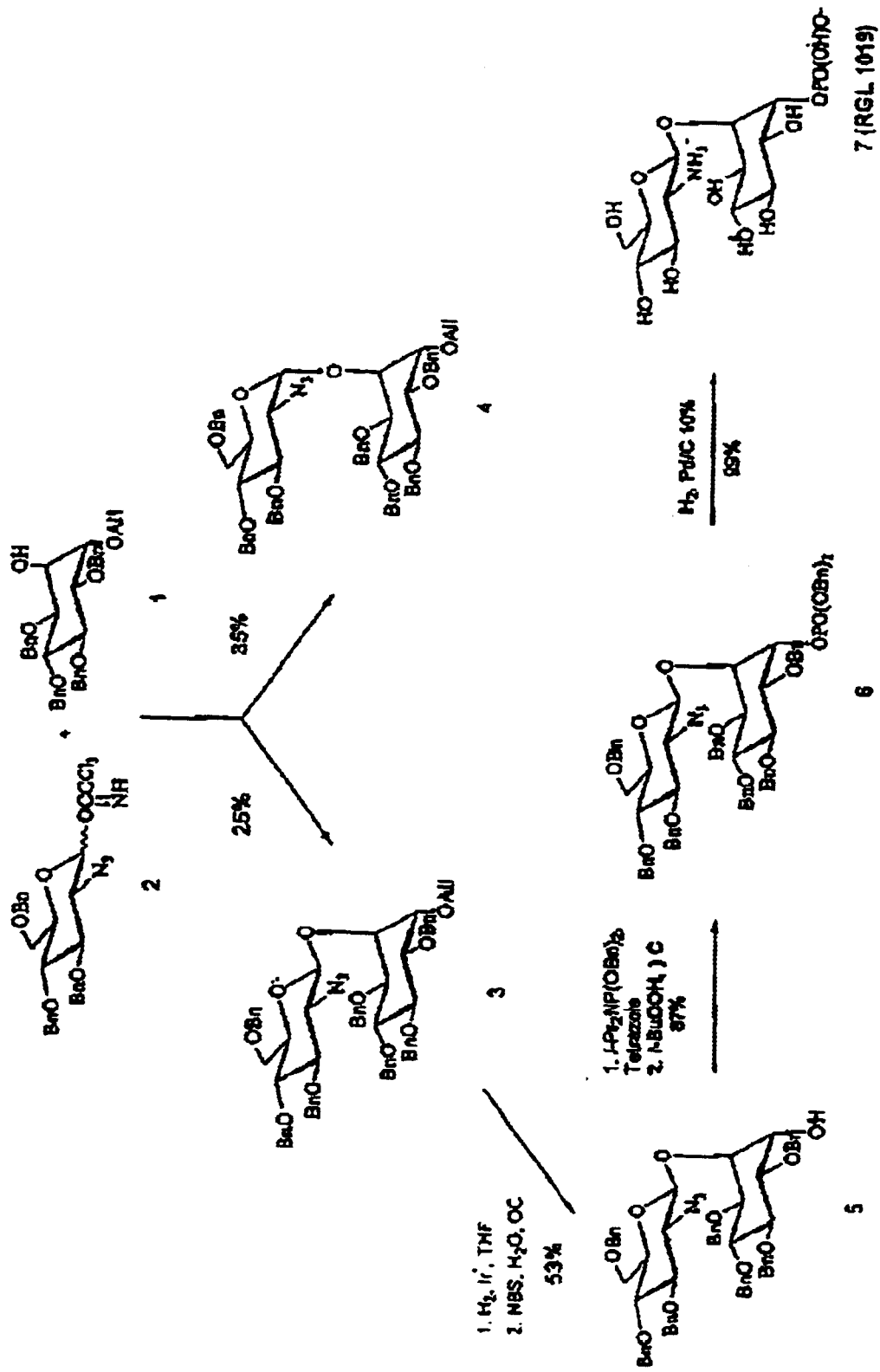
FIG. 4 shows a reaction scheme for the preparation of RGL1019.
Figure 5:
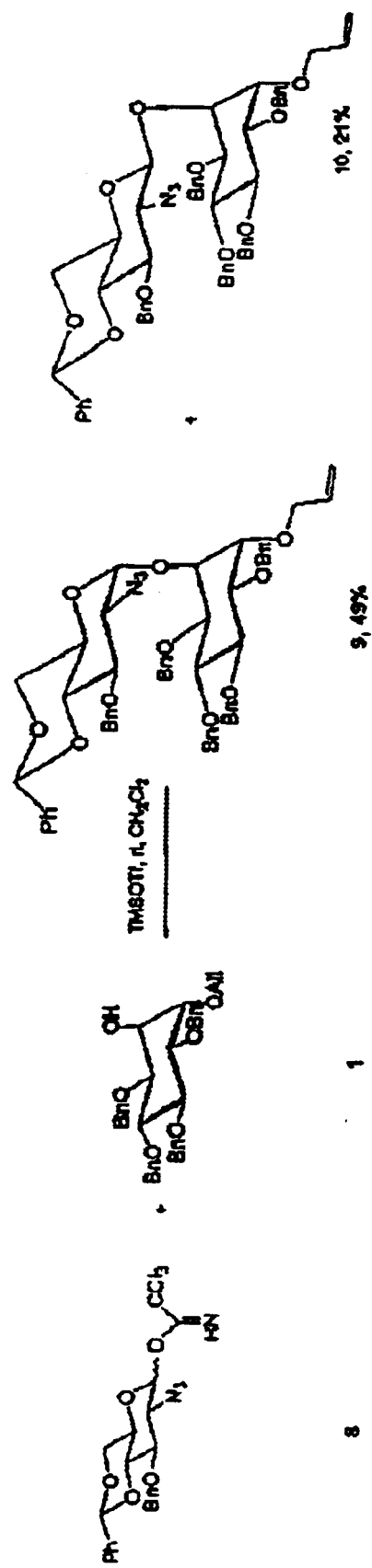
FIG. 5 shows a reaction scheme for the preparation of the precursors for RGL1017 and RGL1018, which are, shown in FIG. 6.
Figure 6:
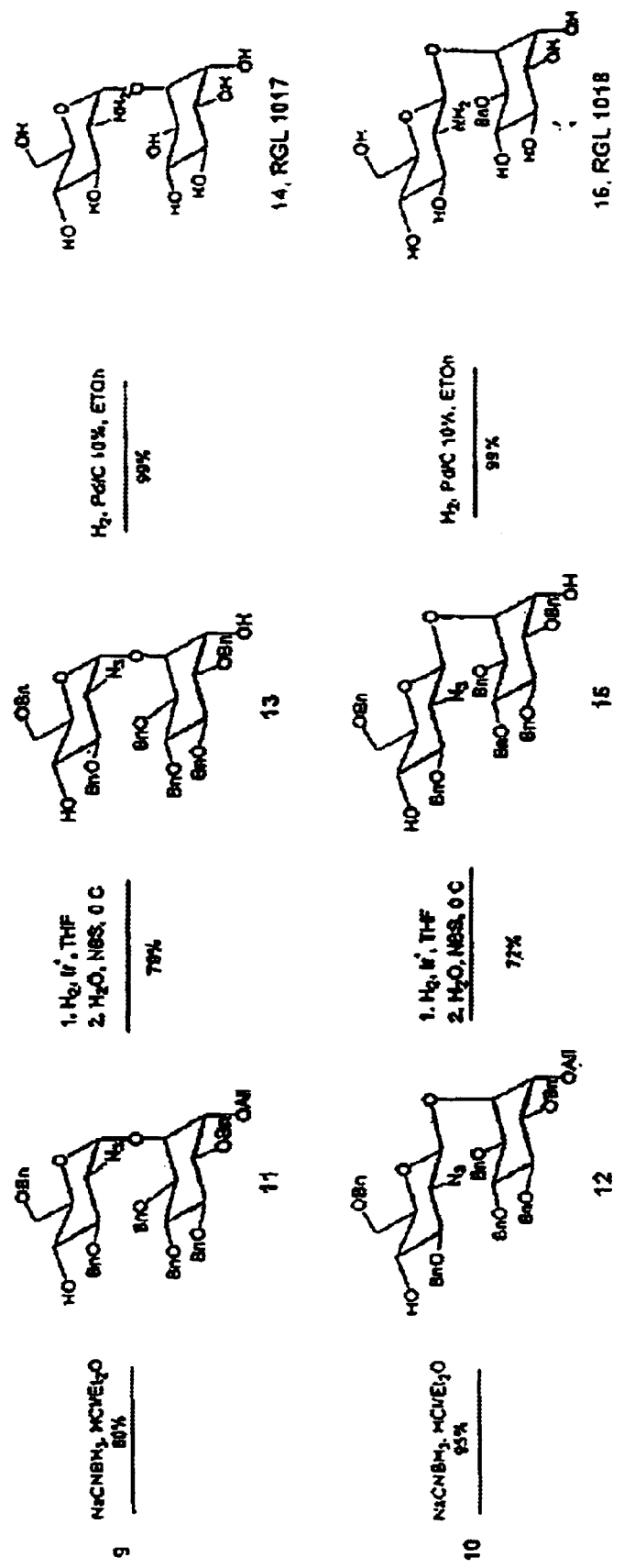
Figure 7:
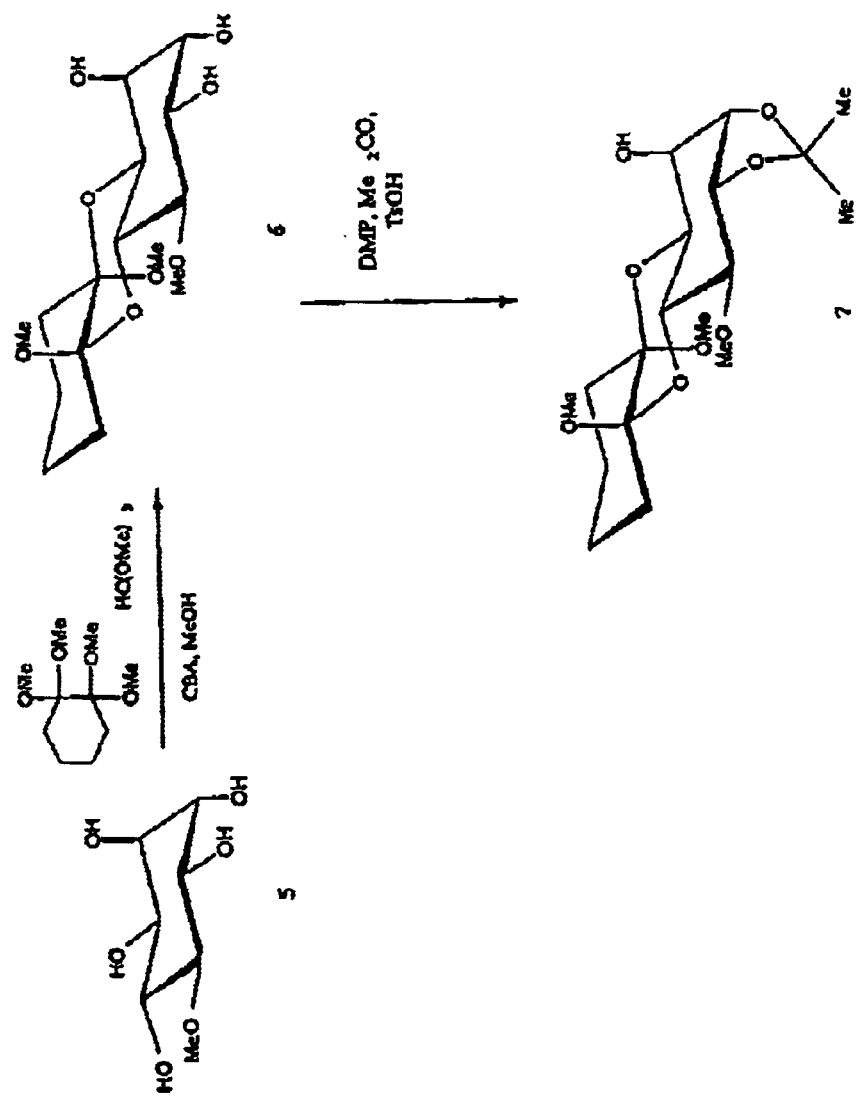
FIG. 7 shows the synthesis of building block 7 by bis-protection of the trans-diequatorially oriented hydroxyl groups of D-pinitol (5) as cyclohexane 1,2-diacetal and the cis-oriented hydroxyl groups as isopropylidene acetal.
Figure 8:
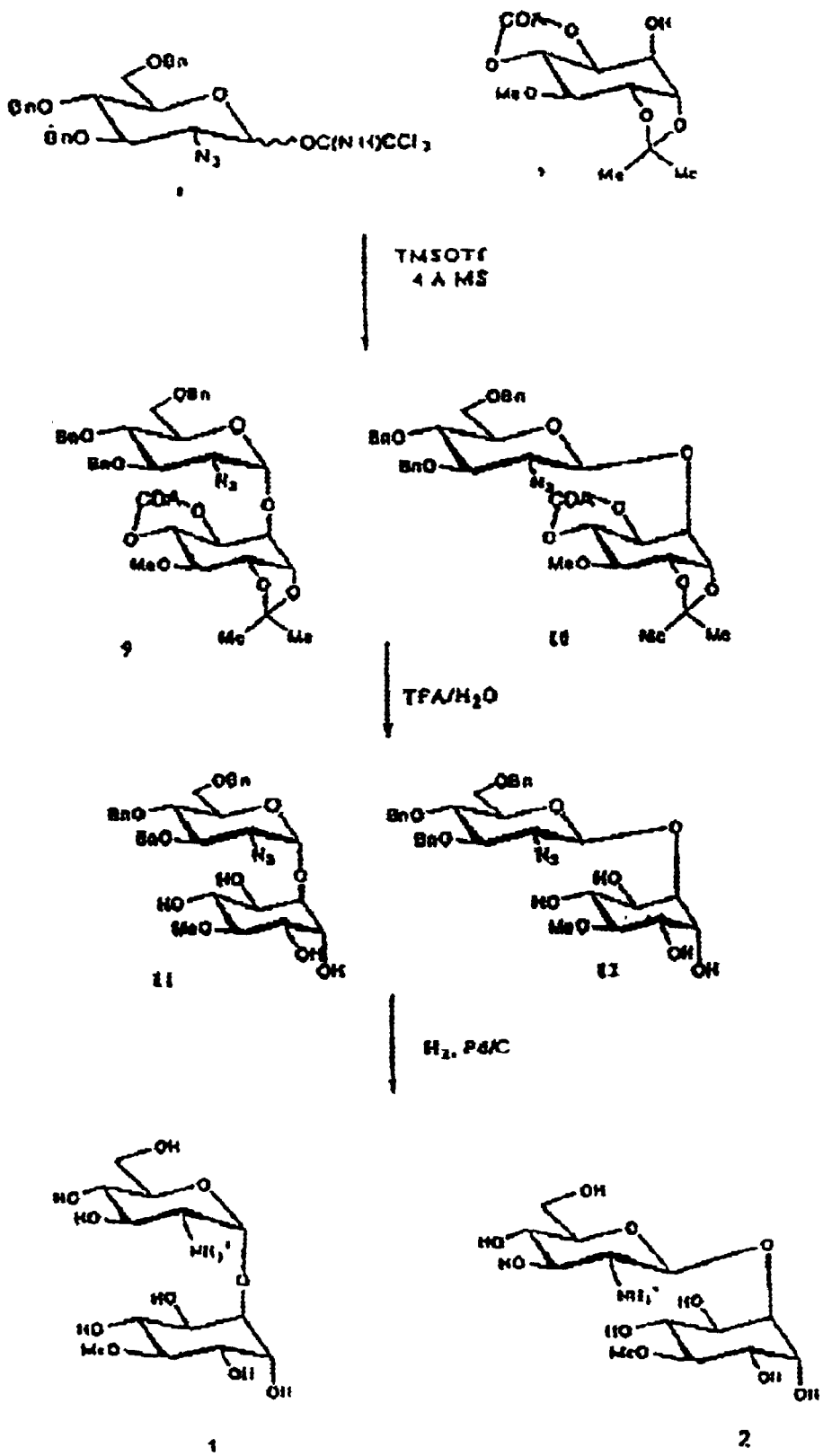
FIG. 8 shows the glycosylation of D-pinitol building block 7 with the 2-azido-2-deoxy-D-glucopyranosyl trichloroacetimidate 8 to give the IPG-like compounds 1 and 2.
Figure 9:
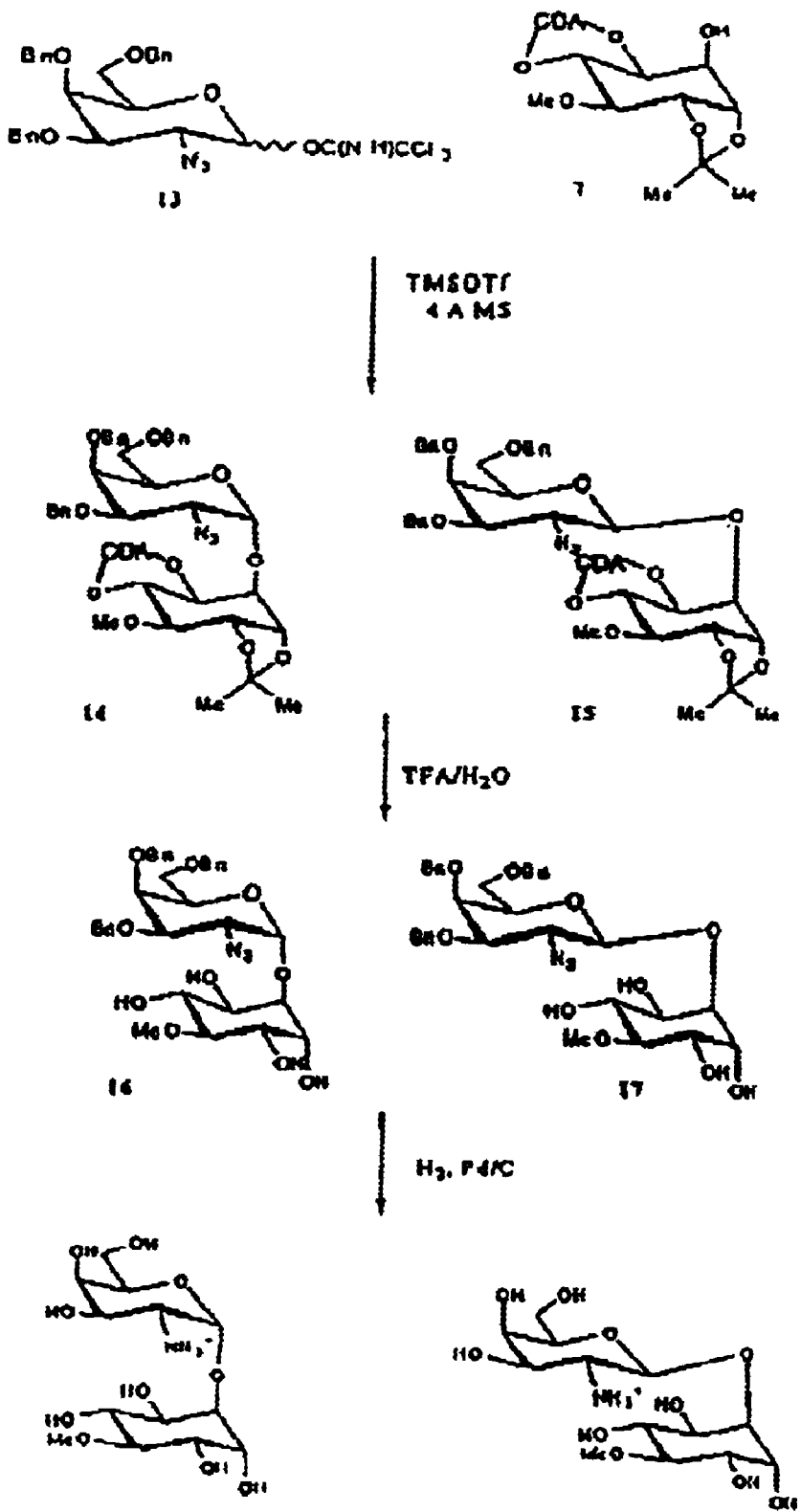
FIG. 9 shows the glycosylation of D-pinitol building block 7 with the 2-azido-2-deoxy-D-galactopyranosyl trichloroacetimidate 13 to give the TPG-like compounds 3 and 4.
Figure 10:
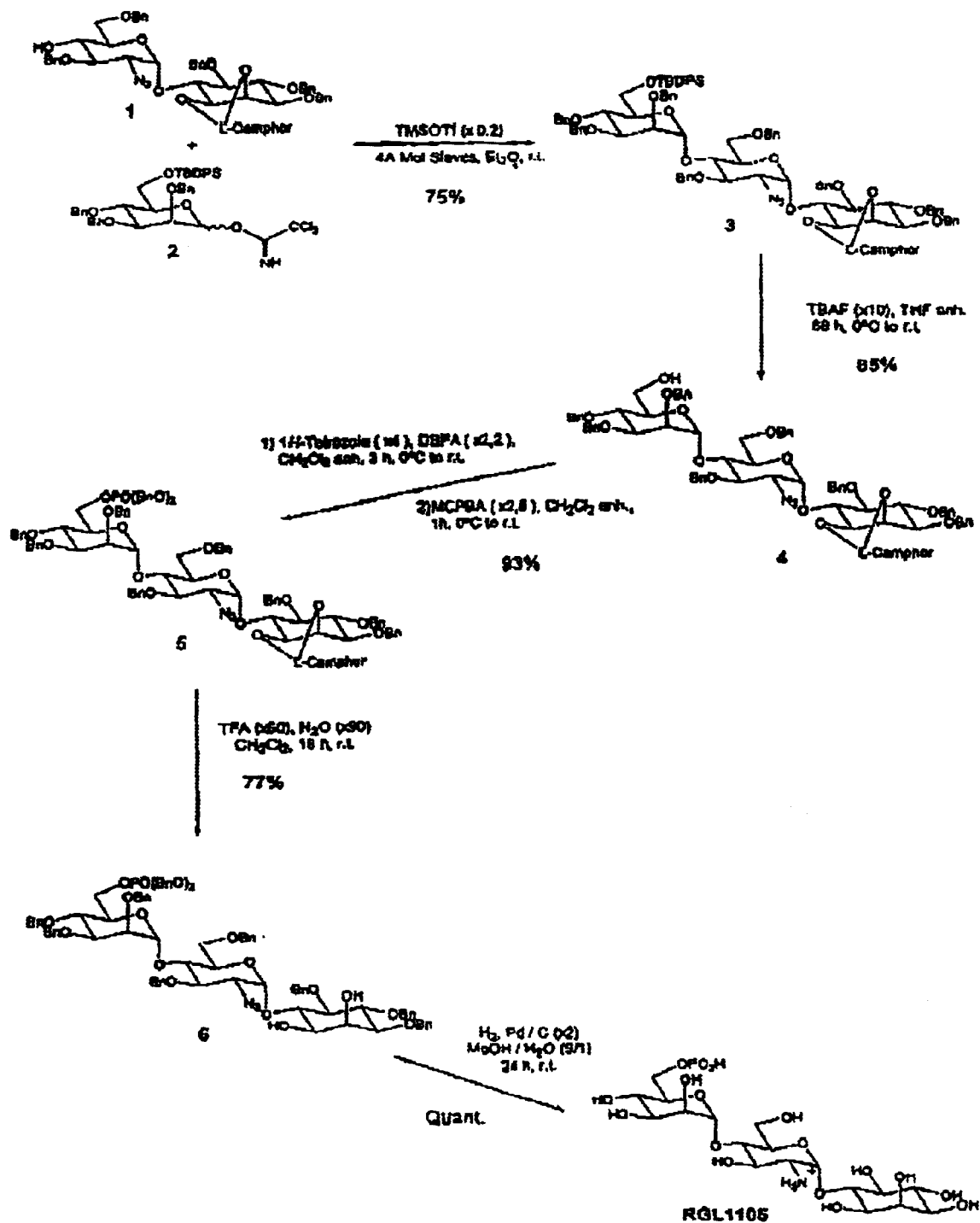
FIG. 10 shows the synthesis of RGL1105.
Figure 11:
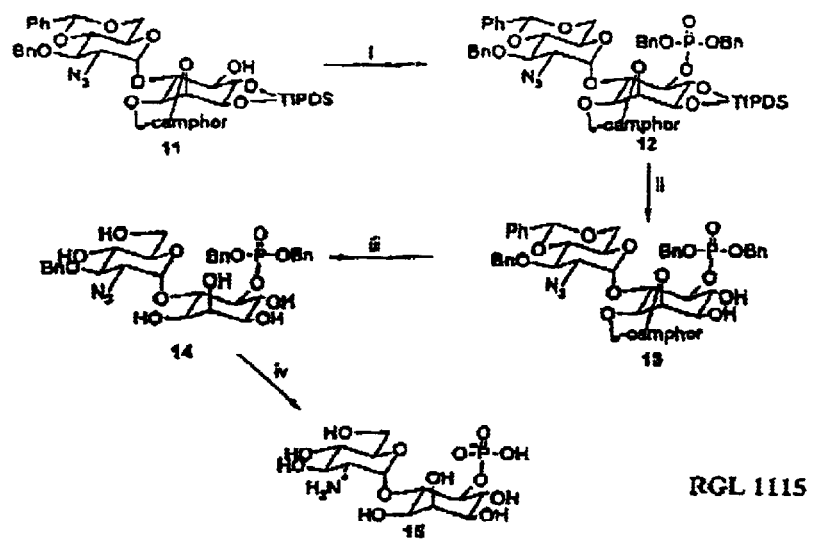
FIG. 11 shows the synthesis of RGL1115 an RGL1116.
Figure 12:
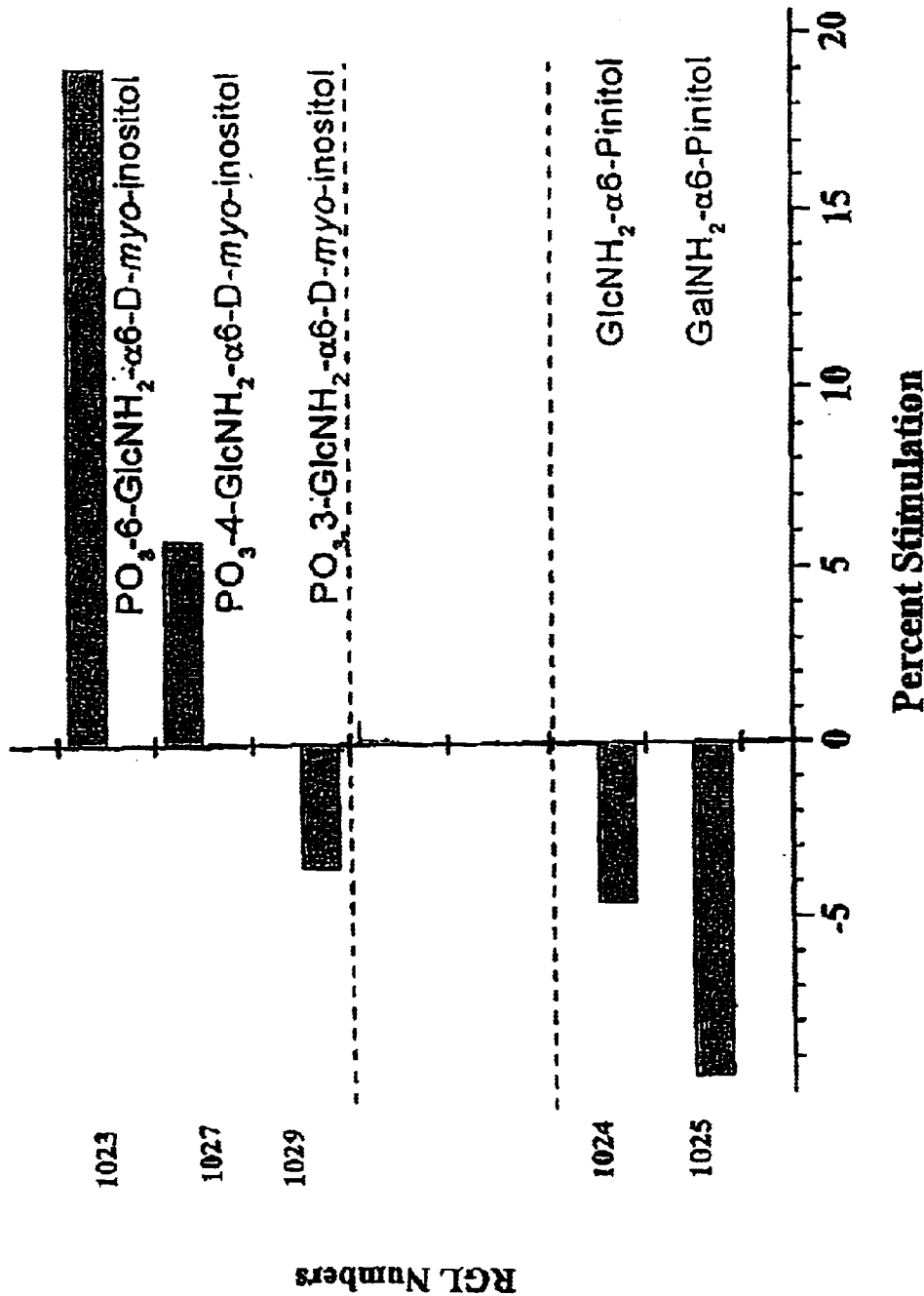
FIG. 12 shows a graph of basal lipogenesis stimulation of exemplary compounds of the invention.
Figure 13:
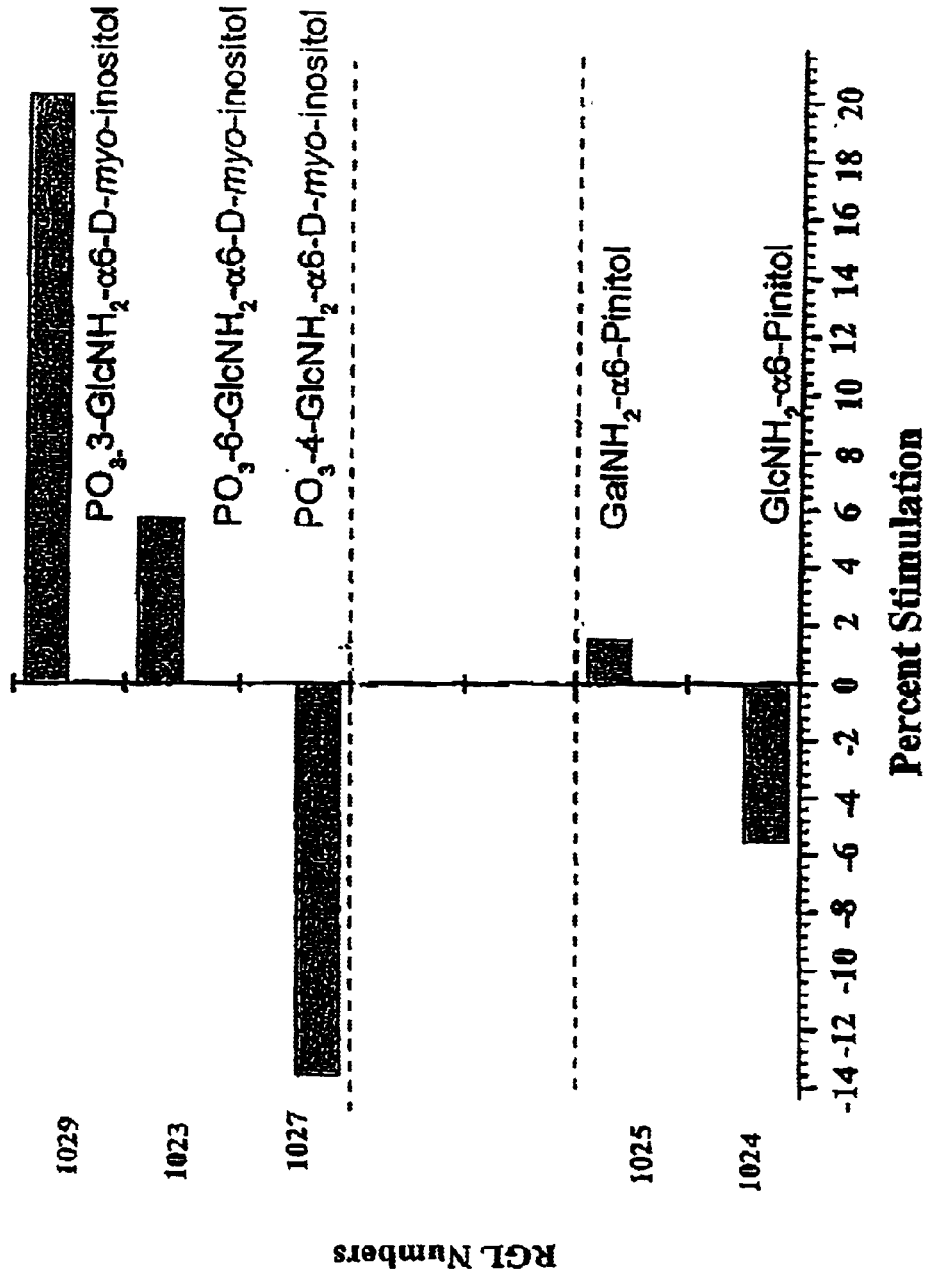
FIG. 13 shows a graph of glucose stimulated lipogenesis stimulation of exemplary compounds of the invention.
Figure 14:
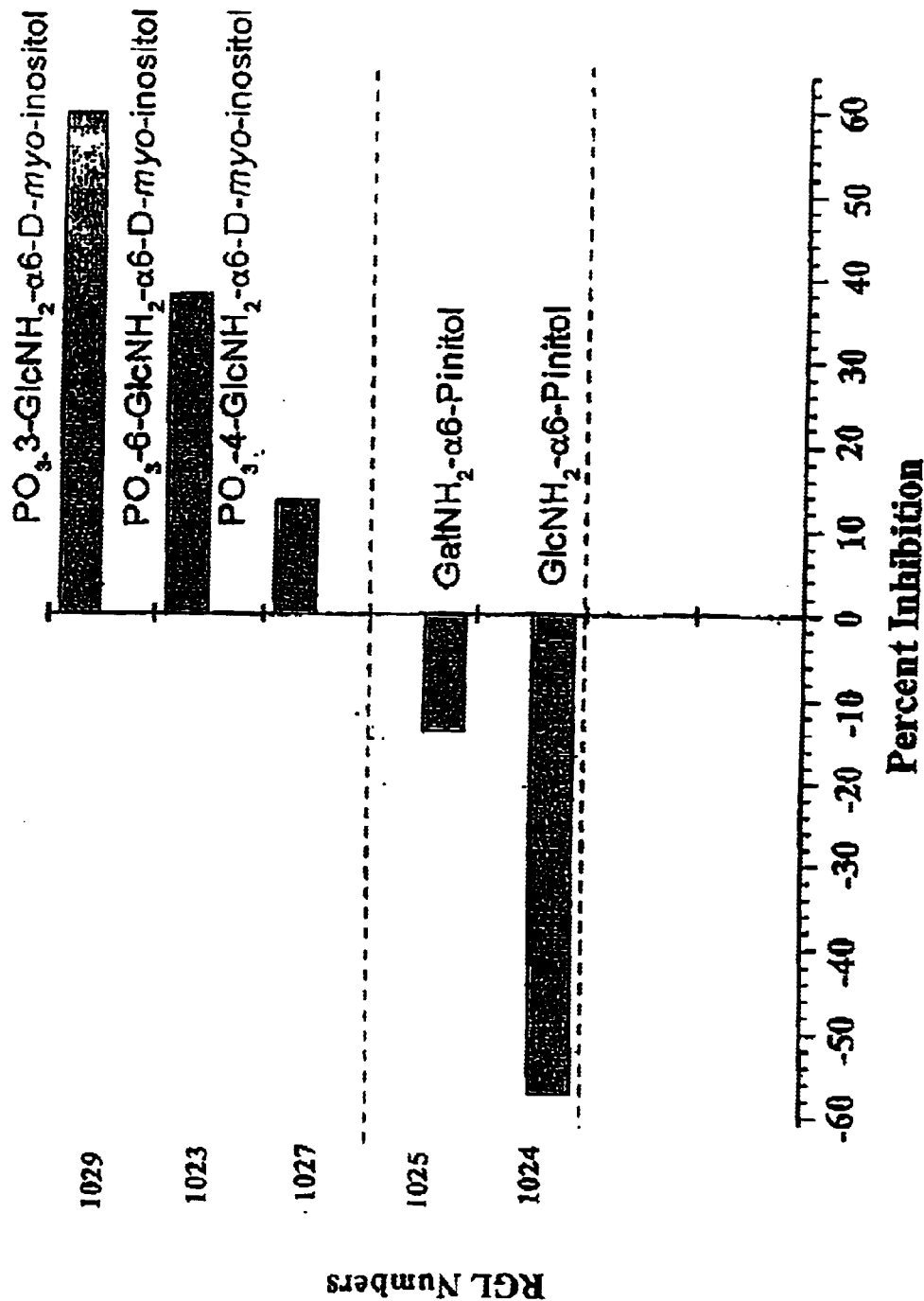
FIG. 14 shows a graph of the PKA inhibition of exemplary compounds of the invention.

The synthesis of D-chiro-inositol containing IPG like compounds bearing more complex oligosaccharide structures was envisaged using the trichloroacetimidate derivative 8 (FIGS. 2A and 2B) as glycosyl donor. Using this glycosyl donor, building blocks were also prepare to be used for the synthesis of pseudodisaccharides RGL 1017 and RGL1018 (FIG. 3).

Glycosylation of 1 with 8 afforded an α/β mixture of pseudodisaccharides 9 and 10 in 70% overall yield (FIGS. 2A and 2B). These compounds were separated and treated as indicated in Scheme 3. Selective reductive opening of the benzylidene acetals in 9 and 10 with NaBH$_3$CN—HCl afforded the partially protected derivatives 11 and 12 respectively in good yield. Deallylation of 11 gave 13 that after catalytic hydrogenation gave 14 in quantitative yield. A similar route from 12 yielded 16 (RGL1018) through 15.

6-O-Allyl-1-O-(3,4,6-tri-O-benzyl-2-azido-2-deoxy-β-D-glucopyranosyl)-2,3,4,5-tetra-O-benzyl-D-chiro-inositol (3) and 6-O-allyl-1-O-(3,4,6-tri-O-benzyl-2-azido-2-deoxy-α-D-glucopyranosyl),2,3,4,5-tetra-O-benzyl-D-chiro-inositol (4)

A mixture of compound 1 (73 mg, 0.125 mmol) and compound 2 (49 mg, 0.078 mmol) was coevaporated two times with toluene and then re-disolved in CH$_2$Cl$_2$ and treated with TMSOTf (0.1 M solution in CH$_2$Cl$_2$, 50 μL) at −25° C. After 30 min the reaction mixture was allowed to warm during 10 min., then quenched by addition of Et$_3$N and evaporated to dryness. The residue was purified by column chromatography [Hexane AcOEt (7:3→3.1)] to give 4 (35 mg, 35%) and 3 (25 mg, 25%) as syrups. Data for 3: $^1$H NMR (CDCl$_3$, 500 MHz): δ 3.29–3.38 (m, 3H, H-2', H-3', H-5'), 3.55 (t, 1H, J 9.2 Hz, H-4'), 3.63 (d, 2H, H-6'a, H-6'b), 3.79–3.86 (m, 3H), 3.88–3.95 (m, 3H, A11), 4.00 (t, 1H, J3.9, 3.1 Hz), 4.09–4.14 (m, 1H, A11), 4.45–4.55 (m, 4H, H-1', CH$_2$Ph), 4.60–4.68 (m, 3H, CH$_2$Ph), 4.76–4.92 (m, 8H, CH$_2$Ph), 5.05–5.16 (m, 2H, A11), 5.73–5.81 (m, 1H, A11), 7.14–7.38 (m, 35H, arH). HRFABMS: Calcd. for C$_{64}$H$_{67}$N$_3$O$_{10}$Na (M+Na$^+$) 1060.472416. Found 1060.476982.

Anal. Calcd. for C$_{64}$H$_{67}$N$_3$O$_{10}$: C, 74.04; H, 6.50; N, 4.05. Found: C, 73.54; H, 6.88; N, 4.10.

1-O-(2'-Azido-2-deoxy-3,4,6-tri-O-benzyl-β-D-glucopyranosyl)-2,3,4,5,-tetra-O-benzyl-D-chiro-inositol (5)

A solution of the indium catalyst in anhydrous THF (5.9×10$^{-3}$ M solution, 173 μL) previously treated under a hydrogen atmosphere for 30 minutes was added over a solution of 3 (35 mg, 0.034 mmol) in anhydrous THF (0.4 mL). The mixture was stirred at roon temperature for 1 h under Argon and then NBS (9 mg, 0.051 mmol) and distilled water (131 μL) were added and the mixture stirred again for 2 h, treated with a saturated solution of sodium hydrogen carbonate (0.3 mL). The reaction mixture was then extracted with AcOEt (2×10 mL), washed with saturated sodium chloride solution (2×20 mL), dried over Mg SO$_4$ and evaporated to dryness. The residue was purified by column chromatography (Hex6-AcOEt→Hex 4-AcOEt 1) to give pure 5 (30 mg, 88%) as a colourless oil. $^1$H NMR (CDCl$_3$, 500 MHz): δ 7.4–7.1 (m, 35H, ArH), 4.91–4.76 (m, 8H, AB System), 4.71–4.47 (m, 6H, AB System), 4.53 (d, J=7.0 Hz, 1H, H$_{1'}$), 4.29 (broad t, J=3.5 Hz, 1H, H$_1$), 4.22 (broad t, J=3.4 Hz, 1H, H$_6$), 4.0 (t, J=9.5 Hz, 1H, H$_4$), 3.92 (dd, J$_1$=2.8 Hz, J$_2$=9.9 Hz, 1H, H$_5$), 3.85 (dd, J$_1$=3.1 Hz, J$_2$=9.4 Hz, 1H, H$_2$), 3.76 (t, J=9.4 Hz, 1H, H$_3$), 3.66 (m, 2H, H$_{6'a}$+H$_{6'b}$), 3.60 (m, 1H, H$_{4'}$), 3.35 (m, H$_{2'}$+H$_{3'}$), 3.31 (dt, J$_1$3.1 Hz, J$_2$=9.8 Hz, 1H, H$_{5'}$), 2.44 (s, 1H, OH). $^{13}$C NMR(CDCl$_3$, 125 MHz): δ 139.04, 138.99, 138.92, 138.09, 137.95, 128.48, 128.47, 128.45, 128.44, 128.35, 128.30, 128.28, 128.17, 128.04, 127.95, 127.92 127.88, 127.84, 127.76, 127.74, 127.44, 127.30, 102.95 (C$_{1'}$), 82.95, 81.70, 81.30, 80.26, 79.56, 77.52, 76.29, 75.83, 75.76, 75.54, 75.04, 74.90, 73.53, 73.35, 73.07, 68.96, 68.56, 66.81.

6-O-(2-Azido-2-deoxy-3,4,6-tri-O-benzyl-β-D-glucopyranosyl)-2,3,4,5-tetra-O-benzyl-1-O-(dibenzyloxyphosphoryl)-D-chiro--inositol (6)

A solution of 5 (16 mg, 0.016 mmol) in a 1:1 mixture of dichloromethane-acetonitrile (0.4 mL) was treated with N, N-diisopropyl phosphoramidite (12 μL, 0.036 mmol) and tetrazole (5.1 mg, 0.072 mmol). The mixture was stirred at room temperature for 1.5 hr. and then treated with tert-butyl hydroperoxide (30 μL) and the stirring continued for 1 h. The solution was then evaporated to dryness and the residue was purified on column chromatography (Hex 7-AcOEt 2) to give 6 as colourless syrup (17.5 mg, 87%). $^1$H NMR (CDCl$_3$, 500 MHz): δ 7.37–7.10 (m, 45H, ArH), 5.19 (ddd, J$_1$=2.9 Hz, J$_2$=4.1 Hz, J$_3$=7.6 Hz, 1H, H$_1$), 4.73–4.93 (m, 12H, AB System), 4.66 (d, J=12.0 Hz, 1H, AB System), 4.54 (m, 4H, AB System), 4.42 (d, 1H, AB System), 4.39 (d, J=7.9 Hz, 1H, H$_{1'}$), 4.17 (broad t, J=3.7 Hz, 1H, H$_6$), 3.92 (m, 2H, H$_2$+H$_4$), 3.79 (dd, J$_1$=3.0 Hz, J$_2$=9.8 Hz, 1H, H$_5$), 3.73 (t, J=9.6 Hz, 1H, H$_3$), 3.71 (m, 1H, H$_{6'b}$), 3.67 (m, 1H, H$_{3'}$), 3.64 (dd, J$_1$=1.8 Hz, J$_2$=11.0 Hz, 1H, H$_{6'a}$), 3.36–3.29 (m, 3H, H$_{2'}$+H$_{4'}$+H$_{5'}$). $^{13}$C NMR (CDCl$_3$, 125 MHz): δ 138.90, 138.64, 138.09, 138.04, 137.98, 137.95, 135.93, 128.59, 128.50, 128.47, 128.43, 128.40, 128.39, 128.37, 128.34, 128.33, 128.29, 128.27, 128.25, 128.20, 128.14, 128.01, 127.99, 127.92, 127.90, 127.84, 127.75, 127.69, 127.62, 127.57, 127.49, 127.46, 127.42, 127.36, 103.32 (C$_{1'}$), 82.81 (C$_3$), 81.39, 80.92, 78.73, 78.21 (C$_2$, J$_{cp}$=42 Hz), 76.03 (C$_6$, J$_{cp}$=3.4 Hz), 75.76, 75.53, 75.07, 75.05, 74.10, 74.06 (C$_1$, J$_{cp}$=5.9 Hz), 73.70, 72.99, 72.67, 69.50 (POCH$_2$ Ar, J$_{cp}$=5.9 Hz), 69.11 (POCH$_2$ Ar, J$_{cp}$=5.9 Hz), 68.61 (C$_{6'}$), 66.76 (C$_{2'}$), $^{31}$P NMR(CDCl$_3$, 202 MHz):δ −2.31.

6-O-(2-Ammonio-2-deoxy-β-D-glucopyranosyl)-D-chiro--inositol-1-phosphate (7)

To a mixture of 6 (17.5 mg, 13.9 μm) in methanol (1.6 mL) and AcOH/AcONa buffer (1.6 mL) was added 10%

Pd/C (21.5 mg). The mixture was stirred under hydrogen for 24 h and then filtered over Celite, washed with a 1:1 mixture of EtOH/H$_2$O and liophylized. The residue was purified on Sephadex G-10 (10% aqueous EtOH) to afford pure 7 (RGL 1019) (5 mg, 100%). $^1$H NMR (D$_2$O, 500 MHz): δ 4.66 (d, J=8.2 Hz, 1Hz, 1H, H$_{1'}$), 4.58 (ddd, J$_1$=3.0 Hz, J$_2$=4.2 Hz, J$_3$=8.5 Hz, 1H, H$_1$), 4.19 (t, J=3.8 Hz, 1H, H$_6$), 3.93 (dd, J$_1$=9.3 Hz, J$_2$=3.3 Hz, 1H, H$_5$), 3.9 (dd, J$_1$=12.7 Hz, J$_2$=2.2 Hz, 1H, H$_{6'b}$), 3.71 (dd, J$_1$=12.7 Hz, J$_2$=5.7 Hz, 1H, H$_{6'a}$), 3.64 (m, 2H, H$_2$+H$_3$), 3.54 (t, J=9.4 Hz, 1H, H$_4$), 3.47 (ddd, J$_1$=2.2 Hz, J$_2$=5.6 Hz, J$_3$=9.6 Hz, 1H, H$_{5'}$), 3.45 (t, J=9.4 Hz, 1H, H$_{3'}$), 3.36 (t, J=9.6 Hz, 1H, H$_{4'}$), 2.77 (dd, J$_1$=9.4 Hz, J$_2$=8.2 Hz, 1H, H$_{2'}$). $^{31}$P NMR (D$_2$O, 202 MHz): δ 3.02.

1-O-(2-Azido-2-deoxy-3-O-benzyl-4,6-O-benzylidene-α- and -β-D-glucopyranosyl)-6-O-allyl-2,3,4,5-tetra-O-benzyl-D-chiro--inositol (9 and 10)

A mixture of 8 (520 mg, 0.985 mmol) and 1 (382 mg, 0.657 mmol) was dissolved in anhydrous CH$_2$Cl$_2$ (6.6 mL) and treated with a solution (2.50 μL) of trimethylsilyl triflate (80 μL) in CH$_2$Cl$_2$ (2 mL). The mixture was stirred at room temperature for 1.5 h and then 100 μL of the above solution of TMSOTf was added. After an additional hour with stirring (174 mg, 0.328 mmol) in CH$_2$Cl$_2$ (1.5 mL) was added and stirring was continued for 2 h. The mixture was the treated with Et$_3$N, evaporated to dryness and the residue fractionated on column chromatography (Hexane 8: AcoEt 1) to yield 9 (130.5 mg, 49%) and 10 (302 mg, 21%). Data for 9. $^1$H NMR (CDCl$_3$, 500 MHz): δ 7.47–7.21 (m, 30H, ArH), 5.79 (ddt, J$_1$=5.6 Hz, J$_2$=10.5 Hz, J$_3$=17.1 Hz, 1H, OCH$_2$CH=CH$_2$), 5.51 (s, 1H, CH benzyliden), 5.17 (dd, J$_1$=1.5 Hz, J$_2$=17.2 Hz, 1H, OCH$_2$CH=CHH), 5.13 (dd, J=1.5 Hz, J$_2$=10.4 Hz, 1H, OCH$_2$CH=CHH), 4.97–4.76 (m, 10H, AB System), 4.70 (d, J=3.8 Hz, 1H, H$_{1'}$), 4.25–4.17 (m, 2H, H$_5$+OCHHCH=CH$_2$), 3.99 (t, J$_1$=9.4 Hz, 1H, H$_3$), 3.97 (m, 1H, O—CH—H—CH=CH$_2$), 3.95 (m, 1H, H$_{6'cq}$), 3.97–3.74 (m, 6H, ChiroIns), 3.64 (t, J$_1$=9.3 Hz, 1H, H$_{4'}$), 3.56 (t, J=10.3 Hz, 1H, H$_{6'sk}$), 3.49 (dd, J$_1$=3.7 Hz, J$_2$=9.8 Hz, 1H, H$_{2'}$). Data for 10: $^1$H NMR (CDCl$_3$, 500 MHz): δ 7.49–7.20 (m, 30OH, ArH), 5.74 (ddt, J$_1$=5.6 Hz, J$_2$=10.4 Hz, J$_3$=17.4 Hz, 1H, OCH$_2$CH=CH,), 5.54 (s, 1H, CH benzyliden), 5.15 (broad dd, J$_1$=17.4 Hz, J$_2$=1.5 Hz, 1H, OCH$_2$CH=CHH), 5.11 (broad dd, J$_1$=10.4 Hz, J$_2$=1.5 Hz, 1H, OCH$_2$CH=CHH), 4.49–4.78 (m, 7H, AB System), 4.72 (d, J=11.7 Hz, 1H, AB System), 4.62 (d, J=11.7 Hz, 1H, AB System), 4.60 (d, J=11.7 Hz, 1H, AB System), 4.54 (d, J=8.1 Hz, 1H, H$_{1'}$), 4.21 (dd, J$_1$=5.1 Hz, J$_2$=10.4 Hz, 1H, H$_{6'cq}$), 4.13 (broad dd, J$_1$=5.6 Hz, J$_2$=13.0 Hz, 1H, OCHHCH=CH$_2$), 3.92–3.74 (m, 6H, ChiroIns), 3.7 (t, J=10.3 Hz, 1H, H$_{6'ax}$), 3.61 (t, J=9.3 Hz, 1H, H$_{4'}$), 3.46 (t, J=9.4 Hz, 1H, H$_3$), 3.28 (t, J=8.3 Hz, 1H, H$_{2'}$), 3.23 (dt, J$_1$=5.1 Hz, J$_2$=9.8 Hz, 1H, H$_{5'}$).

1-O-(2-Azido-2-deoxy-3,6-di-O-benzyl-α-D-glucopyranosyl)-6-O-allyl-2,3,4,5-tetra-O-benzyl-D-chiro--inositol (11)

To a solution of 9 (716 mg, 0.757 mmol) in THF (19 mL) 4Å molecular sieves were added and the mixture stirred for 30 min. Then a 1 M solution of sodium cyanoborohydride in THF (15 mL, 15.14 mmol) and a 1 M solution of HCl in ether was added until the evolution of gas ceased. The mixture was then treated with saturated aqueous solution of NaHCO$_3$ and the organic layer washed with saturated NaCl, dried over Na$_2$SO$_4$ and evaporated. The residue was purified by column chromatography (Hexane 4: AcoEt 1) to give 11 (575 mg, 80%). $^1$H NMR (CDCl$_3$, 500 MHz):δ 7.44–7.23 (m, 30H, Ar—H), 5.82 (ddt, J$_1$=5.6 Hz, J$_2$=10.4 Hz, J$_3$=17.2 Hz, 1H, OCH$_2$CH=CH$_2$), 5.21 (broad dd, J$_3$=1.6 Hz, J$_2$=17.2 Hz, 1H, OCH$_2$CH=CHH), 5.16 (broad dd, J$_1$=1.6 Hz, J$_2$=10.4 Hz, 1H, OCH$_2$CH=CHH), 4.96–4.65 m, 10H, AB System), 4.74 (d, J=3.6 Hz, 1H, H$_{1'}$), 4.44 (d, J=12.0 Hz, 1H, AB System), 4.32 (d, J=12.1 Hz, 1H, AB System), 4.22 (broad, dd, J$_3$=5.4 Hz, J$_2$=13.0 Hz, 1H, OCHHCH=CH$_2$), 4.12 (m, 1H, H$_{5'}$), 4.0 (m, 1H, OCHHCH=CH$_2$), 4.04–3.78 (m, 6H, ChiroIns), 3.76 (m, 2H, H$_3$+H$_{4'}$), 3.45 (dd, J$_1$=3.6 Hz, J$_2$=10.0 Hz, 1H, H$_{2'}$), 3.38 (dd, J$_1$=3.5 Hz, J$_2$=10.4 Hz, 1H, H$_{6'b}$), 3.27(dd, J$_1$=4.2 Hz, J$_2$=10.4 Hz, 1H, H$_{6'a}$), 2.39 (d, J=1.6Hz, 1H, OH$_{4'}$).

1-O-(2-Azido-2-deoxy-3,6di-O-benzyl-β-D-glucopyranosyl)6-O-allyl-2,3,4,5-tetra-O-benzyl-D-chiro--inositol (12)

A solution of 10 (290 mg, 0.307 mmol) in anhydrous THF (7.7 mL) was stirred with 4Å molecular sieves for 30 min. Then a 1 M solution of sodium cyanoborohydride in THF (5.6 mL) and 1 M solution of HCl in ether were added and the mixture stirred until evolution of gas ceased. The mixture was then treated with saturated aqueous NaHCO$_3$ and the organic layer washed with saturated aqueous NaCl, dried over Na$_2$SO$_4$ and evaporated. The residue was purified by column chromatography (Hexane 5: AcoEt 1) to give pure 12 (39.2 mg, 95%). $^1$H NMR (CDCl$_3$, 500 MHz):δ 7.41–7.21 (m, 30H, Ar—H), 5.76 (ddt, J$_1$=5.6 Hz, J$_2$=10.4 Hz, J$_3$=17.2 Hz, 1H, OCH$_2$CH=CH$_2$), 5.12 (dd, J$_1$=1.6 Hz, J$_2$=17.2 Hz, 1H, OCH$_2$CH=CHH, 5.04 (broad dd, J$_1$=1.6 Hz, J$_2$=10.3 Hz, 1H, OCH$_2$CH=CHH), 4.96–4.49 (m, 12H, AB System), 4.48 (d, J=8.0 Hz, 1H, H$_{1'}$), 4.11 (broad, dd, J$_1$=5.4 Hz, J$_2$=13.0 Hz, 1H, OCHHCH=CH$_2$), 3.99–3.78 (m, 6H, ChiroIns), 3.89 (m, 1H, OCHCH=CH$_2$), 3.67 (dd, J$_1$=4.0 Hz, J$_2$=10.3 Hz, 1H, H$_{6'b}$), 3.62 (dd, J$_1$=5.2 Hz, J$_2$=10.3 Hz, 1H, H$_{6'a}$), 3.51 (dt, J$_1$=2.3 Hz, J$_2$=9.6 Hz, 1H, H$_{4'}$), 3.29 (m, 1H, H$_{5'}$), 3.25 (t, J=8.0 Hz, H$_{2'}$), 3.16 (t, J$_1$=8.8 Hz, 1H, H$_{3'}$), 2.50 (d, J$_1$=2.3 Hz, 1H, OH$_{4'}$).

1-O-(2-Azido-2-deoxy-3,6-di-O-benzyl-α-D-glucopyranosyl)-2,3,4,5-tetra-O-benzyl-D-chiro--inositol (13)

A solution of the iridium catalyst in anhydrous THF (5.8×10$^{-3}$ M solution, 158 μl) previously treated under a hydrogen atmosphere for 30 minutes was added over a solution of 11 (29 mg, 0.030 mmol) in anhydrous THF (0.3 mL). The mixture was then stirred at room temperature for 45 minutes, and cooled to 0° C. NBS (7.7 mg, 0.043 mmol) and water (106 μL), and THF (1.75 mL) were added and the mixture was stirred for 15 min. and treated with a saturated solution of NaHCO$_3$. The mixture was extracted with CH$_2$Cl$_2$ and the organic layer dried over Na$_2$SO$_4$ and evaporated. The residue was purified by column chromatography (Hex 4:AcOEt 1→Hex 3:AcOEt 1) to give pure 13 (22 mg; 79%). $^1$H NMR (CDCl$_3$, 500 MHz): δ 7.41–7.19 (m, 30 H, ArH), 4.94–4.66 (m, 10H, AB System), 4.78 (d, J=3.6 Hz, 1H, H$_{1'}$), 4.37 (d, J=12.0 Hz, 1H, AB System), 4.25 (d, J=12.1 Hz, 1H, AB System), 4.14 (broad t, J=3.4 Hz, 1H, H$_6$), 4.08 (m, 1H, H$_{5'}$), 4.04 (broad t, J=3.6 Hz, 1H, H$_1$), 3.95 (dd, J$_1$=3.2 Hz, J$_2$=9.2 Hz, 1H, H$_2$), 3.86 (dd, J$_1$=2.7 Hz, J$_2$=9.5 Hz, 1H, H$_5$), 3.82 (t, J=9.1 Hz, 1H, H$_4$), 3.77 (t, J=9.1 Hz,1H, H$_3$),3.72 (m, 2H, H$_3$+H$_{4'}$), 3.42 (dd, J$_1$=3.6 Hz, J$_2$=10.0 Hz, 1H, H$_{2'}$), 3.28 (dd, J$_1$=3.4 Hz, J$_2$=10.3 Hz, 1H, H$_{6'b}$), 3.18 (dd, J$_1$=4.3 Hz, J$_2$=10.3 Hz, 1H, H$_{6'a}$),2.5 (s, 1H, OH$_1$), 2.41 (s, 1H, OH$_{4'}$). $^{13}$C NMR (CDCl$_3$,125 MHz):δ 138.83, 138.79, 138.53, 138.15, 138.10, 137.72, 128.57, 128.52, 128.42, 128.36, 128.34, 128.29, 128.19, 128.13, 128.10, 127.98, 127.96, 127.79, 127.71, 127.67, 127.52, 127.43, 127.36, 97.39 (C$_{1'}$), 81.74, 81.20, 80.00, 79.99, 78.38, 76.13, 75.76, 75.23, 73.52, 73.26, 72.99, 72.46, 70.03, 69.13, 67.25, 63.28.

1-O-(2-Azido-2-deoxy-3,6-di-O-benzyl-β-D-glucopyranosyl)-2,3,4,5-tetra-O-benzyl-D-chiro-inositol (15)

A solution of the iridium catalyst in anhydrous THF (5.8×10$^{-3}$, 178 µl) previously treated under a hydrogen atmosphere for 30 minutes was added over a solution 12 (32.7 mg, 0.034 mmol) in anhydrous THF (0.3 mL). The mixture was then stirred at room temperature for 45 minutes and cooled to 0° C. NBS (8.8 mg, 0.049 mmol) water (120 µl) and THF (2 ml) were added and the mixture stirred for 15 min. The reaction mixture was treated with saturated solution of NaHCO$_3$, extracted with CH$_2$Cl$_2$ and the organic layer dried and evaporated. The residue was purified by column chromatography (Hex 4; AcOEt 1→Hexane 3 AcOEt 1) to give pure 15 (22.5 mg, 72%). $^1$H NMR (CDCl$_3$, 500 MHz):δ 7.39–7.22 (m, 30 H, ArH), 4.93–4.50 (m, 12H, AB System), 4.53 (d, J=8.1 Hz, 1H, H$_{1'}$), 4.19 (m, 2H, H$_6$+H$_1$), 3.98 (t, J=9.4 Hz, 1H, H$_3$), 3.90 (dd, J$_1$=2.6 Hz, J$_2$=9.9 Hz, 1H, H$_2$), 3.80 (dd, J$_1$=2.8 Hz, J$_2$9.4 Hz, 1H, H$_5$), 3.75 (t, J=9.2 Hz, 1H, H$_4$), 3.65 (m, 2H, H$_{6'b}$+H$_{6'a}$), 3.54 (dt, J$_1$=2.2 Hz, J$_2$=9.2 Hz, 1H, H$_4$), 3.28 (m, 2H, H$_{2'}$+H$_{5'}$), 3.16 (t,J=9.2 Hz, 1H, H$_{3'}$), 2.54 (d, J=2.2 Hz, 1H, OH$_{4'}$), 2.43 (s, 1H, OH). $^{13}$C NMR (CDCl$_3$, 125 MHz):δ 139.02, 138.98, 138.93, 138.19, 138.09, 137.69, 128.64, 128.52, 128.44, 128.43, 128.35, 128.29, 128.27, 128.15, 128.12, 128.06, 127.90, 127.87, 127.86, 127.82, 127.67, 127.44, 127.42, 127.31, 102.98 (C$_1$), 82.29, 81.69, 81.29, 80.21, 79.56, 76.36, 75.82, 75.76, 75.11, 73.89, 73.71, 73.38, 73.11, 71.68, 70.01, 69.02, 66.20.

6-O-(2-Amino-2-deoxy-α-D-glucopyranosyl)-D-chiro--inositol (14, RGL 1017)

To a solution of 13 (8 mg, 0.009 mmol) in methanol (2 mL) was added 10% Pd/C (28 mg) and a drop of acetic acid. The mixture was stirred under hydrogen atmosphere for 8 h and then filtered over Celite and liophylized. The residue was purified using a Dowex 50 H$^+$ resin using methanol, water and 1% ammonium hydroxide to obtain pure 14 (RGL1017) (2.5 mg, 83%). $^1$H NMR (D$_2$O, 500 MHz):δ 5.0 (d, J=3.6 Hz, 1H, H$_1'$), 4.12 (t, J=3.6 Hz, 1H, H$_6$), 4.01 (t, J=3.6 Hz, 1H, H$_1$), 3.97 (ddd, J$_1$=2.5 Hz, J$_2$=4.5 Hz, J$_3$=9.6 Hz, 1H, H$_{5'}$), 3.82 (dd, J$_1$=3.6 Hz, J$_2$=9.6 Hz, 1H, H$_2$), 3.80 (m, 1H, H$_{6'b}$), 3.76 (m, 1H, H$_{6'a}$), 3.70 (dd, J$_1$=3.3 Hz, J$_2$=9.5 Hz, 1H, H$_5$),3.61 (t, J=9.7 Hz, 1H, H$_{3'}$), 3.59 (t, J=8.9 Hz, 1H, H$_3$), 3.55 (t, J=8.4 Hz, 1H, H$_4$), 3.40 (t, J=9.6 Hz, 1H, H$_{4'}$), 2.79 (dd, J$_1$=9.7 Hz, J$_2$=3.6 Hz, H$_{2'}$).

6-O-(2-Amino-2-deoxy-β-D-glucopyranosyl)-D-chiro-inositol (16, RGL 1018)

To a solution of 15 (4.5 mg, 0.004 mmol) in methanol (1.1 mL) 10% Pd/C (16 mg) and a drop of AcOH were added. The mixture was stirred for 8 h under a hydrogen atmosphere and the filtered over Celite, washed with methanol and liophylized. The residue was purified over a Dowex 50 H$^+$ column using methanol, water and 1% ammonium hydroxide to give pure 16 (RGL 1018) (1.6 mg, 100%). $^1$H NMR (D$_2$O, 500 MHz):δ 4.57 (d, J=8.2Hz, 1H, H$_{1'}$), 4.26 (t, J=3.6 Hz, 1H, H$_1$), 4.06 (t, J=3.6 Hz, 1H, H$_6$), 3.92 (dd, J$_1$=2.3 Hz, J$_2$12.4 Hz, 1H, H$_{6'b}$), 3.84 (dd, J$_1$=3.2 Hz, J$_2$=9.7 Hz, 1H, H$_5$), 3.77 (dd, J=3.2 Hz, J$_2$=9.5 Hz, 1H, H$_2$), 3.74 (dd, J$_1$=12.4 Hz, J$_2$=5.6 Hz, 1H, H$_{6'a}$), 3.62 (t, J=9.5 Hz, 1H, H$_{4'}$), 3.57 (t, J$_1$=9.5 Hz, 1H, H$_3$), 3.47 (m, 1H, $_{5'}$), 3.41 (t, J=9.5 Hz, 1H, H$_{3'}$), 3.37 (t, J=9.3 Hz, 1H, H$_{4'}$), 2.71 (t, J=8.8 Hz, 1H, H$_{2'}$).

Pinitol Containing Compounds

The synthesis of compounds 14 involved the preparation of a glycosyl acceptor with position 6 differentiated to be reactive with the corresponding glycosyl donor. Protection of the pinitol unit as cyclohexane-1,2-diacetal as proposed by Ley[8] was attempted. The selectivity of the reaction of 5 with 1,1,2,2-tetramethoxycyclohexane arises from the stabilising influence of the four anomeric effects in the resulting acetal 6 and the equatorial arrangement of all four sterically demanding alkyl substituents of the central 1,4-dioxane unit (FIG. 1). Treatment of 6 with 2,2-dimethoxypropane in the presence of TsOH gave 7 in 80% yield.

Glycosylation of 7 with 2-azido-2-deoxy-3,4,6-tri-O-benzyl-D-glucopyratisol-trichloroacetimidate 8[9] prepared following a well established procedure[10,6b], in dichloromethane and using TMSOTf as promoter[11] gave a 2:1 mixture of the α (9) and β (10) linked pseudodisaccharides in 54% yield (FIGS. 2A and 2B). The acetal groups were removed[12] to give 11 and 12 respectively which were subjected to hydrogenolysis to afford finally 1 and 2 in quantitative yield.

Glycosylation of 7 with 2-azido-2-deoxy-3,4,6-tri-O-benzyl-D-galactopyranose (13) under different conditions gave a mixture of α- and β-linked pseudodisaccharides 14 and 15 in moderate yield (FIG. 3). Removal of the acetal groups and subsequent hydrogenolysis afforded 3 and 4.

4,5-O-(1',2'-dimethoxycyclohexane-1',2'-diyl)-3-O-methyl-D-chiro-inositol (6)

3-O-methyl-D-chiro-inositol (D-pinitol) (283 mg, 1.457 mmol, 1 equiv) was dissolved in methanol (15 mL), then 1,2-cyclohexane diacetal (507 mg, 2.458 mmol, 1.7 equiv), trimethyl orthoformiate (200 mL, 1.752 mmol, 1.2 equiv) and 1-(S)-(+)-10-camphorsulfonic acid (24 mg, 0.102 mmol, 0.07 equiv) were added. The reaction mixture was heated at 70° C. for 24 h whereupon it was diluted with MeOH and quenched with solid NaHCO$_3$. The residue was concentrated and purified by flash chromatography (Hex/EtOAc 1:15) to give 6 (222 mg, 0.664 mmol, 45%; 89% based on 134 mg of recovered D-pinitol). R$_f$(Hex/EtOAc 1:20):0.22; [α]$^{20}_D$ −22.9 (c=1.05, CHCl$_3$); $^1$H NMR (CDCl$_3$, 300 MHz): d=4.12 (Ys, 1H, H$_1$), 4.10 (s, 2H, H$_4$, H$_5$), 4.07 (Ys, 1H, H$_6$), 3.81 (dt, 1H, J$_{2-3}$=9.0 Hz, J$_{2-1}$=3.6 Hz, J$_{2-OH}$=1.8 Hz, H$_2$), 3.47 (t, 1H, J=9.0 Hz, H$_3$), 3.23 (s, 3H, OCH$_3$), 3.21 (s, 3H, OCH$_3$), 2.76 (d, 1H,J$_{OH-2}$=1.8 Hz, OH$_2$), 2.60 (s, 1H, OH$_1$), 2.56 (s, 1H, OH$_{-6}$), 1.86–1.78 (m, 1H, CDA), 1.77–1.66 (m, 3H, CDA), 1.57–1.50 (m, 2H, CDA), 1.42–1.34 (m, 2H, CDA); $^{13}$C-NMR (CDCl$_3$, 75 MHz); d=98.9 (C), 98.0 (C), 80.2 (C$_3$), 71.5(C$_2$), 70.8, 70.4, 70.3 (C$_1$, C$_4$, C$_6$), 68.7 (C$_5$), 61.1 (OCH$_3$), 47.0(OCH$_3$, CDA), 46.8 (OCH$_3$, CDA), 27.1 (CH$_2$), 27.0 (CH$_2$), 21.5 (CH$_2$), 21.4 (CH$_2$); HRFABMS Calcd. for C$_{15}$H$_{26}$O$_8$: 357.3571 found: 357.1528; MALDI-TOF Calcd. for C$_{15}$H$_2$O$_8$+Na$^+$: 357.4. found: 357.5. calcd. for C$_{15}$H$_{26}$O$_8$+K$^+$: 373.5. found: 374.1

4,5-O-(1',2'-dimethoxycyclohexane-1',2'-diyl)-3-O-methyl-1,2-O-isopropyliden-D-chiro-inositol (7)

4,5-O-(1',2'-dimethoxycyclohexane-1',2'-diyl)-3-O-methyl-D-chiro-inositol (6) (326 mg, 0.975 mmol, 1 equiv) and 2,2-dimethoxypropane (1,321 mL, 1.072 mmol, 1.1 equiv) in acetone (4 mL) were treated with p-toluenesulfonic acid monohydrate (9.3 mg, 0.049 mmol, 0.05 equiv). The reaction was stirred for 1 h, whereupon it was quenched with solid NaHCO$_3$, the solvent evaporated and the residue purified by flash chromatography (Hex/AcOEt 1:1) to give 7 (292 mg, 0.873 mmol, 81%) as a white solid. R$_f$(Hex/EtOAc 3:1): 0.71; [α]$^{20}_D$ −18.0 (c=0.30, CHCl$_3$); $^1$H NMR (CDCl$_3$, 500 MHz): d=4.27 (dd, 1H, J$_{1-2}$=7.3 Hz, J$_{1-6}$=3.2 Hz, H$_1$), 4.24 (t, 1H, J=3.2 Hz, H$_6$), 4.16 (t, 1H, J=7.3 Hz, H$_2$), 4.06 (t, 1H, J=10.2 Hz, H$_4$), 3.94 (dd, 1H, J$_{5-6}$=10.2 Hz, J$_{5-6}$=3.2 Hz, H$_5$), 3.61 (s, 3H, OCH$_3$), 3.39 (dd, 1H, J$_{3-4}$=10.2 Hz, J$_{3-2}$=7.3 Hz, H$_3$), 3.23 (s, 3H, OCH$_3$, CDA), 3.22 (s, 3H, OCH$_3$, CDA), 1.86–1.78 (m, 1H, CDA), 1.77–1.66 (m, 3H, CDA),1.52 (s, 3H, CH$_3$), 1.57–1.51 (m, 2H, CDA), 1.36 (s, 3H, CH$_3$),1.41–1.33 (m, 2H, CDA); $^{13}$C-NMR (CDCl$_3$, 125 MHz): d=109.0 (C), 98.4 (C, CDA), 97.8 (C, CDA), 82.7 (C$_3$), 79.6 (C$_2$), 76.4 (C$_1$), 68.5 (C$_5$), 68.3 (C$_6$), 67,4($C_4$), 60.2 ($OCH_3$), 47.1 ($OCH_3$, CDA), 46.9 ($OCH_3$, CDA), 27.0 ($CH_3$), 27.1 ($CH_2$), 26.9 ($CH_2$), 26.0 ($CU_3$); 21.4 (2$CH_2$); Anal. Calcd. for $C_{18}H_{30}O_8$:C, 57.74%; H, 8.08%. found: 57.46%; H, 7.86%; HRFABMS Calcd. for $C_{18}H_{30}O_8$+$Na^+$: 397.1838. found: 397.1854; MALDI-TOF Calcd. for $C_{18}H_{30}O_8$+$Na^+$: 397.4. found: 397.3 calcd. for $C_{18}H_{30}O_8$+$K^+$, 413.5. found: 413.8.

Glycosylation reaction of 7 and 8

To a solution of 8 (809 mg, 1.305 mmol, 1.5 equiv) in $CH_2Cl_2$ (4 mL), compound 7 (295 mg, 0.788 mmol, 1equiv) and freshly activated 4Å molecular sieves were added and the mixture stirred for 1 h under Argon. Then, TMSOTf (12.6 mL, 0.104 mmol, 0.08 equiv) was added and the reaction mixture stirred for 24 h. The suspension was filtered through celite and the solvent evaporated under vacuum to provide a mixture of two disaccharides (α/β=2:1) which can be separated by flash chromatography (Hex/EtOAc 4:1) to obtain 9 (235 mg, 0.282 mmol, 36%) and 10 (118 mg, 0.142 mmol, 18%).

2-Azido-2-deoxy-3,4,6-tri-O-benzyl-D-glucopyranosyl-α (1−6)-4,5-O-(1',2'-dimethoxycyclohexane-1',2'-diyl)-1,2-O-isopropyliden-3-O-methyl-D-chiro-inositol (9)

Rf (Hex/EtOAc 3:1): 0.17; $[\alpha]^{20}_D$+48.8° (c=0.25, $CHCl_3$); $^1$H NMR ($CDCl_3$, 500 MHz): d=7.43–7.22 (m, 15H, Ph), 4.94 (d, 1H, $J_{1'-2'}$=3.2 Hz, $H_{1'}$), 4.83 (d, 1H, J=13.0 Hz, CHPh), 4.82 (AB syst., 2H, $CH_2$Ph), 4.58 (d, 1H, J=12.0 Hz, CHPh), 4.58 (m, 1H, $H_{5'}$), 4.57 (d, 1H, J=13.0 Hz, CHPh), 4.42 (d, 1H, J=12.0 Hz, CHPh), 4.25 (t, 1H, J=6.4 Hz, $H_2$), 4.18 (t, 1H, J=2.5 Hz, $H_1$), 4.16(t, 1H, J=2.5 Hz, $H_6$), 4.11 (t, 1H, J=10.5 Hz, $H_4$), 3.96 (t, 1H, J=10.1 Hz, $H_3$'), 3.90 (dd, 1H, $J_{5-4}$=10.5 Hz, $J_{5-6}$=2.5 Hz, $H_5$), 3.79 (t, 1H, J=10.1 Hz, $H_{4'}$), 3.71 (dd, 1H, $J_{6'1-6b'}$=10.8 Hz, $J_{6a'-5'}$=2.4 Hz, $H_{6a'}$), 3.60 (s, 3H, $OCH_3$), 3.59 (dd, 1H, $J_{6a'-6b'}$=10.8 Hz, $J_{6b'-5'}$=1.6 Hz, $H_{6b'}$), 3.41 (dd, 1H, $J_{3-4}$=10.5 Hz, $J_{3-2}$=6.4 Hz, $H_3$), 3.36 (dd, 1H, $J_{2'-3'}$=10.2 Hz, $J_{2'-1'}$=3.2 Hz, $H_{2'}$), 3.19 (s, 6H, 2 $OCH_3$, CDA), 1.83–1.78 (m, 1H, CDA), 1.72–1.61 (m, 3H, CDA), 1.52 (s, 3H, $CH_3$), 1.55–1.43 (m, 2H, CDA), 1.40–1.30 (m, 2H, CDA), 1.36 (s, 3H, $CH_3$); MALDI-TOF Calcd. for $C_{45}H_{57}N_3O_{12}$+$Na^+$: 855.0. found: 854.3, calcd. for $C_{45}H_{57}N_3O_{12}$+$K^+$: 871.1. found: 870.5

2-Azido-2-deoxy-3,4,6-tri-O-benzyl-D-glucopyranosyl-β(1-6)-4,5-O-(1',2'-dimethoxycyclohexane-1',2'-diyl)-1,2-O-isopropyliden-3-O-methyl-D-chiro-inositol (10)

$R_f$(Hex/EtOAc 3:1): 0.20;$[\alpha]^{20}_D$−8.0° (c=1.18, $CHCl_3$); $^1$H NMR ($CDCl_3$, 500 MHz): d 7.40–7.24 (m, 13H, Ph), 7.21–7.13 (m, 2H, Ph), 4.97 (d, 1H, $J_{1'-2'}$=8.1 Hz, $H_{1'}$), 4.92 (d, 1H, J=10.8 Hz, CHPh), 4.82 (d, 1H, J=10.8 Hz, CHPh), 4.78 (d, 1H, J=10.8 Hz, CHPh), 4.62 (d, I H, J=10.38 Hz, CHPh), 4.58 (AB syst., 2H, $CH_2$Ph), 4.49 (t, 1H, J=2.5 Hz, $H_{6'}$), 4.30 (dd, 1H, $J_{1-2}$=5.1 Hz, $J_{1-6}$=2.5 Hz, $H_1$), 4.20 (t, 1H, J=10.8 Hz, $H_4$), 4.17 (t, 1H, J=5.1 Hz, $H_2$), 3.98 (dd, 1H, $J_{5-4}$=10.8 Hz, $J_{5-6}$=2.5 Hz, $H_5$), 3.71–3.57 (m, 3H, $H_{5'}$, $H_6$, $H_{4'}$), 3.61 (s, 3H,$OCH_3$), 3.47–3.39 (m, 3H, $H_{3'}$, $H_3$, $H_{6'}$) 3.30 (dd, 1H, J=8.1 Hz, $H_{2'}$), 3.23 (s, 3H, $OCH_3$, CDA), 3.18 (s, 3H, $OCH_3$, CDA), 1.83–1.77 (m, 1H, CDA), 1.80–1.43 (m, 5H, CDA), 1.52 (s, 3H, $CH_3$), 1.41–1.28 (m, 2H, CDA), 1.33 (s, 3H, $CH_3$); $^{13}$C-NMR ($CDCl_3$, 125 MHz): d=138.5 (C), 138.4 (C), 138.3 (C), 128.9 (2CH), 128.8 (2CH), 128.8 (CR), 128.8 (2CH), 128.4 (2CH), 128.3 (2CH), 128.3 (CH), 128.2 (2CH), 128.1 (CH), 109.9 (C), 101.3 ($C_{1'}$), 98.4 (C, CDA), 98.0 (C, CDA), 83.9 ($C_3$),83.6 ($C_{3'}$),78.1 ($C_{4'}$), 76.7 ($C_1$), 76.0 ($CH_2$),75.9 ($C_{6'}$),75.5 ($CH_2$),75.4 ($CH_2$),73.9 ($C_6$),72.6 ($C_{5'}$),68.8 ($C_5$),68.7 ($C_2$),68.1 ($C_4$), 67.5 ($C_{2'}$), 60.4 ($OCH_3$),47.4 ($OCH_3$, CDA),47.3 ($OCH_3$, CDA),28.4 ($CH_3$),27.5 ($CH_2$),27.4 ($CH_2$),26.3 ($CH_3$),21.8 (2$CH_2$); HRFABMS Calcd. for $C_{45}H_{57}N_3O_{12}$: 854.3840. found32854.3872; MALDI-TOF Calcd. for $C_{45}H_{57}N_3O_{12}$+$Na^+$: 855.0. found: 854.3, calcd. for $C_{45}H_{57}N_3O_{12}$+$K^+$: 871.1. found: 870.4

2-Azido-2-deoxy-3,4,6-tri-O-benzyl-D-galactopyranosyl-α (1−6)-4,5-O-(1',2'-dimethoxycyclohexane-1',2'-diyl)-1,2-O-isopropyliden-3-O-methyl-D-chiro-inositol (14)

To a solution of 13 (84 mg, 0.14 mmol, 1.3 equiv), 7 (39 mg, 0.10 mmol, 1.0 equiv) in $CH_2Cl_2$:Hex, 1:3 (2 mL) and freshly activated 4Å molecular sieves were added and the mixture stirred for 1 h under Argon. Then, TMSOTf (2.43 mL, 0.02 mmol, 0.15 equiv) was added at −40° C. and the reaction mixture stirred for 24 h at 0° C. The suspension was filtered through celite and the solvent removed under vacuum to provide the crude material. Flash chromatography (Hex/EtOAc 4:1) afforded 14 (38 mg, 0.046 mmol, 46%). $R_f$ (Hex/EtOAc 1:1); 0.67; $[\alpha]^{20}_D$+59.7° (c=1.44, $CHCl_3$); $^1$H NMR ($CDCl_3$, 300 MHz): d=7.46–7.28, (m, 15H, Ph), 4.98 (d, 1H, J=3.3 Hz, $H_{1'}$), 4.89 (d, 1H, J=11.2 Hz, CHPh), 4.78 (d, 1H, J=11.1 Hz, CHPh), 4.69 (m, 1H, $H_{5'}$), 4.67 (d, 1H, J=11.1 Hz, CHPh), 4.59 (d, 1H, J=11.21 Hz, CHPh), 4.46, (AB syst., 2H, $CH_2$Ph),4.28 (t, 1H, J=6.3 Hz, $H_2$), 4.20 (m, 2H, $H_1$, $H_6$), 4.15 (bs, 1H, $H_{4'}$), 4.11 (m, 1H, $H_4$), 4.04 (dd, 1H, $J_{3'-2'}$=10.6 Hz, $J_{3'-4'}$=2.4 Hz, $H_{3'}$), 3.92 (dd, 1H, $J_{4-5}$=10.8 Hz, $J_{5-6}$ =2.1 Hz, $H_5$), 3.86 (dd, 1H, $J_{2'-3'}$=10.6 Hz, $J_{2'-1'}$=3.3 Hz, $H_{2'}$), 3.66–3.60 (m, 1H, $H_{6'b}$), 3.63 (s, 3H, $OCH_3$), 3.50 (dd, 1H, $J_{6a'-6b'}$=8.1 Hz, $J_{6a'-5'}$=5.4 Hz, $H_{6a'}$), 3.42 (dd, 1H, $J_{3-4}$ =10.2 Hz, $J_{3-2}$ =6.3 $H_3$), 3.20 (s, 3H, $OCH_3$, CDA), 3.18 (s, 3H, $OCH_3$, CDA), 1.90–1.63 (m, 4H, CDA), 1.54 (s, 3H, $CH_3$), 1.60–1.33 (m, 4H, CDA),1.40 (s, 3H, $CH_3$); $^{13}$C-NMR ($CDCl_3$, 75 MHz):δ 139.0 (C). 138.5 (C), 138.0 (C), 110.2 (C), 98.3 (C, CDA), 98.2 (C, CDA), 97.8 ($C_{1'}$), 83.6 ($C_3$), 80.6 ($C_2$), 77.2 ($C_{3'}$), 75.2 ($C_6$), 75.0 ($CH_2$), 73.9 ($C_{4'}$), 73.8 ($CH_2$), 72.8 ($C_1$), 72.7 ($CH_2$), 69.9 ($C_{5'}$), 68.4 ($C_{6'}$), 68.1 ($C_4$), 67.1 ($C_5$), 60.5 ($OCH_3$), 60.0 ($C_{2'}$), 47.2 (2$OCH_3$, CDA), 28.5 ($CH_3$), 27.4 ($CH_2$), 27.0 ($CH_2$), 26.7 ($CH_3$), 21.9 (2 $CH_2$; MALDI-TOF Calcd. for $C_{45}H_{57}N_3O_2$+$Na^+$: 855.0 Found: 854.0 Calcd. for $C_{45}H_{57}N_3O_{12}$+$K^+$: 871.1 Found: 870.1

2-Azido-2-deoxy-3,4,6-tri-O-benzyl-D-glucopyranosyl-α (1−6)-O-methyl-D-chiro-inositol (11)

Disaccharide (9) was dissolved in a mixture of trifluoroacetic acid/water (20:1, 3.7 mL) and stirred at room temperature for 40 min. Then, the reaction mixture was diluted with $CH_2Cl_2$ (10 mL) and immediately poured into an ice-cold, vigorously stirred solution of saturated aqueous sodium bicarbonate (90 mL). The layers were separated, and the aqueous phase extensively extrated ($CH_2Cl_2$, 4×30 ml), dried over $Na_2SO_4$ and concentrated under vacuum. Purification by flash chromatography ($Cl_2CH_2$/MeOH, 11:1 and then $CH_2Cl_2$/MeOH, 15.1) afforded 11 (4 mg, 6.138 mmol, 56%). $R_f$ ($Cl_2CH_2$/MeOH, 9:1): 0.3; $[\alpha]^{20}_D$+38.5° (c=0.19, $CHCl_3$); $^1$H NMR ($CDCl_3$, 500 MHz): d=7.34–7.16 (m,15H, Ph), 4.94 (d, 1H, J=3.5 Hz, $H_1$), 4.84 (AB syst., 2H, $CH_2$Ph), 4.79 (d, 1H, J=11.0 Hz, CHPh), 4.56 (d, 1H, J=11.0 Hz, CHPh), 4.50 (d, 1H, J=11.0 Hz, CHPh), 4.47 (d, 1H, J=11.0 Hz, CHPh), 4.16 (bs, 1H, $H_1$), 4.12 (m, 1H, $H_{5'}$), 4.04 (bs, 1H, $H_6$), 3.92 (m, 1H, $H_2$), 3.87–3.84 (m, 2H, $H_{3'}$, $H_5$), 3.71 (Yt, 1H, J=8.0 Hz, $H_4$), 3.56 (m, 3H, $H_{4'}$, 2$H_{6'}$), 3.63 (s, 3H, $OCH_3$), 3.44 (dd, 1H, $J_{2'-3'}$=10.0 Hz, $J_{1'-2'}$=3.5 Hz, $H_{2'}$), 3.37 (Ytr, 1H, J=8.0 Hz, $H_3$).

2-Azido-2-deoxy-3,4,6-tri-O-benzyl-D-glucopyranosyl-β(1-6)-3-O-methyl-D-chiro-inositol (12)

Compound 12 (28 mg, 43.0 mmol, 71%) was obtained via the general procedure described above for compound 11. Purification by flash chromatography (flex/EtOAc 1:20). $R_f$(EtOAc): 0.47; $^1$H NMR ($CDCl_3$, 500 MHz): d=7.34–7.26 (m, 13H, Ph), 7.19–7.10 (m, 2H, Ph), 4.83 (AB syst., 2H, $CH_2$Ph), 4.78 (d, 1H, J=11.0 Hz, CHPh), 4.54 (AB syst., 2H, CH$_2$Ph), 4,52 (d, 1H, J=11.0 Hz, CHPh), 4.46 (d, 11H, J=8.0 Hz, H$_{1'}$), 4.21 (bs, 1H, H$_1$), 4.10 (bs, 1H, H$_6$), 3.94–3.90 (m, 2H, H$_2$, H$_5$), 3.80 (t, 1H, J=8.5 Hz, H$_4$), 3.69–3.59 (m, 2H, 2H$_{6'}$), 3.62 (s, 3H, OCH$_3$), 3.58 (t, 1H, J=9.5 Hz, H$_{4'}$), 3.47 (t, 1H, J=9.5 Hz, H$_{3'}$), 3.46–3.36 (m, 3H, H$_{2'}$, H$_{5'}$,H$_3$), 3.35–3.27 (bs, 1H, OH), 3.27–3.15 (bs, 1H, OH), 3.15–2.94 (2bs, 2H, 2OH).

2-Azido-2-deoxy-3,4,6-tri-O-benzyl-D-galactopyranosyl-α(1-6)-3-O-methyl-D-chiro-inositol (16)

Compound 16 (7 mg, 10.7 mmol, 41%) was obtained via the general procedure described above for compound 11, using purification by flash chromatography (CH$_2$Cl$_2$/MeOH, 10:1). R$_f$(CH$_2$Cl$_2$/MeOH 9:1):0.48; $^1$H NMR (CDCl$_3$, 500 MHz): =7.36–7.21 (m, 15H, Ph), 4.96 (d, 1H, J$_{1-2}$=3.5 Hz, H$_{1'}$), 4.85 (d, 1H, J=11.5 Hz, CHPh), 4.71 (d, 1H, J=11.0 Hz, CHPh), 4.67 (d, 1H, J=11.0 Hz, CHPh), 4.49 (d, 1H, J=11.0 Hz), 4.49 (d, 1H, J=11.5 Hz, CHPh), 4.40 (d, 1H, J=11.0 Hz, CHPh), 4.20 (dd, 1H, J$_{4'-5'}$=7.5 Hz, J$_{5'-6'}$=4.5 Hz, H$_5$), 4.15 (t, 1H, J=4.0 Hz, H$_1$), 4.01 (t, 1H, J=4.0 Hz, H$_6$), 3.95–3.90 (m, 2H, H$_{2'}$, H$_{4'}$), 3.87 (m, 1H, H$_2$), 3.84 (dd, J$_{2'-3'}$=10.5 Hz, J$_{3'-4'}$=2.5 Hz, H$_{3'}$), 3.82–3.77 (m, 1H, H$_5$), 3.65 (t, 1H, J=8.2 Hz, H$_4$), 3.62 (s, 3H, OCH$_3$), 3.58 (dd, 1H, J$_{6a'-6b'}$=9.5 Hz, J$_{5'-6a'}$=7.5 Hz, H$_{6a'}$), 3.38 (dd, 1H, J$_{6a'-6b'}$=9.5 Hz, J$_{5'-6b'}$=4.5 Hz, H$_{6b'}$), 3.35 (t, 1H, J=8.2 Hz, H$_3$).

2-Amino-2-deoxy-D-glucopyranosyl-α(1-6)-3-O-methyl-D-chiro-inositol (1)

Compound 11 (3.8 mg, 5.831 mmol, 1.0 equiv) and 10% Pd/C (10 mg, 9.398 mmol) were stirred in methanol under a hydrogen atmosphere for 24 h. The slurry was filtered, washed with water and the filtrate was concentrated and lyophilized to give the fully deprotected disaccharide 1 (2.6 mg, 7.3 mmol, quantitative). R$_f$ (EtOAc/MeOH/H$_2$O/AcOH 2:2:1:1): 0.44;[α]$^{20}$$_D$+55.2° (c=0.125, H$_2$O). $^1$H NMR (D$_2$O, 500 MHz): δ=5.22 (d, 1H, H$_{1'}$), 4.16 (t, 1H, H$_1$), 4.19 (t, 1H, H$_6$), 4.07 (dt, 1H, H$_{5'}$), 3.90 (dd, 1H, H$_5$), 3.85–3.75 (m, 3H, H$_{40'}$, H$_{6a'}$,H$_{6b'}$), 3.80 (dd, 1H, H$_2$), 3.70 (t, 1H, H$_{3'}$), 3.64 (s, 3H, OCH$_3$), 3.52 (t, 1H, H$_4$), 3.36 (t, 1H, H$_3$), 3.24 (dd, 1H, H$_{2'}$).

2-Amino-2-deoxy-D-glucopyranosyl-β(1-6)-3-O-methyl-D-chiro-inositol (2)

Compound 12 (24 mg, 67.54 mmol, 98%) was treated as described above to afford compound 2. R$_f$ (EtOAc/MeOH/H$_2$O/AcOH 2:2:1:1): 0.42, $^1$H NMR (D$_2$O, 500 MHz): d=4.70 (d, 1H, J=8.5 Hz, H$_{1'}$), 4.32 (Ψt, 1H, J=3.5 Hz, H$_1$), 4.12 (Ψt, 1H, J=3.5 Hz, H$_6$), 3.96 (dd, 1H, J$_{6a'-6b'}$=9.5 Hz, J$_{6a'-5'}$=1.7 Hz, H$_{6a'}$), 3.92 (dd, 1H, J$_{5-4}$=8.5 Hz, J$_{5-6}$=3.5 Hz, H$_5$), 3.88 (dd, 1H, J$_{2-3}$=9.8 Hz, J$_{1-2}$=6.6 Hz, H$_2$), 3.82 (dd, 1H, J$_{6a',6b'}$=9.5 Hz, J$_{5'-6b'}$=4.0 Hz, H$_{6b'}$), 3.78 (t, 1H, J=9.5 Hz, H$_{4'}$), 3.66 (s, 3H, OCH$_3$), 3.48 (t, 1H, J=9.8 Hz, H$_{4'}$), 3.57-3.51 (m, 2H, H$_{3'}$, H$_{5'}$), 3.40 (t, 1H, J=9.8 Hz, H$_3$), 2.86 (t, 1H, J=8.5 Hz, H$_{2'}$).

2-Amino-2-deoxy-D-glucopyranosyl-α(1-6)-3-O-methyl-D-chiro-inositol (14)

Compound 14 (5.3 mg, 14.9 mmol, quantitative) was obtained via the general procedure described above for compound 12, R$_f$ (Cl$_2$CH$_2$/MeOH 9/1): 0.071; [α]$^{20}$$_D$(c= 0.305, H$_2$O):+70.1; $^1$H NMR (D$_2$O, 500 MHz): δ =5.31 (d, 1H, J=3.5 Hz, H$_{1'}$), 4.29 (t, 1H), 4.19 (Ψt, 1H, H$_1$), 4.14 (Ψt, 1H, H$_6$), 4.05 (Ψs, 1H, H$_{4'}$), 3.92 (dd, 1H), 3.77 (d, 3H), 3.72 (t, 1H), 3.65 (s, 3H, OCH$_3$), 3.62 (m, 1H), 3.52 (dd, 1H, J$_{2'-3'}$=11.0 Hz, J$_{1'-2'}$=3.5 Hz, H$_{2'}$), 3.37 (t, 1H, J=10.0 Hz, H$_3$).

Synthesis of RGL1105

1'-D-4'-O-(2",3",4"-tri-O-benzyl-6"-tertbutyldimethylsilyl-α-D-mannopyranosyl)-[1'-D-6-O-(2'-azido-3',6'-di-O-benzyl-2'-deoxy-α-D-glucopyranosyl)-1,2-O-(L-1,7,7-trimethyl[2.2.1]-bicyclohept-2-ylidene)-3,4,5-tri-O-benzyl-myo-inositol] (3)

A mixture of compounds 1 (284 mg, 0.298 mmol) and 2 (340 mg, 0.408 mmol), was dissolved in Toluene and the solvent removed (3×10 mL). To the water-free solid mixture, Et$_2$O anh. (10 mL) and 4Å powdered molecular sieves was added and allowed to dissolve at room temperature under Argon atmosphere. After 5 min, TMSOTf (12 μL, 0.066 mmol) was added and the reaction allowed to proceed for 90 min. Then, the reaction was quenched with Et$_3$N (2 mL) and after 5 min stirring, the solvents are removed and the residue purified by column chromatography (SiO$_2$, hexane/AcOEt 19:1), to obtain 3 (363 mg, 75%). $^1$H NMR (CDCl$_3$, 500 MHz): d 7.72–7.58 (m, 5H, ArH), 7.42–7.13 (m, 39H, ArH), 7.07 (m, 5H, ArH), 6.94 (t, J=7.5 Hz, 1H, ArH), 5.58 (d, J=3.0 Hz, 1H, H anom.), 5.261 (d, J=2.9 Hz, 1H, H anom.), 4.95 (d, J=11 Hz, 1H, H benc.), 4.87 (d, J=11 Hz, 1H, H benc.), 4.75–4.63 (m, 7H), 4.62–4.49 (m, 4H), 4.42 (m, 2H), 4.46 (m, 3H), 4.7 (d, J=12.0 Hz, 1H, H benc.), 4.12 (m, 3H), 4.1 (dd, J$_1$=3 Hz, J$_2$=11.5 Hz, 1H), 3.98–3.91 (m, 3H), 3.78–3.89 (m, 4H), 3.69 (m, 1H), 3.49–3.61 (m, 2H), 3.44 (m, 1H), 1.99 (m, 2H), 1.74–1.85 (m, 2H), 1.55 (d, J=12.5 Hz, 1H),1.47 (m, 1H), 1.27–1.38 (m, 1H), 1.10 (s, 3H), 0.95 (s, 3H), 0.92 (s, 3H).

1"-D-4'-O-(2",3",4"-tri-O-benzyl-α-D-mannopyranosyl)-[1'-D-6-O-(2'-azido-3',6'-di-O-benzyl-2'-deoxy-α-D-glucopyranosyl)-1,2-O (L-1,7,7-trimethyl[2.2.1]-bicyclohept-2-ylidene)-3, 4,5-tri-O-benzyl-myo-inositol] (4)

A solution of 3 (290 mg, 0.179 mmol) in THF (15 mL) under Argon atmosphere, was treated with TBAF (1.0 M in THF, 1.8 mL, 1.800 mmol) at 0° C. The reaction mixture was allowed to reach room temperature and kept stirring for 66 h. Then, the solvents were removed, the remaining material redissolved in AcOEt (50 mL), washed with NaCl s.s. (3×50 mL), dried over MgSO$_4$ and the solvents evaporated. The residue was purified by column chromatography (SiO$_2$, hexane/AcOEt 9:1 to 8:1 to 6:1 and finally 4:1), to obtain 4 (206 mg, 83%). $^1$H NMR (CDCl$_3$, 500 MHz): 7.25–7.44 (m, 37H, ArH), 7.11–7.20 (m, 3H, ArH), 5.68 (d, J=3.5 Hz, 1H, H anom.), 5.32 (d, J=2 Hz, 1H, H anom.), 4.95 (m, 1H), 4.55–4.86 (m, 12H), 4.50 (d, J=12 Hz, 1H, H benc.), 4.40 (d, J=12 Hz, 1H, H benc.),4.34 (m, 1H), 4.20 (d, J=12 Hz, 1H, H benc.), 4.10 (m, 3H), 3.82–4.03 (m, 6H), 3.64–3.76 (m, 5H), 3.47–3.58 (m, 2H), 3.41 (dd, J$_1$=3.5 Hz, J$_2$=10 Hz, 1H), 2.4 (s,1H, OH), 1.97 (m, 2H), 1.74–1.84 (m, 2H), 1.53 (d, J=13 Hz, 1H), 1.47 (m, 1H), 1.24–1.35 (m, 1H), 1.13 (s, 3H), 0.94 (s, 3H), 0.93 (s, 3H).

1"-D-4'-O-(2",3",4"-tri-O-benzyl-6"-dibenzylphosphate-α-D-mannopyranosyl)-[1'-D-6-O-(2'-azido-3',6'-di-O-benzyl-2'-deoxy-D-glucopyranosyl)-1,2-O-(L-1,7,7-trimethyl[2.2.1](-bicyclohept-2-ylidene)-3,4,5-tri-O-benzyl-myo-inositol] (5)

To a solution of trisaccharide 4 (190 mg, 0.137 mmol) and 1H-Tetrazole in anhydrous CH$_2$Cl$_2$ (10 mL) under Argon atmosphere and at 0° C., dibenzyl diisipropylphosphoramidite (DBPA, 0.1 mL, 0.298 mmol) was added. The reaction mixture was stirred for 3 h, while allowing to reach room temperature. Then, the reaction mixture was cooled to 0° C. and a solution of 70% 3-chloroperbenzoic acid (85 mg, 0.345 mmol) in anh. CH$_2$Cl$_2$ (5 mL) was added. The mixture was stirred for 1 h, diluted with CH$_2$Cl$_2$ (25 mL), washed with sat. Na$_2$SO$_3$ (2×50 mL), sat. NaHCO$_3$ (2×50 mL) and sat. NaCl (2×50 mL), dried over MgSO$_4$ and concentrated. Flash chromatography of the crude mixture (hexane/AcOEt 9/1, 8/1, 7/1, 6/1, 5/1 and 4/1) gave compound 5(210 mg, 93%). $^1$H-NMR (CDCl$_3$, 500 MHz): d 7.13-7.42 (m, 49H, ArH), 7.08 (m, 1H, ArH), 5.66 (d, J=3.5 Hz, 1H H anom.), 5.28 (d, J=2 Hz, 1H, H anom.), 4.90–5.03 (m, 6H), 4.75–4.81 (m, 4H), 4.72 (d, J=12 Hz, 1H, H benc.), 4.65 (m, 2H), 4.52–4.61 (m, 3H), 4.45 (m, 2H), 4.34 (m, 2H), 4.15–4.29 (m, 3H), 4.03–4.12 (m, 4H), 3.80–3.94 (m, 5H), 3.72 (m, 2H), 3.56 (m, 2H), 3.49 (m, 1H), 3.57 (dd, $J_1$=3.5 Hz, $J_2$=10 Hz, 1H), 1.97 (m, 2H), 1.78 (m, 2H), 1.52 (d, J=12.5 Hz, 1H), 1.46 (m, 1H), 1.28 (m, 1H), 1.12 (s, 3H), 0.93 (s, 3H), 0.89 (s, 3H). $^{31}$P-NMR CDCl$_3$, 202 MHz): d −1.72.

1"-D-4'-O-(2",3",4"-tri-O-benzyl-6"-dibenzylphosphate-α-D-mannopyranosyl)-[1'-D-6-O-(2'-azido-3',6'-di-O-benzyl-2'-deoxy-α-D-glucopyranosyl)-3,4,5-tri-O-benzyl-myo-inositol] (6)

To a solution of trisaccharide 5 (200 mg, 0.122 mmol) in CH$_2$Cl$_2$ (15 mL) H$_2$O (0.2 mL, 11.1 mmol), and trifluoro-acetic acid (0.6 mL, 7.81 mmol) were added and the reaction stirred for 18 h at r.t. The mixture was then diluted with AcOEt (50 mL), washed with sat. NaHCO$_3$ (2×50 mL), sat. NaCl (3×50 mL), dried over MgSO$_4$ and concentrated. Flash chromatography of the crude mixture (hexane/AcOEt 4/1, 2/1, 1/1 y 1/2) gave compound 6 (142 mg, 77%). $^1$H-NMR (CDCl$_3$, 500 MHz): d 7.10–7.39 (m, 50H), 5.53 (d, J=3.5 Hz, 1H, H anom.), 5.24 (d, J=2.5 Hz, 1H, H anom.), 4.87–5.03 (m, 5H), 4.72–4.79 (m, 4H), 4.63 (m, 2H), 4.57 (d, J=12Hz, 1H, H benc.), 4.49 (d, J=12 Hz, 1H, H benc.), 4.25–4.38 (m, 3H), 4.09–4.26 (m, 4H), 4.01–4.09 (m, 3H), 3.95 (m, 1H), 3.84 (m, 3H), 3.69 (m, 3H), 3.6 (m, 1H), 3.5 (m, 1H), 3.43 (m, 2H), 3.37 (m, 1H), 3.29 (m, 1H), 2.94 (wide s., 1H, OH). $^{31}$P-RMN (CDCl$_3$, 202 MHz): d-1.79.

1"-D-4'-O-(6"-phosphate-α-D-mannopyranosyl)-[1'-D-6-O-(2'-amino-2'-deoxy-α-D-glucopyranosyl)-myo-inositol] (RGL1105)

To a suspension of trisaccharide 6 (115 mg, 0.076 mmol) in a mixture of MeOH/H$_2$O (5 mL, 9:1) 10% Pd/C (162 mg, 0.152 mmol) was added and the reaction stirred under hydrogen atmosphere at r.t. for 24 h. The solvent was evaporated, the crude suspended in H$_2$O (10 mL), filtered through celite and the filtrate lyophilized to give RGL1105 (45 mg, quant.). 1H-RMN (D$_2$O, 500 MHz): d 5.46 (d, 3.5 Hz, 1H, H anom.), 5.31 (s, 1H, H anom.), 4.0–4.27 (m, 6H), 3.72–3.92 (m, 8H), 3.68 (t, J=9.5 Hz, 1H), 3.54 (m, 1H), 3.41 (m, 1H). $^{31}$P-RMN (D$_2$O, 202 MHz): d 0.66.

Synthesis of RGL1115
Synthesis of 1'-D-6-O-(2'-azido-3'-O-benzyl-4',6'-O-benzylidene-2'-deoxy-α-D-glucosopyranosyl)-1,2-O-(L-1,7,7-trimethyl[2.2.1]-bicyclohept-2-ylidene)-3,4-O-(1,1,3,3,-tetraisopropyldisiloxanyl)-5-O-di-benzylphosphate-myo-inositol 12

To a solution of a-1,6 anomer 11 (0.16 mmol) and 1-H-tetrazole (0.63 mmol) in anhydrous Cl$_2$CH$_2$ (15 ml) at 0° C. (ice bath) was added dropwise dibenzyl diisopropylphosphoramidite (0.63 mmol). After the addition was completed the ice-bath was removed and the mixture left to stir under an inert atmosphere whilst being monitored by TLC analysis (hexane:EtOAc [4:1]). After 72 hours the α-1,6 anomer 11 starting material had been consumed. A solution of mCPBA (0.39 mmol) in anhydrous DCM (5 ml) was added to the reaction vessel and the mixture left to stir for 3 hours at R.T. under an inert atmosphere. The mixture was diluted with DCM (30 ml), washed with sat. Na$_2$SO$_3$ (2×25 ml), sat. NaHCO$_3$ (2×25 ml) and brine (2×25 ml). The organic layer was then dried over MgSO$_4$ and concentrated to dryness in vacuo. The crude product was purified by column chromatography (hexane:EtOAc [4:1]) to yield phosphate 12 as a pale yellow oil (60%). $^6$Si (CDCl$_3$: 360 MHz) 4.6 (2H, dd, PhC$\underline{H}_2$O), 5.3 (1H, d, H1',5.4 (1H, s, PhC$\underline{H}$O); $\delta_H$ (CDCl$_3$: 146 MHz) 0.2 (1P').

Synthesis of 1'-D-6-O-(2'-azido-3'-O-benzyl-4',6'-O-benzylidene-2'-deoxy-α-D-glucosopyranosyl)-1,2-O-(L-1,7,7-trimethyl[2.2.1]-bicyclohept-2-ylidene)-5-O-di-benzylphosphate-myo-inositol 13

To a solution of phosphate 12 (0.09 mmol) in anhydrous THF (1.3 ml) at 0° C. (ice bath) was added TBAF (1.0 M solution in THF) (0.2 ml) and the reaction left to stir at R.T. under an inert atmosphere. After 45 minutes TLC analysis (hexane:EtOAc [3:2]) indicated that all phosphate 12 starting material had been consumed. The reaction mixture was concentrated to dryness in vacuo before being purified by column chromatography (hexane:EtOAc [3:2]) to yield de-silylated saccharide 13 as a pale yellow oil (44%). $\delta_H$ (d4-MeOH: 360 MHz) 5.4 (1H, d, H1'), 5.5 (1H, s, PhC$\underline{H}$O); $\delta_P$ (d4-MeOH: 146 MHz) 1.1 (1P$^v$).

Synthesis of 1'-D-6-O-(2'-azido-3'-O-benzyl-2'-deoxy-α-D-glucosopyranosyl)-5-O-di-benzylphosphate-myo-inositol 14

To a solution of de-silylated saccharide 13 (0.04 mmol) in DCM (5.0 ml) was added distilled water (44 ml) then TFA (187 ml) and the mixture stirred at R.T. for 4 hours whilst being monitored by TLC analysis (EtOAc). The reaction mixture was concentrated to dryness in vacuo before the crude product was purified by column chromatography (EtOAc [100%] then EtOAc:MeOH [10:1]) to yield the de-protected saccharide 14 (89%) as a pale yellow oil. $\delta_H$ (d4-MeOH: 360 MHz) 5.3 (1H, d, H1'); $\delta_P$ (d4-MeOH: 146 MHz) 0.9 (1P$^v$).

Synthesis of 1'-D-6-O-(2'-amino-2'-deoxy-α-D-glucosopyranosyl)-5-O-phosphate-myo-inositol 15

To a suspension of de-protected saccharide 14 (0.04 mmol) in a mixture of HPLC grade methanol:distilled water [4:1]) (1 ml) was added 10% wt. Pd/C (10 mg) and the mixture stirred under an atmosphere of hydrogen at R.T. for 72 hours. The methanol was evaporated in vacuo before the crude product was suspended in distilled water then filtered through celite. The filtrate was then evaporated to dryness in vacuo to yield a yellow oil. $^1$H-NMR analysis of this oil indicated benzyl groups remained on the pseudo-disaccharide. Consequently, the oil was re-suspended in a mixture of HPLC grade methanol:distilled water [4:1] (1 ml). 10% wt. Pd/C (10 mg) was added and the mixture stirred under an atmosphere of hydrogen at R.T. for a further 20 hours. The methanol was evaporated in vacuo, the crude product suspended in distilled water before being filtered through celite. The filtrate was then evaporated to dryness in vacuo to yield de-protected phosphate 15 as a dark yellow oil. $^1$H-NMR analysis indicated that the product 15 was slightly contaminated with impurities. The product 15 was therefore re-dissolved in distilled water and washed with EtOAc. The aqueous layer was then concentrated to dryness in vacuo to give pure de-protected phosphate 15 (11 mg) as a light brown oil. $\delta_H$ (D$_2$O: 360 MHz) 5.6 (1H, d, H1'); $\delta_P$ (D$_2$O: 146 MHz) 2.4 (1P$^v$).

Synthesis of RGL 1116
Synthesis of 1'-D-6-O-(2'-azido-3'-O-benzyl-4',6'-O-benzylidene-2'-deoxy-α-D-glucosopyranosyl)-1,2-O-(L-1,7,7-trimethyl[2.2.1]-bicyclohept-2-ylidene)-3,4-O-(1,1,3,3,-tetraisopropyldisiloxanyl)-5-O-acetyl-myo-inositol 16

α-1,6 Anomer 11 (0.16 mmol) was dissolved in acetic anhydride (2 ml) before pyridine (4 ml) was added. The reaction mixture was then stirred at R.T. overnight. TLC analysis (hexane:EtOAc [9:1]) of the reaction mixture suggested that only c.a. 50% of the α-1,6 anomer 11 starting material had been consumed. The reaction was therefore heated to 45° C. for 8 hours at which point TLC analysis (hexane:EtOAc [9:1]) indicated complete consumption of the α-1,6 anomer 11 starting material The reaction mixture was concentrated to dryness in vacuo, using toluene to azeotropically remove the pyridine. The crude product was then purified by column chromatography (hexane:EtOAc (8:1)) to yield acetate 16 (89%) as a pale yellow oil. $\delta_H$ (CDCl$_3$: 360 MHz) 5.1 (2H, dd, PhC$\underline{H}_2$O), 5.3 (1H, dd, H5), 5.7 (1H, d, H1'), 5.8 (1H, s, PhC$\underline{H}$O).

Synthesis of 1'-D-6-O-(2'-azido-3'-O-benzyl-4',6'-O-benzylidene-2'-deoxy-α-D-glucosopyranosyl)-1,2-O-(L-1,7,7-trimethyl[2.2.1]-bicyclohept-2-ylidene)-5-O-acetyl-myo-inositol 18

To a solution of acetate 16 (0.14 mmol) in anhydrous THF (2.0 ml) at 0° C. was added TBAF (1.0 M solution in THF) (310 ml) and the reaction left to stir at R.T. under an inert atmosphere. After 1.5 hours TLC analysis (hexane:EtOAc [3:2]) indicated that the acetate 16 starting material had been consumed. The reaction mixture was concentrated to dryness in vacuo before being purified by column chromatography (hexane:EtOAc [3:2]) to yield de-silylated acetate 18 as a pale yellow oil (42 h). $\delta_H$ (CDCl$_3$: 360 MHz) 4.7 (1H, dd, H5), 4.8 (2H, dd, PhC$\underline{H}_2$O), 5.3 (1H, d, H1'), 5.5 (1H, s, PhC$\underline{H}$O).

Synthesis of 1'-D-6-O-(2'-azido-3'-O-benzyl-2'-deoxy-α-D-glucosopyranosyl)-5-O-acetyl-myo-inositol 20

To a solution of de-silylated acetate 18 (0.06 mmol) in DCM (3.0 ml) was added distilled water (64 ml) then TFA (273 ml) and the mixture stirred at R.T. for 4.5 hours whilst being monitored by TLC analysis (EtOAc:MeOH [10:1]). The reaction mixture was concentrated to dryness in vacuo before the crude product was purified by column chromatography (EtOAc (100%) then EtOAc:MeOH [10:1]) to yield the de-protected acetate 20 (55%) as an orange oil. $\delta_H$ (d4-MeOH: 360 MHz) 4.8 (3H, m, H5 and PhC$\underline{H}$O), 5.4 (1H, d, H1').

Synthesis of 1'-D-6-O-(2'-amino-2'-deoxy-α-D-glucosopyranosyl)-5-O-acetyl-myo-inositol 22

To a suspension of de-protected acetate 20 (0.03 mmol) in a mixture of HPLC grade methanol distilled water [10.1] (1 ml) was added 10% wt. Pd/C (5 mg) and the mixture stirred under an atmosphere of hydrogen at R.T. for 24 hours. The methanol was evaporated in vacuo before the crude product was suspended in distilled water then filtered through celite. The filtrate was then evaporated to dryness in vacuo to yield de-protected acetate 22 as a colourless oil (7 mg).

Synthesis of 1'-D-6-O-(2'-azido-3-O-benzyl-4',6'-O-benzylidene-2'-deoxy-β-D-glucosopyranosyl)-1,2-O-(L-1,7,7-trimethyl[2.2.1]-bicyclohept-2-ylidene)-3,4-O-(1,1,3,3,-tetraisopropyldisiloxanyl)-5-O-acetyl-myo-inositol 17

β-1,6 Anomer 9 (0.12 mmol) was dissolved in acetic anhydride (2 ml) before pyridine (4 ml) was added. The reaction mixture was then stirred at R.T. overnight. TLC analysis (hexane:EtOAc [9:1]) of the reaction mixture suggested that only c.a. 50% of the β-1,6 anomer 9 starting material had been consumed. The reaction was therefore heated to 45° C. for 9 hours at which point TLC analysis (hexane:EtOAc [9:1]) indicated that only a small quantity of the β-1,6 anomer 9 starting material remained unreacted. The reaction mixture was concentrated to dryness in vacuo, using toluene azeotropically remove the pyridine. The crude product was then purified by column chromatography (hexane:EtOAc [8:1]) to yield acetate 17 (63%) as a pale yellow oil. $\delta_H$ (CDCl$_3$: 360 MHz) 4.8 (2H, dd, PhC$\underline{H}$O), 5.0 (1H, dd, H5), 5.3 (1H, d, H1'), 5.5 (1H, s, PhC$\underline{H}$O).

Synthesis of 1'-D-6-O-(2'-azido-3'-O-benzyl-4',6'-O-benzylidene-2'-deoxy-β-D-glucosopyranosyl)-1,2-O-(L-1,7,7-trimethyl[2.2.1]-bicyclohept-2-ylidene)-5-O-acetyl-myo-inositol 19

To a solution of acetate 17 (0.08 mmol) in anhydrous THF (2.0 ml) at 0° C. was added TBAF (1.0 M solution in THF) (165 ml) and the reaction left to stir at R.T. under an inert atmosphere. After 1.5 hours TLC analysis (hexane:EtOAc [3:2]) indicated that the acetate 17 starting material had been consumed. The reaction mixture was concentrated to dryness in vacuo before being purified by column chromatography (hexane:EtOAc [3:2]) to yield de-silylated acetate 19 as a pale yellow oil (53%). $\delta_H$(CDCl$_3$: 360 MHz) 4.8 (3H, m, PhC$\underline{H}_2$O) and H5), 5.5 (1H, d, H1').

Synthesis of 1'-D-6-O-(2'-azido-3'-O-benzyl-2'-deoxy-β-D-glucosopyranosyl)-5-O-acetyl-myo-inositol 21

To a solution of de-silylated acetate 19 (0.04 mmol) in DCM (3.0 ml) was added distilled water (46 ml) then TFA (200 ml) and the mixture stirred at R.T. for 4.5 hours whilst being monitored by TLC analysis (EtOAc). The reaction mixture was concentrated to dryness in vacuo before the crude product was purified by column chromatography (EtOAc (100%) then EtOAc:MeOH [10:1]) to yield the de-protected acetate 21 (67%) as an orange oil. $\delta_H$ (d4-MeOH: 360 MHz) 4.8 (3H, m, PhC$\underline{H}_2$O and H5), 5.4 (1H, d, H1').

Synthesis of 1'-D-6-O-(2'-amino-2'-deoxy-β-D-glucosopyranosyl)-5-O-acetyl-myo-inositol 23

To a suspension of de-protected acetate 21 (0.03 mmol) in a mixture of HPLC grade methanol:distilled water [10:1] (1 ml) was added 10% wt. Pd/C (6 mg) and the mixture stirred under an atmosphere of hydrogen at R.T. for 48 hours. The methanol was evaporated in vacuo before the crude product was suspended in distilled water then filtered through celite. The filtrate was then evaporated to dryness in vacuo to yield de-protected acetate 23 as a colourless oil (7 mg).

| Assay Data | |
|---|---|
| PDH activation: | 100 μM |
| RGL1023 | 14% |
| RGL1027 | 132% |
| RGL1029 | 361% |
| RGL1015 | 38% |
| RGL1024 | 65% |
| RGL1025 | 17% |

| PKA inhibition: | 0.1 μM | 1.0 μM | 10 μM |
|---|---|---|---|
| RGL1027 | 18% | | 10% |
| RGL1029 | 59% | | 33% |
| RGL1018 | 19% | | — |
| RGL1019 | 32% | | 31% |
| RGL1015 | 14% | 15% | 12% |
| RGL1024 | 17% | 34% | 2% |
| RGL1025 | 48% | −13% | |

References:

The references mentioned herein are all expressly incorporated by reference.

[1](a) Varela-Nieto et al, *Comp. Biochem. Physiol.*,. 115B: 223–241, 1996; (b) Strälfors, *Bioassays*, 19:327–335, 1997; (c) Field, *Glycobiology*, 7:161–168, 1997; d) Jones & Varela-Nieto, *Int. J. Biochem. Cell Biol.*, 30:313–326, 1998.

[2] Mato et al, *Biochem. Biophys. Res. Commun.*, 146:746–770, 1987.

[3] Larner et al, *Biochem. Biophys. Res. Commun.*, 151:1416–1426, 1998.

(4) Caro et al, *Biochem. Mol. Med.*, 61:214–228, 1997.

[5] For recent reviews on the synthesis of these structures see: a) Gigg & Gigg in *Glycopeptides and Related*

Compounds, Large & Warren, Eds., Marcel Dekker, New York, 1997, pp 327–392; Khiar & Martin-Lomas in *Carbohydrate Mimics*. Concepts and Methods, Chapleur Ed Wiley VCH, 1998, pp 443–462; Dietrich et al, *Chem. Eur. J.*, 5:320–336, 1999.

[6] Jaramillo et al, *J. Org. Chem.*, 59, 3135–3141, 1994.
[7] Corey & Venkateswarlu, *J. Am. Chem. Soc.*, 94:6190, 1974.
[8] Ley et al, *Angew.Chem. Int. Ed. Engl.*,33:2290–2292, 1994.
[9] Kirnzi & Schmidt, *Liebigs Ann. Chem.*, 1537–1545, 1985.
[10] Vasella et al, *Helv. Chim. Acta.*, 74:2073–2077, 1991.
[11] Schmidt & Kinzi, *Adv. Carbohydy. Chem. Biochem.*, 50:21–123, 1994.
[12] Once et al, *Chem. Eur. J.* 3:431–440, 1997.
[13] Rademacher et al, *Brazilian J. Med. Biol. Res.*, 27:327–341, 1994.
[14] Caro et al, *Biochem. Molec. Med.*, 61:214–229, 1997.
[15] Kunjara et al, In: Biopolymers and Bioproducts: Structure, Function and Applications, Ed Svati et al, 301–305, 1995.
[16] Zapata et al, *Carbohydrate Res.*, 264:21–31, 1994.
[17] Dietrich et al, *Chem. Eur. J.*,5:320–336, 1999.
[18] Baeschlin et al, *Chem. Eur. J.*, 6(1): 172–186, 2000.
WO98/11116 and WO98/11117 (Rademacher Group Limited).
WO98/11435 and WO98/10791 (Rademacher Group Limited).
WO99/38516 (Rademacher Group Limited).

What is claimed is:

1. A compound represented by the general formula:

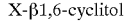

X-β1,6-cyclitol wherein:
X represents a sugar residue;
the sugar residue is unsubstituted or substituted with between one and four groups, and the cyclitol is unsubstituted or is further substituted with between one and four groups, said between one and four groups being substituted on at least one of said sugar residue and said cyclitol and being independently selected from:
(a) a phosphoryl group having a formula selected from the group consisting of —O—P(O)(OH)$_3$, —O—P(S)(OH)$_2$, —O—P(O)(OR)$_2$, —O—P(S)(OR)$_2$, —O—P(O)OHR, —O—P(S)OHR, —O—P(O)OR$_1$R$_2$, —O—P(S)OR$_1$R$_2$, —O—P(S)(OH)(SH), or a cyclic phosphate;
(b) a phosphorus-containing group having a formula selected from the group consisting of —O—P(OR)—NR$_1$R$_2$ and —O—P(O)(OR)—NR$_1$R$_2$;
(c) sulphur-containing group having a formula selected from the group consisting of —O—S(O)(OH)$_3$, —SH, —SR, —S(—O)—R, —S(O)$_2$R, RO—S(O)$_2$$^-$, —O—SO$_2$NH$_3$, —O—SO$_2$R$_1$R$_2$ or —NHSO$_2$NH$_2$;
(d) a substituted-amino containing group having a formula selected from the group consisting of —NHR, —NR$_1$R$_2$, —NHAc, —NHCOR, —NH—O—COR, —NHSO$_3$$^-$, —NHSO$_2$R, —N(SO$_2$R), —NHC(=NH)NH$_2$ —NH—CO—NR$_1$R$_2$ or —NH—C(S)—NH$_2$;
(e) a hydroxy group; a substituted hydroxy group represented by the formula —OR$_3$, where R$_3$ is C$_{1-10}$ unsubstituted akyl or C$_{1-10}$ substituted alkyl, alkoxyalkyl, aryloxyalkyl, cycloalkyl, alkenylalkyl in which the alkyl group is unsubstituted alkylene, cycoalkyl in which the cycloalkyl group ha 3–7 carbon atoms, —OCOR, aryl, heteroaryl, acetal, or said substituted groups comprise two hydroxyl groups that are joined to form a ketal;
(f) halogen substituents fluorine or chlorine;
(g) hydrogen forming a deoxy sugar;
wherein R, R$_1$, and R$_2$ are independently hydrogen or C$_{1-10}$ unsubstituted alkyl or C$_{1-10}$ substituted alkyl or a aryl;
or a derivative of the compound, said derivative comprising salts, coordination complexes with metal ions, esters, free acids or bases, hydrates or protecting groups.

2. A composition comprising a compound of claim 1 in combination with a pharmaceutically acceptable carrier.

3. The compound of claim 1, wherein the cycitol is selected from myo-inositol, chiro-inositol or pinitol.

4. The compound of claim 1, wherein the sugar residue is unsubstituted hexose or pentose, or said substituted form thereof.

5. The compound of claim 4, wherein the sugar residue is a hexose selected from the group consisting of glucose, galactose mannose.

6. The compound of claim 4, wherein the sugar residue is a hexosamine.

7. The compound of claim 6, wherein the hexosamine is galactosamine or glucosamine.

8. The compound of claim 1, wherein the cyclitol is a D or L-enantionmer.

9. The compound of claim 1, wherein said substituted hydroxy group is OR$_3$, and R$_3$ is selected from the groups consisting of CHF$_2$ and CF$_3$.

10. The compound of claim 1, wherein said derivative is a coordination complex with metal ion selected from the group consisting of Mn(+2) and Zn(+2).

11. The compound of claim 1, which is selected from the group consisting of:
RGL1018 O-(2'-amino-2'-deoxy-D-glucopyranosyl)-β(1,6)-D-chiro-inositol;
RGL1015 O-(2-amino-2-deoxy-D-glucopyranosyl)-β(1,6)-3-O-methyl-chiro-inositol; and
RGL1120 1'-D-6-O-(2'-amino-2'-deoxy-β-D-glucopyranosyl)-D-chiro-inositol.

12. The compound selected from the group consisting of:
RGL1018 O-(2'-amino-2'-deoxy-D-glucopyranosyl)-β(1,6)-D-chiro-inositol;
RGL1015 O-(2-amino-2-deoxy-D-glucopyranosyl)-β(1,6)-3-O-methyl-chiro-inositol; and
RGL1120 1'-D-6-O-(2'-amino-2'-deoxy-β-D-glucopyranosyl)-D-chiro-inositol;
and substituted forms of said compounds wherein the sugar residue is unsubstituted or substituted with between one and four groups and the cyclitol is unsubstituted or is further substituted with between one and four groups, said between one and four groups being substituted at least one of said sugar residue and said cyclitol and being independently selected from the group consisting of:
(a) a phosphoryl group having a formula selected from the group consisting of —O—P(O)(OH)$_2$, —O—P(S)(OH)$_2$, —O—P(O)(OR)$_2$, —O—P(S)(OR)$_2$, —O—P(O)OHR, —O—P(S)OHR, —O—P(O)OR$_{,1}$R$_2$, —O—P(S)OR$_1$R$_2$, —O—P(S)(OH)(SH), or a cyclic phosphate;
(b) a phosphorus-containing group having a formula selected from the group consisting of —O—P(OR)—NR$_1$R$_3$ and —O—P(O)(OR)—NR$_1$R$_2$;

(c) sulphur-containing group having a formula selected from the group consisting of —O—S(O)(OH)$_2$, —SH, —SR, —S(=O)—R, —S(O)$_2$R, RO—S(O)$_2^-$, —O—SO$_2$NH$_2$, —O—SO$_2$R$_1$R$_2$ or —NHSO$_2$NH$_2$;

(d) a substituted-amino containing group having a formula selected from the group consisting of —NHR, —NR$_1$R$_2$, —NHA$_c$, —NHCOR, —NH—O—COR, —NHSO$_3^-$, —NHSO$_2$R, —N(SO$_2$R), —NHC(=NH)NH$_2$, —NH—CO—NR$_1$R$_2$ or —NH—C(S)—NH$_2$;

(e) a hydroxy group; a substituted hydroxy group represented by the formula -OR$_3$, where R$_3$ is C$_{1-10}$ unsubstituted akyl or C$_{1-10}$ substituted alkyl, alkoxyalkyl, aryloxyalkyl, cycloalkyl, alkenylalkyl in which the alkyl group is unsubstituted alkylene, cycoalkyl in which the cycloalkyl group ha 3–7 carbon atoms, —OCOR, aryl, heteroaryl, acetal, or said substituted groups comprise two hydroxyl groups that are joined to form a ketal;

(f) halogen substituents fluorine or chlorine; and (g) hydrogen, forming a deoxy sugar; wherein R, R$_1$, and R$_2$ are independently hydrogen or C$_{1-10}$ unsubstituted alkyl or C$_{1-10}$ substituted alkyl or a aryl, or a derivative of the compound, said derivative comprising salts, coordination complexes with metal ions, esters, free acids or bases, hydrates or protecting groups.

13. A composition of comprising a compound of claim 12 in combination with a pharmaceutically acceptable carrier.

14. A compound of claim 12 wherein said substituted hydroxy group is OR$_3$, and R$_3$ is selected from the group consisting of CHF$_2$ and CF$_3$.

15. The compound of claim 12, wherein said derivative is a coordination complex with a metal ion selected from the group consisting of Mn(+2) and Zn(+2).

\* \* \* \* \*